US012740986B2

(12) United States Patent
Woody

(10) Patent No.: US 12,740,986 B2
(45) Date of Patent: Sep. 22, 2026

(54) HISTONE DEACETYLASE INHIBITORS FOR USE IN IMMUNOTHERAPY

(71) Applicant: Viracta Subsidiary, Inc., Cardiff, CA (US)

(72) Inventor: James N. Woody, Cardiff, CA (US)

(73) Assignee: Viracta Subsidiary, Inc., Cardiff (CA)

( * ) Notice: Subject to any disclaimer, the term of this patent is extended or adjusted under 35 U.S.C. 154(b) by 547 days.

(21) Appl. No.: 18/057,161

(22) Filed: Nov. 18, 2022

(65) Prior Publication Data

US 2023/0149413 A1 May 18, 2023

Related U.S. Application Data

(63) Continuation of application No. 16/317,750, filed as application No. PCT/US2017/042199 on Jul. 14, 2017, now abandoned.

(60) Provisional application No. 62/362,959, filed on Jul. 15, 2016.

(51) Int. Cl.

| | |
|---|---|
| ***A61K 39/00*** | (2006.01) |
| ***A61K 9/00*** | (2006.01) |
| ***A61K 31/4709*** | (2006.01) |
| ***A61K 31/506*** | (2006.01) |
| ***A61K 31/522*** | (2006.01) |
| ***A61K 38/15*** | (2006.01) |
| ***A61K 38/17*** | (2006.01) |
| ***A61K 39/395*** | (2006.01) |
| ***A61K 40/11*** | (2025.01) |
| ***A61K 40/31*** | (2025.01) |
| ***A61K 40/46*** | (2025.01) |
| ***A61K 45/06*** | (2006.01) |
| ***A61P 31/22*** | (2006.01) |
| ***A61P 35/00*** | (2006.01) |
| ***A61P 35/04*** | (2006.01) |
| ***C12N 9/80*** | (2006.01) |

(52) U.S. Cl.

CPC .......... *A61K 31/522* (2013.01); *A61K 9/0053* (2013.01); *A61K 31/4709* (2013.01); *A61K 31/506* (2013.01); *A61K 38/15* (2013.01); *A61K 38/177* (2013.01); *A61K 38/1774* (2013.01); *A61K 39/3955* (2013.01); *A61K 39/39558* (2013.01); *A61K 40/11* (2025.01); *A61K 40/31* (2025.01); *A61K 40/46* (2025.01); *A61K 45/06* (2013.01); *A61P 31/22* (2018.01); *A61P 35/00* (2018.01); *A61P 35/04* (2018.01); *C12N 9/80* (2013.01); *A61K 2039/505* (2013.01); *A61K 2239/31* (2023.05); *A61K 2239/38* (2023.05); *A61K 2239/48* (2023.05); *A61K 2239/51* (2023.05)

(58) Field of Classification Search

CPC .... A61K 31/522; A61K 9/0053; A61K 40/46; A61P 35/00

See application file for complete search history.

(56) References Cited

U.S. PATENT DOCUMENTS

| | | | |
|---|---|---|---|
| 3,471,513 | A | 10/1969 | Leland |
| 3,904,612 | A | 9/1975 | Nagasawa et al. |
| 4,008,323 | A | 2/1977 | Cousse et al. |
| 4,011,336 | A | 3/1977 | Amann et al. |
| 4,026,895 | A | 5/1977 | Tanaka et al. |
| 4,026,896 | A | 5/1977 | Harita et al. |
| 4,031,243 | A | 6/1977 | Aparicio et al. |
| 4,058,558 | A | 11/1977 | Cousse et al. |
| 4,131,617 | A | 12/1978 | Esanu |
| 4,176,193 | A | 11/1979 | Esanu |
| 4,234,599 | A | 11/1980 | Van et al. |
| 4,613,616 | A | 9/1986 | Winston et al. |
| 4,671,901 | A | 6/1987 | Green |
| 4,699,926 | A | 10/1987 | Abraham et al. |
| 4,704,402 | A | 11/1987 | Abraham et al. |
| 4,723,958 | A | 2/1988 | Pope et al. |
| 4,731,381 | A | 3/1988 | Abraham et al. |
| 4,732,914 | A | 3/1988 | Morton, Jr. |
| 4,735,967 | A | 4/1988 | Neesby |
| 4,747,825 | A | 5/1988 | Linkie et al. |
| 4,751,244 | A | 6/1988 | Abraham et al. |
| 4,766,116 | A | 8/1988 | Tatsuoka et al. |
| 4,820,711 | A | 4/1989 | Pearlman |
| 4,822,821 | A | 4/1989 | Perrine |
| 4,849,426 | A | 7/1989 | Pearlman |
| 4,851,229 | A | 7/1989 | Magruder et al. |
| 4,853,388 | A | 8/1989 | Pearlman |

(Continued)

FOREIGN PATENT DOCUMENTS

| | | |
|---|---|---|
| CA | 1209037 A1 | 8/1986 |
| CA | 2173976 A1 | 4/1995 |

(Continued)

OTHER PUBLICATIONS

Abbott, et al. Quantitative structure-anticonvulsant activity relationships of valproic acid, related carboxylic acids and tetrazoles. Neuropharmacology. Mar. 1988;27(3):287-94.

(Continued)

*Primary Examiner* — Julie Wu

(74) *Attorney, Agent, or Firm* — Wilson Sonsini Goodrich & Rosati

(57) ABSTRACT

Provided are methods and compositions for the treatment of cancer. The methods comprise administering to a subject an HDAC inhibitor and an immunotherapeutic. In certain instances the immunotherapeutic is a chimeric antigen receptor T cell, an antibody or polypeptide that binds a checkpoint inhibitor, or a vaccine.

9 Claims, 3 Drawing Sheets

(56) References Cited

U.S. PATENT DOCUMENTS

| | | | |
|---|---|---|---|
| 4,880,624 | A | 11/1989 | Metcalf et al. |
| 4,894,364 | A | 1/1990 | Greer |
| 4,925,873 | A | 5/1990 | Friedhoff et al. |
| 4,948,592 | A | 8/1990 | Ayer et al. |
| 4,952,560 | A | 8/1990 | Kigasawa et al. |
| 4,958,592 | A | 9/1990 | Anthony et al. |
| 4,965,251 | A | 10/1990 | Stamatoyannopoulos |
| 4,968,340 | A | 11/1990 | Kaku et al. |
| 4,997,815 | A | 3/1991 | Perrine et al. |
| 5,023,251 | A | 6/1991 | Sattler et al. |
| 5,025,029 | A | 6/1991 | Perrine |
| 5,032,507 | A | 7/1991 | Yu et al. |
| 5,039,703 | A | 8/1991 | Breuer |
| 5,081,124 | A | 1/1992 | Hughes |
| 5,100,647 | A | 3/1992 | Agus et al. |
| 5,137,734 | A | 8/1992 | Spiegelman et al. |
| 5,139,563 | A | 8/1992 | Astles et al. |
| 5,185,436 | A | 2/1993 | Villa et al. |
| 5,199,942 | A | 4/1993 | Gillis |
| 5,208,333 | A | 5/1993 | Paul et al. |
| 5,216,004 | A | 6/1993 | Perrine |
| 5,258,367 | A | 11/1993 | Bazer et al. |
| 5,270,458 | A | 12/1993 | Lemischka |
| 5,366,996 | A | 11/1994 | Elford et al. |
| 5,378,716 | A | 1/1995 | Hamanaka et al. |
| 5,403,590 | A | 4/1995 | Forse |
| 5,403,867 | A | 4/1995 | Okumura et al. |
| 5,468,731 | A | 11/1995 | Matsuo et al. |
| 5,635,532 | A | 6/1997 | Samid |
| 5,654,333 | A | 8/1997 | Samid |
| 5,661,179 | A | 8/1997 | Samid |
| 5,674,898 | A | 10/1997 | Cheng et al. |
| 5,674,912 | A | 10/1997 | Martin |
| 5,679,707 | A | 10/1997 | Okumura et al. |
| 5,710,178 | A | 1/1998 | Samid |
| 5,750,571 | A | 5/1998 | Cheng et al. |
| 5,827,642 | A | 10/1998 | Riddell et al. |
| 5,843,994 | A | 12/1998 | Samid |
| 5,858,365 | A | 1/1999 | Faller |
| 5,932,545 | A | 8/1999 | Henkin et al. |
| 5,939,456 | A | 8/1999 | Perrine |
| 5,945,407 | A | 8/1999 | Bemis et al. |
| 6,011,000 | A | 1/2000 | Perrine et al. |
| 6,030,961 | A | 2/2000 | Nudelman et al. |
| 6,043,389 | A | 3/2000 | Nudelman et al. |
| 6,197,743 | B1 | 3/2001 | Faller |
| 6,231,880 | B1 | 5/2001 | Perrine |
| 6,284,240 | B1 | 9/2001 | Seed et al. |
| 6,316,257 | B1 | 11/2001 | Flyer et al. |
| 6,399,054 | B1 | 6/2002 | Casorati et al. |
| 6,403,647 | B1 | 6/2002 | Perrine |
| 6,451,334 | B2 | 9/2002 | Perrine |
| 6,677,302 | B2 | 1/2004 | Faller |
| 7,618,817 | B2 | 11/2009 | Campbell |
| 7,745,140 | B2 | 6/2010 | June et al. |
| 7,932,246 | B2 | 4/2011 | Moffat et al. |
| 8,313,943 | B2 | 11/2012 | Campbell |
| 8,383,099 | B2 | 2/2013 | Dudley et al. |
| 11,071,774 | B2 | 7/2021 | Soon-Shiong et al. |
| 11,207,392 | B2 | 12/2021 | Soon-Shiong et al. |
| 12,427,152 | B2 | 9/2025 | Woody et al. |
| 2001/0009922 | A1 | 7/2001 | Faller |
| 2001/0027215 | A1 | 10/2001 | Perrine |
| 2003/0018069 | A1 | 1/2003 | Faller et al. |
| 2003/0134341 | A1 | 7/2003 | Gruenberg |
| 2004/0241162 | A1 | 12/2004 | Berenson et al. |
| 2006/0074046 | A1 | 4/2006 | Redkar et al. |
| 2007/0072793 | A1 | 3/2007 | Chung |
| 2008/0015190 | A1 | 1/2008 | Chakravarty et al. |
| 2008/0057086 | A1 | 3/2008 | Etter |
| 2008/0075692 | A1 | 3/2008 | Perrine |
| 2008/0207590 | A1 | 8/2008 | Deziel et al. |
| 2009/0082444 | A1 | 3/2009 | Perrine et al. |
| 2009/0130134 | A1 | 5/2009 | Pancre et al. |
| 2009/0131367 | A1 | 5/2009 | Gore et al. |
| 2009/0137567 | A1 | 5/2009 | Perrine et al. |
| 2009/0298924 | A1 | 12/2009 | Davidson et al. |
| 2010/0010010 | A1 | 1/2010 | Davidson et al. |
| 2010/0152155 | A1 | 6/2010 | Moffat et al. |
| 2010/0280113 | A1 | 11/2010 | Faller et al. |
| 2010/0317678 | A1 | 12/2010 | Moffat et al. |
| 2011/0086869 | A1 | 4/2011 | Perrine et al. |
| 2011/0245154 | A1 | 10/2011 | Berenson et al. |
| 2011/0251149 | A1 | 10/2011 | Perrine et al. |
| 2012/0310183 | A1 | 12/2012 | Epner et al. |
| 2013/0287748 | A1 | 10/2013 | June et al. |
| 2013/0331313 | A1 | 12/2013 | Berenson et al. |
| 2014/0045774 | A1 | 2/2014 | Perrine et al. |
| 2014/0050708 | A1 | 2/2014 | Powell et al. |
| 2014/0170221 | A1 | 6/2014 | Irvine et al. |
| 2014/0234348 | A1 | 8/2014 | Scholler et al. |
| 2014/0341989 | A1 | 11/2014 | Loury et al. |
| 2015/0023907 | A1 | 1/2015 | Van Lint et al. |
| 2015/0023937 | A1 | 1/2015 | Vera Valdes et al. |
| 2015/0099012 | A1 | 4/2015 | Mahmoudi |
| 2015/0210772 | A1 | 7/2015 | Kim |
| 2015/0218274 | A1* | 8/2015 | Sabatos-Peyton .......................... G01N 33/57492 435/254.2 |
| 2016/0113929 | A1 | 4/2016 | Berenson et al. |
| 2016/0159905 | A1* | 6/2016 | Abdiche ................ A61K 39/39 435/254.2 |
| 2016/0317624 | A1 | 11/2016 | Casebolt et al. |
| 2016/0361360 | A1* | 12/2016 | Chang ..................... A61P 17/06 |
| 2017/0021002 | A1 | 1/2017 | Wagner et al. |
| 2017/0037132 | A1* | 2/2017 | Manekas ............ C07K 16/2827 |
| 2017/0042898 | A1 | 2/2017 | Berenson et al. |
| 2017/0327582 | A1 | 11/2017 | Bissonnette et al. |
| 2018/0161371 | A1 | 6/2018 | O'Dwyer |
| 2018/0185345 | A1 | 7/2018 | Faller |
| 2019/0175731 | A1 | 6/2019 | Coric |
| 2019/0216818 | A1 | 7/2019 | Woody |
| 2019/0247481 | A1 | 8/2019 | Soon-Shiong |
| 2019/0290646 | A1 | 9/2019 | Woody et al. |
| 2019/0318804 | A1 | 10/2019 | Soon-Shiong |
| 2019/0381156 | A1 | 12/2019 | Soon-Shiong et al. |
| 2020/0171137 | A1 | 6/2020 | Soon-Shiong et al. |
| 2020/0270574 | A1 | 8/2020 | Soon-Shiong et al. |
| 2020/0368280 | A1 | 11/2020 | Warren et al. |
| 2020/0375990 | A1 | 12/2020 | Mcrae et al. |
| 2020/0388348 | A1 | 12/2020 | Givechian et al. |
| 2021/0024611 | A1 | 1/2021 | Soon-Shiong |
| 2021/0046118 | A1 | 2/2021 | O'Dwyer |
| 2021/0213041 | A1 | 7/2021 | Ting et al. |
| 2024/0366597 | A1 | 11/2024 | Rojkjaer et al. |
| 2026/0000672 | A1 | 1/2026 | Woody |
| 2026/0007676 | A1 | 1/2026 | Woody et al. |

FOREIGN PATENT DOCUMENTS

| | | | |
|---|---|---|---|
| CA | 3002755 | A1 | 5/2017 |
| CN | 101163696 | A | 4/2008 |
| CN | 102391359 | A | 3/2012 |
| CN | 102516124 | A | 6/2012 |
| CN | 102675153 | A | 9/2012 |
| CN | 102793693 | A | 11/2012 |
| CN | 103232474 | A | 8/2013 |
| CN | 104083763 | A | 10/2014 |
| CN | 105055386 | A | 11/2015 |
| CN | 105647946 | A | 6/2016 |
| CN | 108347929 | A | 7/2018 |
| EP | 2683371 | A1 | 1/2014 |
| GB | 2126082 | A | 3/1984 |
| JP | S5089335 | A | 7/1975 |
| JP | S61180740 | A | 8/1986 |
| JP | 6208667 | B2 | 10/2017 |
| RU | 2555474 | C1 | 7/2015 |
| WO | WO-9307866 | A2 | 4/1993 |
| WO | WO-9307866 | A3 | 5/1993 |
| WO | WO-9511699 | A1 | 5/1995 |
| WO | WO-9627369 | A2 | 9/1996 |
| WO | WO-9627369 | A3 | 11/1996 |
| WO | WO-9704761 | A1 | 2/1997 |
| WO | WO-9804290 | A2 | 2/1998 |

(56) References Cited

FOREIGN PATENT DOCUMENTS

| | | | |
|---|---|---|---|
| WO | WO-9804290 | A3 | 8/1998 |
| WO | WO-2006121168 | A1 | 11/2006 |
| WO | WO-2006123121 | A1 | 11/2006 |
| WO | WO-2008097654 | A1 | 8/2008 |
| WO | WO-2011038224 | A1 | 3/2011 |
| WO | WO-2011113013 | A2 | 9/2011 |
| WO | WO-2012120262 | A1 | 9/2012 |
| WO | WO-2013033656 | A1 | 3/2013 |
| WO | WO-2013086379 | A2 | 6/2013 |
| WO | WO-2013110280 | A1 | 8/2013 |
| WO | WO-2013149026 | A2 | 10/2013 |
| WO | WO-2013181584 | A2 | 12/2013 |
| WO | WO-2014144791 | A2 | 9/2014 |
| WO | WO-2015010096 | A1 | 1/2015 |
| WO | WO-2015160986 | A2 | 10/2015 |
| WO | WO-2016010879 | A1 | 1/2016 |
| WO | WO-2016077734 | A2 | 5/2016 |
| WO | WO-2016109668 | A1 | 7/2016 |
| WO | WO-2016153839 | A1 | 9/2016 |
| WO | WO-2016205695 | A1 | 12/2016 |
| WO | WO-2017041043 | A1 | 3/2017 |
| WO | WO-2017053823 | A1 | 3/2017 |
| WO | WO-2017100709 | A1 | 6/2017 |
| WO | WO-2017120204 | A2 | 7/2017 |
| WO | WO-2017197140 | A1 | 11/2017 |
| WO | WO-2017202949 | A1 | 11/2017 |
| WO | WO-2018013962 | A1 | 1/2018 |
| WO | WO-2018013975 | A1 | 1/2018 |
| WO | WO-2019072220 | A1 | 4/2019 |
| WO | WO-2019140296 | A1 | 7/2019 |
| WO | WO-2020243326 | A1 | 12/2020 |
| WO | WO-2021071809 | A1 | 4/2021 |
| WO | WO-2023003972 | A1 | 1/2023 |

OTHER PUBLICATIONS

Almstedt et al., The DNA demethylating agent 5-aza-2'-deoxycytidine induces expression of NY-ESO-1 and other cancer/testis antigens in myeloid leukemia cells. Leukemia Research. 34(7):899-905 (2010).

Antoni, et al. NF-.kappa. B-Dependent and -Independent Pathways of HIV Activation in a Chronically Infected T Cell Line. Virology. 1994;202:684-694.

Archin, et al. Antiretroviral intensification and valproic acid lack sustained effect on residual HIV-1 viremia or resting CD4+ cell infection. PLoS One. Feb. 23, 2010;5(2):e9390 (p. 1-4).

Archin, et al. Expression of latent HIV induced by the potent HDAC inhibitor suberoylanilide hydroxamic acid. AIDS Res Hum Retroviruses. Feb. 2009;25(2):207-12.

Archin, et al. Expression of latent human immunodeficiency type 1 is induced by novel and selective histone deacetylase inhibitors. AIDS. Sep. 10, 2009;23(14):1799-806.

Archin, et al. Valproic acid without intensified antiviral therapy has limited impact on persistent HIV infection of resting CD4+ T cells. AIDS. Jun. 19, 2008;22(10):1131-5.

Armstrong, et al. Criteria for the definition of Epstein-Barr virus association in Hodgkin's disease. Leukemia. 6(9):869-874, (1992).

Arrighetti et al., Drug Combination with HDAC Inhibitors in Antitumor Therapy. Critical Reviews in Oncogenesis 20(1-2): 83-117 (2015).

Arvey et al., An atlas of the Epstein-Barr virus transcriptome and epigenome reveals host-virus regulatory interactions. Cell Host & Microbe. 12(2):233-245 (2012).

Banerji et al., A Phase I Pharmacokinetic and Pharmacodynamic Study Histone Deacetylase Inhibitor in Refractory Solid Tumors. Clinical Cancer Research 18(9): 2687-2694 (2012).

Barker, et al. The actions of cyclic AMP, its butyryl derivatives and Na butyrate on the proliferation of malignant trophoblast cells in vitro, Br. J. Cancer. 1977;35:314-321.

Bingham. Patty's Toxicology. John Wiley and Sons, Incorporated. Jan. 1, 2001;5:707-711.

Bissonnette, R. et al., "Abstract B108: The HDAC inhibitor HBI-8000 enhances immunotherapy with either PD- or PD-L1 blockage in the MC38 model of colon cancer", Cancer Immunology Research, Nov. 2016, vol. 4, Issue 11, pp. 1-4.

Bloch. Induced cell differentiation in cancer therapy. Cancer Treatment Reports. 1984;68:199-205.

Bohan, et al. Mutational analysis of sodium butyrate inducible elements in the human immunodeficiency virus type 1 long terminal repeat. Virology. 1989; 172:573-583.

Bohan, et al. Sodium butyrate activates human immunodeficiency virus long terminal repeat—directed expression. Biochem and Biophys. Res. Comm. 1987;148(3):899-905.

Bonnet et al., Detection of Epstein-Barr virus in invasive breast cancers. J Nat Cancer Inst. 91(16):1376-1381 (1999).

Bora-Singhal et al., Novel HDAC11 inhibitors suppress lung adenocarcinoma stem cell self-renewal and overcome drug resistance by suppressing Sox2. Scientific Reports 10: 4722 (2020).

Bourgeade, et al. Effect of sodium butyrate on the antiviral and anticellular action of interferon in normal and MSV-transformed cells. Int J Cancer. Sep. 15, 1979;24(3):314-8.

Bourgeade, et al. Enhancement of interferon anti-tumor action by sodium butyrate. Cancer Res. 1979;39:4720-4723.

Bridle et al.,. HDAC inhibition suppresses primary immune responses, enhances secondary immune responses, and abrogates autoimmunity during tumor immunotherapy. Molecular Therapy. 21(4):887-894 (2013).

Briz et al., Epstein-Barr virus associated B-cell lymphoma after autologous bone marrow transplantation for T-cell acute lymphoblastic leukaemia. British Journal of Haematology. 98(2):485-487 (1997).

Brooks, et al. Epstein-Barr virus and lymphomas. Cancer Surv. 1999;33:99-123.

Burkitt, A sarcoma involving the jaws in African children. The British Journal of Surgery. 46(127):218-223 (1958).

Callery, et al. Identification of metabolites of the cell—differentiating agent hexamethylene bisacetamide in humans. Cancer Res. 1986;46:4900-4903.

Canceill, et al. Stereochimstry of the reduction of b-keto esters, p-keto amides, and b-keto nitriles by hydrides. Bull. Soc. Chim. 1970 Fr. 6:2180-2187. (Abstract only).

Caruso, et al. Regression of established macroscopic liver metastases after in situ transduction of a suicide gene. Proc Natl Acad Sci U S A. Aug. 1, 1993;90(15):7024-8.

Chandrashekara, The treatment strategies of autoimmune disease may need a different approach from conventional protocol: A review. Indian Journal of Pharmacology 44(6): 665-671 (2012).

Chin et al.: Immune Intervention with Monoclonal Antibodies Targeting CD152 (CTLA-4) for Autoimmune and Malignant Diseases. Chang Gung Med J. 31(1):1-15 (2008).

Choi et al., Activation of CMV promoter-controlled glycosyltransferase and beta-galactosidase glycogenes by butyrate, tricostatin A, and 5-aza-2'-deoxycytidine. Glycoconjugate Journal. 22(1-2):63-69 (2005).

Chu, et al. In situ detection of Epstein-Barr virus in breast cancer. Cancer Lett. 1998;124:53-57.

Chung, et al. A novel approach for nasopharyngeal carcinoma treatment uses phenylbutyrate as a protein kinase C modulator: implications for radiosensitization and EBV-targeted therapy. Clin Cancer Res. Apr. 2000;6(4):1452-8.

Coates, et al. Persistence of Epstein-Barr virus in Reed-Sternberg cells throughout the course of Hodgkin's disease. J Pathol. 1991; 164:291-297.

Colombo. Natural history and pathogenesis of hepatitis C virus related hepatocellular carcinoma. Journal of Hepatology. 1999;31:(1):25-30. Suppl.

Coral et al., Phenotypic and functional changes of human melanoma xenografts induced by DNA hypomethylation: immunotherapeutic implications. Journal of Cellular Physiology. 207(1):58-66 (2006).

Countryman et al., Histone hyperacetylation occurs on promoters of lytic cycle regulatory genes in Epstein-Barr virus-infected cell lines which are refractory to disruption of latency by histone deacetylase inhibitors. Journal of Virology. 82(10):4706-4719 (2008).

Curtis, et al. Risk of lymphoproliferative disorders after bone marrow transplantation: A multi-institutional study. Blood. 1999;94:2208-2216.

(56) References Cited

OTHER PUBLICATIONS

Cycon et al., Histone deacetylase inhibitors activate CIITA and MHC class II antigen expression in diffuse large B-cell lymphoma. Immunology. 140(2):259-272 (2013).
Daniel. Pharmacokinetic study of butyric acid administered in vivo as sodium and arginine butyrate salts. Clinica Chimica Acta. 1989;181:255-264.
Dantchev,et al. Behavior of certain pyrimidine compounds of fumeric acid, and of malic acid with regard to the protection of red blood cells of the rabbit intoxicated with phenylhydrazine. Comportement de certain composés pyrimidiques, de 1' acidew fumarique et de 1' acide maléique â 1' égard de las protection des globules rouges du lapin intoxiqut par la phénylhydrazine C.R. Acad. Sci. Hebd. Sceances Acad. Sci. D. Mar. 1967;264(11):1467-1470. (in French with English abstract).
De Bruin, et al. Detection of Epstein-Barr virus nucleic acid sequences and protein in nodal T-cell lymphomas: relation between latent membrane protein I positively and clinical course. Histopathology. 1993;23:509-509.
De Bruin, et al. Presence of Epstein-Barr virus in extranodal T-cell lymphomas: differences in relation to site. Blood. 1994;83(10):1612-1612.
De Smet et al., DNA methylation is the primary silencing mechanism for a set of germ line- and tumor-specific genes with a CpG-rich promoter. Molecular and Cellular Biology. 19(11):7327-7335 (1999).
De Smet et al., The activation of human gene MAGE-1 in tumor cells is correlated with genome-wide demethylation. Proceedings of the National Academy of Sciences of the United States of America. 93(14):7149-7153 (1996).
Deeks, Nivolumab: A review of Its Use in Patients with Malignant Melanoma. Drugs 74: 1233-1239 (2014).
Dimaio, et al. Directed enzyme pro-drug gene therapy for pancreatic cancer in vivo. Surgery. Aug. 1994; 116(2):205-13.
Dokmanovic, et al. Histone deacetylase inhibitors: overview and perspectives. Mol Cancer Res. Oct. 2007;5(10):981-9.
Egorin, et al. Phase 1 clinical and pharmacokinetic study of hexamethylene bisacetamide (NSC 95580) administered as a five-day continuous infusion. Cancer. Res. 1987;47:617-623.
Elaut, et al. The pharmaceutical potential of histone deacetylase inhibitors. Curr Pharm Des. 2007;13(25):2584-620.
Faller, et al. Arginine butyrate-induced susceptibility to ganciclovir in an Epstein-Barr Virus (EBV) associated lymphona. Am. Soc. of Hematology [Blood]. 1995;86(10)(1):342a.
Faller, et al. Arginine Butyrate-induced susceptibility to ganciclovir in Epstein-Barr virus (EBV)-associated lymphomas. Proceedings of the American Association for Cancer Research. 1996;37:411-412.
Faller, et al. Phase I/II trial of arginne butyrate to induce viral TK gene expression in Epstein-Barr Virus (EBV)-associated lymphomas. Proc. Am. Assn. for Cancer Research. Mar. 2000;41:544. (Abstract only).
Feng, et al. Valproic acid enhances the efficacy of chemotherapy in EBV-positive tumors by increasing lytic viral gene expression. Cancer Res. Sep. 1, 2006;66(17):8762-9.
Flyer, et al. Retrovirus-induced changes in major histocompatibility complex antigen expression influence susceptibility to lysis by cytotoxic T lymphocytes. The Journal of Immunology. Oct. 1985;135(4):2287-92.
Foss, et al. Biomodulatory effects of butyric acid derivatives on leukemia and lymphoma cells. Blood. 1993; 82/10 Suppl. 1:564A. (1993) The American Society of Hematology, 35th Annual Meeting, Dec 3-7, Abstract only.
Ghosh, et al. Short, discontinuous exposure to butyrate effectively sensitizes latently EBV- infected lymphoma cells to nucleoside analogue antiviral agents. Blood Cells Mol Dis. Jan.-Feb. 2007;38(1):57-65. Epub Dec. 11, 2006.
Gilbert, et al. A phase I dose escalation and bioavailability study of oral sodium phenylbutyrate in patients with refractory solid tumor malignancies. Clin Cancer Res. Aug. 2001;7(8):2292-300.
Glaser, et al. Epstein-Barr virus-associated Hodgkin's disease: epidemiologic characteristics in international data. Int J Cancer. 1997;70(4):375-382.
Glaser, K. HDAC inhibitors: clinical update and mechanism-based potential. Biochem Pharmacol. Sep. 1, 2007;74(5):659-71. Epub Apr. 7, 2007.
Golub, et al. Induction of dormant HIV-1 by sodium butyrate: involvement of the TATA box in the activation of the HIV-1 promoter. AIDS. 1991;5(6):663-668.
Gradoville, et al. Protein kinase C-independent activation of the Epstein-Barr virus lytic cycle. J Virol. Jun. 2002;76(11):5612-26.
Gredmark, et al. Active cytomegalovirus replication in patients with coronary disease. Scand Cardiovasc J. Aug. 2007;41(4):230-4.
Greenspan, et al. Replication of Epstein-Barr virus within the epithelial cells of oral "hairy" leukoplakia, an AIDS-associated lesion. N Engl J Med. 1985;313:1564-1564.
Gross, et al. B cell lymphoproliferative disorders following hematopoietic stem cell transplantation. Risk factors, treatment and outcome. Bone Marrow Transplant. 1999;23:251-258.
Grossi, et al., Effects of monosaccharide esters of butyric acid on the synthesis of hemoglobin T chain and erythroleukemis cell line, Abstract of ASH Annual Meeting, Seattle, WA, Dec. 1-5, 1995.
Grufferman, et al. Hodgkin's disease in siblings. N Engl J Med. 1977;296:248-250.
Guilbaud, et al. Effects of differentiation-inducing agents on maturation of human MCF-7 breast cancer cells. Journal of Cellular Physiology. 1990; 145:162-172.
Gum, et al. Effects of sodium butyrate on human colonic adenocarcinoma cells. The Journal of Biological Chemistry. Jan. 25, 1987;262(3):1092-1097.
Hahn, et al. Therapeutic outcome of Epstein-Barr virus positive T/NK cell lymphoma in the upper aerodigestive tract. Yonsei Med J. 2002;43:175-182.
Hanto, et al. Epstein-Barr virus-induced polyclonal and monoclonal B-cell lymphoproliferative diseases occurring after renal transplantation. Ann Surg. 1983;198:356-369.
Harabuchi, et al. Epstein-Barr virus in nasal T-cell lymphomas in patients with lethal midline granuloma. Lancet. 1990;335:128-128.
Harig, et al. Treatment of diversion colitis with short-chain-fatty acid irrigation. N. Engl. J. Med. 1989;320(1):23-28.
Hausen, et al. EBV DNA in biopsies of Burkitt tumours and anaplastic carcinomas of the nasopharynx. Nature. 1970;228(5276):1056-1058.
Heninger et al., Augmenting antitumor immune responses with epigenetic modifying agents. Frontiers in Immunology 6: 29 (2015).
Henle, et al. Epstein-Barr virus and human malignancies. Cancer. Oct. 1974;34(4 Suppl):suppl:1368-74.
Henle et al., Relation of Burkitt's tumor-associated herpes-type virus to infectious mononucleosis. Proc Natl Acad Sci USA. 59(1):94-101 (1968).
Henry, D.H. Supplemental Iron: A Key to Optimizing the Response of Cancer-Related Anemia to rHuEPO?. The Oncologist. Aug. 1998;3(4): 275-8.
Herbst et al., Epstein-Barr virus latent membrane protein expression in Hodgkin and Reed-Sternberg cells. Proc Natl Acad Sci USA. 88(11):476-4770 (1991).
Hermanson et al., Utilizing chimeric antigen receptors to direct natural killer cell activity. Frontiers in Immunology 8: 195 (2015).
Ho, et al. Presence of Epstein-Barr virus DNA in nasal lymphomas. Hematol Oncol. 1990;8:271-271.
Hoessly, et al. Factors responsible for variable reported lineages of HL-60 cells induced to mature with butyric acid. Cancer Research. Jul. 1, 1989;49:3594-97.
Hoey, et al. Molecular cloning and functional analysis of drosophila TAF110 reveal properties expected of coactivators. Cell. 1993;72:247-60.
Hsu, et al. Epstein-Barr virus-associated malignancies: epidemiologic patterns and etiologic implications. Crit Rev Oncol Hematol. 2000;34:27-53.
Huber, et al. In vivo antitumor activity of 5-fluorocytosine on human colorectal carcinoma cells genetically modified to express cytosine deaminase. Cancer Res. Oct. 1, 1993;53(19):4619-26.

(56) References Cited

OTHER PUBLICATIONS

Huber, et al. Metabolism of 5-fluorocytosine to 5-fluorouracil in human colorectal tumor cells transduced with the cytosine deaminase gene: significant antitumor effects when only a small percentage of tumor cells express cytosine deaminase. Proc Natl Acad Sci U S A. Aug. 16, 1994;91(17):8302-6.
Ingram et al.: Anti-CTLA-4 therapy requires an Fc domain for efficacy. Proc. Natl. Acad. Sci. USA. 115(15):3912-3917 (2018).
International Application No. PCT/US17/42199 International Search Report and Written Opinion Mailed Oct. 6, 2017.
International Application No. PCT/US17/42222 International Search Report and Written Opinion Mailed Sep. 29, 2017.
International Application No. PCT/US2016/038148 International Preliminary Report on Patentability Mailed Dec. 28, 2017.
Jiang et al.: A novel peptide isolated from a phage display peptide library with trastuzumab can mimic antigen epitope of HER-2*. J Biol Chem. 280(6):4656-4662 doi:10.1074/jbc.M411047200 (2005).
Jiwa, et al. Epstein-Barr virus DNA in Reed-Sternberg cells of Hodgkin's disease is frequently associated with CR2 (EBV receptor) expression. Histopathology. 1992;21:51-51.
Jochems et al., An NK cell line (haNK) expressing high levels of granzyme and engineered to express the high affinity CD16 allele. Oncotarget 7(52): 86359-86373 (2016).
Johansson, et al. Epstein-Barr Virus (EBV)-associated antibody pattern in malignant lymphoma and leukemia. 1. Hodgkin's disease. Int J Cancer. 1970;5:450-450.
Johnson et al., The Clinical Impact of Screening and other Experimental Tumor Studies. Cancer Treatment Reviews 2: 1-31 (1975).
Jones, et al. Sodium valproate in combination with ganciclovir induces lysis of EBV-infected lymphoma cells without impairing EBV-specific T-cell immunity. Int J Lab Hematol. Feb. 2010;32(1 Pt 1):e169-74. Epub Jan. 12, 2009.
Jones, et al. T-cell lymphomas containing Epstein-Barr virus DNA in patients with chronic Epstein-Barr virus infections. N Engl J Med. 1988;318(12):733-733.
Kawa. Epstein-Barr virus-associated disease in humans. Int J Hematol. 2000;71:108-117.
Keedy, et al. A limited group of class I histone deacetylases acts to repress human immunodeficiency virus type 1 expression. J Virol. May 2009;83(10):4749-56.
Kiany et al., Combination of NK cells therapy and oral administration of entinostat as an approach for osteosarcoma lung metastasis treatment. Journal for Immunotherapy of Cancer 3(Supp. 2):P25 (2015).
Kim et al., Eradication of metastatic mouse cancers resistant to immune checkpoint blockade by suppression of myleloid-derived cells. PNAS 111(32): 11774-11779 (2014).
Kleer, et al. Detection of Epstein-Barr virus in rapidly growing fibroadenomas of the breast in immunosuppressed hosts. Modern Pathol. 2002;15(7):759-764.
Klingernann et al., Natural Killer Cells for Immunotherapy-Advantages of the NK-92 Cell Line over Blood NK Cells. Fronties in Immunology 7:91 (2016).
Korbjuhn et al., Frequent latent Epstein-Barr virus infection of neoplastic T cells and bystander B cells in human immunodeficiency virus-negative European peripheral pleomorphic T-cell lymphomas. Blood. 82(1):217-223 (1993).
Krantis, et al. Augmentation of cysteamine-induced ulceration of rat duodenum by systemically administered g-Aminobutyric Acid (GABA). Digestive Diseases and Sciences. Aug. 1989;34(8m):1211-1216.
Kroesen et al., HDAC inhibitors and immunotherapy; a double edged sword? Oncotarget. 5(16):6558-6572 (2014).
Kwong, et al. Natural killer cell lymphoma/leukemia: pathology and treatment. Hematol Oncol. 1997;15:71-79.
Lee, et al. Essential role of PKCdelta in histone deacetylase inhibitor-induced Epstein-Barr virus reactivation in nasopharyngeal carcinoma cells. J Gen Virol. Apr. 2008; 89(Pt 4):878-83.
Lee, et al. The association of Epstein-Barr virus with smooth-muscle tumors occurring after organ transplantation. N Engl J Med. 1995;332:19-25.
Leoncini, et al. Epstein-Barr virus and gastric cancer: data and unanswered questions. Int J Cancer. 1993;53:898-901.
Liu et al., Growth and Activation of Natural Killer Cells Ex Vivo from Children with Neuroblastoma for Adoptive Cell Therapy. Clin Cancer Res. 19(8): 2132-2143 (2013).
Magrath, et al. Breast cancer: a new Epstein-Barr virus-associated disease? J Nat Cancer Inst. 1999;91:1349-1350.
Maia, et al. Chronic, active Epstein-Barr virus infection. Curr Opin Hematol. 2000;7:59-63.
Matalon, et al. The histone deacetylase inhibitor ITF2357 decreases surface CXCR4 and CCR5 expression on CD4(+) T-cells and monocytes and is superior to valproic acid for latent HIV-1 expression in vitro. Journal of Acquired Immune Deficiency Syndromes. (54)1:1-9 (2010).
Maziarz, et al. The regulation of exogenous and endogenous class I MHC genes in a human tumor cell line, K562. Molecular Immunology. 1990;27:135-142.
McClain, et al. Association of Epstein-Barr virus with leiomyosarcomas in young people with AIDS. N Engl J Med. 1995;332:12-18.
Meijer, et al. Epstein-Barr virus and human T-cell lymphomas. Seminars in Cancer Biology. Aug. 1996;7(4):191-196.
Miller, et al. Antibodies to butyrate-inducible antigens of Kaposi's Sarcoma-associated herpesvirus to patient with HIV-1 infection. The New England J. of Med. 1996;334(20):1292-1297.
Miller, et al. Clinical pharmacology of sodium butyrate in patients with acute leukemia. Eur J Cancer Clin Oncol. 1987;23(9):1283-1287.
Moffat, et al. Discovery of 2-(6-{[(6-fluoroquinolin-2-yl)methyl]amino}bicyclo[3.1.0]hex-3-yl)-N-hydroxypyrimidine-5-carboxamide (CHR-3996), a class I selective orally active histone deacetylase inhibitor.J Med Chem. Dec. 23, 2010;53(24):8663-78. Epub Nov. 16, 2010.
Mottamal et al., Histone deacetylase inhibitors in clinical studies as templates for new anticancer agents. Molecules. 20(3):3898-3941 (2015).
Mueller, et al. Hodgkin's disease and Epstein-Barr virus. Altered antibody pattern before diagnosis. N Engl J Med. 1989;320:689-689.
Murata and Tsurumi, Switching of EBV cycles between latent and lytic states. Reviews in Medical Virology. 24(3):142-153 (2014).
Muro, K. et al. Pembrolizumab for patients with PD-L1-positive advanced gastric cancer (Keynote-012): a multicentre, open-label, phase 1b trial. Lancet Oncology, S1470-2045(26)00175-3 (May 3, 2016).
Nguyen et al., Chemical targeting of the innate antiviral response by histone deacetylase inhibitors renders refractory cancers sensitive to viral oncolysis. Proceedings of the National Academy of Science. 105(39): 14981-14986 (2008).
Niedobitek et al., Epstein-Barr virus gene expression in Hodgkin's disease. Blood. 78(6):1628-1630 (1991).
Niedobitek. The role of Epstein-Barr virus in the pathogenesis of Hodgkin's disease. Annals of Oncology. 7:S11-S17 (1996).
Nudelman, et al. Novel anticancer prodrugs of butyric acid. 2. J Med Chem. Feb. 21, 1992;35(4):687-94.
Osato, et al. Epstein-Barr virus and gastric carcinoma. Semin Cancer Biol. 1996;7:175-182.
Pagano. Epstein-Barr virus: the first human tumor virus and its role in cancer. Proc Assoc Am Physicians. 1999;111:573-580.
Pauken et al., Epigenetic stability of exhausted T cells limits durability of reinvigoration by PD-1 blockade. Science. 354(6316):1160-1165 (2016).
Pender et al., Defective T-cell control of Epstein-Barr virus infection in multiple sclerosis. Clinical & Translational Immunology. 6(1):e126 (2017). doi: 10.1038/cti.2016.87. eCollection Jan. 2017.
Perez, et al. Bryostatin-1 Synergizes with Histone Deacetylase Inhibitors to Reactivate HIV-1 from Latency. Curr HIV Res. Sep. 1, 2010;8(6):418-29.
Perrine, et al. A phase 1,2 trial of arginine butyrate and ganciclovir in patients with Epstein-Barr virus-associated lymphoid malignancies. Blood. 2007;109(6):2571-2578.
Perrine, et al. An Interleukin 2/Sodium Butyrate combination as immunotherapy for rat colon cancer peritoneal carcinomatosis. Gasteroenterology. 1994;107:1697-1708.

(56) References Cited

OTHER PUBLICATIONS

Petrich, et al. Use of class I histone deacetylase inhibitor romidepsin in combination regimens. Leukemia and Lymphoma, 57(8):1755-1765 (Apr. 27, 2016).
Pouillart, et al. Enhancement by stable butyrate derivatives of antitumor and antiviral actions of interferon. Int. J. Cancer. 1992;51:596-601.
Rajan et al., Class I and II Histone Deacetylase Inhibitors Differentially Regulate Thermogenic Gene Expression in Brown Adipocytes. Scientific Reports 8: 13072 (2018).
Reynolds. The Extra Pharmacopoeia, 29th edition, 1989:1359.
Rezvani et al., Engineering Natural Killer Cells for Cancer Immunotherapy. Molecular Therapy 25(8): 1769-1781 (2017).
Rickinson, et al. Epstein-Barr virus. In Fields Virology, vol. 2, 3rd Ed., B. N. Fields, D. M. Knipe, and P. M. Howley, eds. Lippincott-Raven, Philadelphia. 1996:2397-2446.
Riemer et al.: Matching of trastuzumab (Herceptin®) epitope mimics onto the surface of Her-2/neu—a new method of epitope definition. Mol. Immunol. 42:1121-1124 (2005).
Rius, et al. The induction of vimentin gene expression by sodium butyrate in human promonocytic leukemia U937 cells. Experimental Cell Research. 1990;188:129-134.
Rotili, et al. Non-cancer uses of histone deacetylase inhibitors: effects on infectious diseases and beta-hemoglobinopathies. Curr Top Med Chem. 2009;9(3):272-91.
Rowe, et al. Colonic short-chain fatty acids: fuel from the lumen? Gastroenterology. Jul. 1992;103(1):336-8.
Roychowdhury, et al. Selective efficacy of depsipeptide in a xenograft model of Epstein-Barr virus-positive lymphoproliferative disorder. J Natl Cancer Inst. Oct. 6, 2004;96(19):1447-57.
Sachs. Cell differentiation and bypassing of genetic defects in the suppression of malignancy. Cancer Research. 1987;47:1981-1986.
Sadaie, et al. Induction of developmentally programmed cell death and activation of HIV by sodium butyrate. Virology. 1994;202:513-518.
Saito, et al. A synthetic inhibitor of histone deacetuylase, MS-27-275. Proceedings of the National Academy of Sciences USA, Apr. 1999, vol. 96, pp. 4592-4597.
Shen et al., Class I histone deacetylase inhibitor entinostat suppresses regulatory T cells and enhances immunotherapies in renal and prostate cancer models. PLoS One. 7(1):e30815 (2012).
Shen et al., Histone deacetylase inhibitors as immunomodulators in cancer therapeutics. Epigenomics. 8(3):415-428 (2016).
Shibata, et al. Epstein-Barr virus-associated non-Hodgkin's lymphoma in patients infected with the human immunodeficiency virus. Blood. 1993;91:2101-2109.
Slamon, et al. Expression of cellular oncogenes in human malignancies. Science. 1984;224:256-262.
Speck, et al. Infection of breast epithelial cells with Epstein-Barr virus via cell-to-cell contact. J Nat Cancer Inst. 2000;92:1849-1851.
Srivastava et al., Immunomodulatory action of the DNA methyltransferase inhibitor SGI-110 in epithelial ovarian cancer cells and xenografts. Epigenetics. 10(3):237-246 (2015).
Su, et al. Aggressive peripheral T-cell lymphomas containing Epstein-Barr viral DNA: A clinicopathologic and molecular analysis. Blood. 1991;77:799-808.
Swinnen. Overview of posttransplant B-cell lymphoproliferative disorders. Semin Oncol. 1999;26:21-25.
Tang, et al. Memory of butyrate induction by the moloney murine sarcoma virus enhancer-promoter element. Biochem and Biophys Res. Comm. 1992;189(1):141-147.
Toussirot, et al. Epstein-Barr virus in autoimmune diseases. Best Practice & Research Clinical Rheumatology. 2008;22(5): 883-896.
Tsai et al., Interplay between PKCσ and Sp1 on histone deacetylase inhibitor-mediated Epstein-Barr virus reactivation. J Virol. Mar. 2011;85(5):2373-85. Epub Dec. 15, 2010.
U.S. Appl. No. 16/317,750 Final Office Action dated Oct. 29, 2021.
U.S. Appl. No. 16/317,750 Non-Final Office Action dated Jan. 11, 2021.
U.S. Appl. No. 16/317,750 Non-Final Office Action dated Jul. 16, 2021.
U.S. Appl. No. 16/317,750 Non-Final Office Action dated May 27, 2022.
U.S. Appl. No. 16/317,766 Final Office Action dated Dec. 8, 2021.
U.S. Appl. No. 16/317,766 Non-Final Office Action dated Apr. 30, 2021.
U.S. Appl. No. 16/317,766 Non-Final Office Action dated Aug. 26, 2022.
Watson, et al. Butyrate acid in the treatment of cancer. The Lancet. 1933:746-748.
Weiss, et al. Detection of Epstein-Barr virus in Reed-Sternberg cells of Hodgkin's disease. N Engl J Med. 1989;320(8):502-502.
Weiss, et al. Epstein-Barr viral DNA in tissues of Hodgkin's disease. Am J Pathol. 1987;129:86-86.
West et al.: New and emerging HDAC inhibitors for cancer treatment. J. Clin. Invest. 124(1):30-39 (2014).
Williams, et al. Identification of a Ligand for the o-kit Proto-Oncogene. Cell. Oct. 5, 1990;63:167-174.
Woods et al., Abstract 257: Class I HDAC inhibition upregulates PD-1 ligands in melanoma and increases the efficacy of PD-1 blockade. Proceedings: AACR 106th Annual Meeting. Apr. 18, 2015, pp. 1-2; retrieved from https://cancerres.aacrjournals.org/content/75/15_Supplement/257 [retrieved-on Nov. 28, 2019].
Wrangle et al., Alterations of immune response of Non-Small Cell Lung Cancer with Azacytidine. Oncotarget. 4(11):2067-2079 (2013).
Wu, et al. Detection of EBV gene expression in Reed-Sternberg cells of Hodgkin's disease. Int J Cancer. 1990;46:801-801.
Yeivin, et al. Sodium butyrate selectively induces transcription of promoters adjacent to the MoMSV viral enhancer. Gene. Jul. 15, 1992;116(2):159-64.
Zeitlin, et al. Evidence of CFTR function in cystic fibrosis after systemic administration of 4-phenylbutyrate. Mol Ther. Jul. 2002;6(1):119-26.
Zhang, et al. Strategies in developing promising histone deacetylase inhibitors. Med Res Rev. Jul. 2010;30(4):585-602.
Zhang et al., Epigenetic manipulation restores functions of defective CD8+ T cells from chronic viral infection. Molecular Therapy. 22(9):1698-1706 (2014).
Zhu et al., The narrow-spectrum HDAC inhibitor entinostat enhances NKG2D expression without NK cell toxicity, leading to enhanced recognition of cancer cells. Pharmaceutical Research 32(3):779-792 (2015).
Feb. 22, 2022 Non-Final Office Action U.S. Appl. No. 16/961,200.
Akimova, T. et al., "Histone/protein deacetylases and T-cell immune responses", Blood, 2012, vol. 119, No. 11, pp. 2443-2451.
Al-Lazikani et al. Standard conformations for the canonical structures of immunoglobulins. J Mol Biol. 273(4):927-48 (1997).
Altschul et al. Basic local alignment search tool. J Mol Biol 215(3):403-410 (1990).
Bangham, et al.: Diffusion of univalent ions across the lamellae of swollen phospholipids.; J Mol. Biol.; vol. 13:238-252 (1965).
ChemScene Safety Data Sheet for Nanatinostat (Year: 2022).
Cherkassky, L. et al., "Human CAR T cells with cell-instrinsic PD-1 checkpoint blockade resist tumor-mediated inhibition", The Journal of Clinical Investigation, 2016, vol. 126, No. 8, pp. 3130-3144.
Clackson et al.: Making antibody fragments using phage display libraries. Nature 352:624-628 (1991).
Disis et al.: Use of tumour-responsive T cells as cancer treatment. Lancet. 373(9664):673-683 doi:10.1016/S0140-6736(09)60404-9 (2009).
Eckschlager, T. et al., "Histone Deacetylase Inhibitors as Anticancer Drugs", International Journal of Molecular Sciences, 2017, vol. 18, No. 1414, pp. 1-25.
Honegger et al.: Yet another numbering scheme for immunoglobulin variable domains: an automatic modeling and analysis tool. J Mol Biol 309(3):657-70 (2001).
Jooeun et al., Anti-Tumor Activities of XBP1 Antigen-Specific Cytotoxic T Lymphocytes are Enhanced by HDAC6 Inhibitor ACY241. Blood, American Society of Hematology 128(22): 2143 (2016).
June, C. et al., "Engineering lymphocyte subsets: tools, trials and tribulations", Nat Rev Immunol, 2009, vol. 9, No. 10, pp. 704-716.

(56) References Cited

OTHER PUBLICATIONS

Karlin, et al. Applications and statistics for multiple high-scoring segments in molecular sequences. PNAS USA 90:5873-5877 (1993).
Karlin et al. Methods for assessing the statistical significance of molecular sequence features by using general scoring schemes. PNAS USA 87:2264-2268 (1990).
Kindt et al.,. Kuby Immunology, 6th ed., W.H. Freeman and Co., p. 91, (2007).
Kroesen, M. et al., HDAC inhibitors and immunotherapy; a double edged sword?, Oncotarget, 2014 vol. 5, No. 16, pp. 6558-6572.
Lefranc et al.: IMGT unique numbering for immunoglobulin and T cell receptor variable domains and Ig superfamily V-like domains. Dev Comp Immunol 27(1):55-77 (2003).
Li, Y. et al., "HDACs and HDAC Inhibitors in Cancer Development and Therapy", Cold Spring Harbor Perspective in Medicine, 2016; 6; a02631, pp. 1-35.
MacCallum et al.: Antibody-antigen interactions: contact analysis and binding site topography. J Mol Biol. 262(5):732-745 (1996).
Mark, P.A. et al., "Histone Deacetylase Inhibitors: Potential in Cancer Therapy", Journal of Cellular Biochemistry, 2009, vol. 107, pp. 600-608.
Moffat, D. et al., "Discovery of 2-(6-{[(6-Fluoroquinolin-2-yl)methyl]amino}bicyclo[3.1.0]hex-3-yl)-N-hydroxypyrimidine-5-carboxamide (CHR-3996), a Class I Selective Orally Active Histone Ceacetylase Inhibitor", Journal of Medicinal Chemistry, 2010, vol. 53, pp. 8663-8678.
PCT/US2019/013343 International Preliminary Report on Patentability dated Jul. 14, 2020.
PCT/US2019/013343 International Search Report and Written Opinion dated Apr. 10, 2019.
PCT/US2022/037755 International Search Report and Written Opinion dated Dec. 6, 2022.
Pfizer Oncology: CAR-T Cell Therapy Fact Sheet; 2 pages (2017).
Portolano et al., Lack of promiscuity in autoantigen-specific H and L chain combinations as revealed by human H and L chain "roulette". J. Immunol. 150:880-887 (1993).
Shen, L. et al., "Class I Histone Deacetylase Inhibitor Entinostat Suppresses Regulatory T Cells and Enhances Immunotherapies in Renal and Prostate Cancer Models", PLOS One, 2012, vol. 7, No. 1, e30815, pp. 1-14.
Shen, L. et al., "Class I histone deacetylase inhibition is a novel mechanism to target regulatory T cells in immunotherapy", Oncoimmunology, 2012, vol. 1, No. 6, pp. 948-950.
Simon, S. et al., "PD-1 expression on tumor-specific T cells: Friend or foe for immunotherapy?", Oncolmmunology, 2018, vol. 7, No. 1, e1364828, pp. 1-7.
Szoka et al.: Procedure for preparation of liposomes with large internal aqueous space and high capture by reverse-phase evaporation. Proc. Natl. Acad. Sci. 75(9):4194-4198 (1978).
U.S. Appl. No. 16/961,200 Final Office Action dated Jun. 30, 2022.
U.S. Appl. No. 16/961,200 Non-Final Office Action dated Dec. 5, 2022.
Vo et al., Enhanced Antitumor Activity Induced by Adoptive T-Cell Transfer and Adjunctive use of the Histone Deacetylase Inhibitor LAQ824. Cancer Research 69(22): 8693-8699 (2009).
Whitelegg et al. WAM: an improved algorithm for modelling antibodies on the WEB. Protein Eng. 13:819-24 (2000).
Yagita et al., A novel natural killer cell line (KHYG-1) from a patient with aggressive natural killer cell leukemia carrying a p53 point mutation. Leukemia 14: 922-930 (2000).
Fujii et al.: A potential therapy for chordoma via antibody-dependent cell-mediated cytotoxicity employing NK or high-affinity NK cells in combination with cetuximab. J Neurosurg. 128(5):1419-1427. doi:10.3171/2017.1.JNS162610 (2018).
Halkidou et al.: Upregulation and nuclear recruitment of HDAC1 in hormone refractory prostate cancer. Prostate. 59(2):177-189. doi:10.1002/pros.20022 (2004).
Hsieh et al.: Characterization of FcγRIIIA effector cells used in in vitro ADCC bioassay: Comparison of primary NK cells with engineered NK-92 and Jurkat T cells. J Immunol Methods. 441:56-66. doi:10.1016/j.jim.2016.12.002 (2017).
Jochems et al.: ADCC employing an NK cell line (haNK) expressing the high affinity CD16 allele with avelumab, an anti-PD-L1 antibody. Int J Cancer. 141(3):583-593. doi:10.1002/ijc.30767 (2017).
Kaushik et al.: Histone deacetylase inhibitors in castration-resistant prostate cancer: molecular mechanism of action and recent clinical trials. Ther Adv Urol. 2015 7(6):388-395. doi:10.1177/1756287215597637 (2015).
Taylor et al.: FcgammaRIIIa polymorphisms and cetuximab induced cytotoxicity in squamous cell carcinoma of the head and neck. Cancer Immunol Immunother. 58(7):997-1006. doi:10.1007/s00262-008-0613-3 (2009).
Welbsie et al.: Histone deacetylases are required for androgen receptor function in hormone-sensitive and castrate-resistant prostate cancer. Cancer Res. 69(3):958-966. doi:10.1158/0008-5472.CAN-08-2216 (2009).
Alici, Evren. et al. Retroviral Gene Transfer Into Primary Human Natural Killer Cells. Genetic Modification of Hematopoietic Stem Cells: Methods and Protocols 506:127-137 (2009).
Cheng, Min. et al. NK Cell-based Immunotherapy for Malignant Diseases. Cellular & Molecular Immunology 10(3):230-252 (2013).
Co-pending U.S. Appl. No. 19/306,740, inventors Woody; James N. et al., filed Aug. 21, 2025.
Co-pending U.S. Appl. No. 19/320,907, inventor Woody; James N., filed Sep. 5, 2025.
Dahlberg, Carin IM. et al. Natural Killer Cell-based Therapies Targeting Cancer: Possible Strategies to Gain and Sustain Anti-tumor Activity. Frontiers in Immunology 6:605, 1-19 (2015).
Davies, James OJ. et al. Opportunities and Limitations of Natural Killer Cells as Adoptive Therapy for Malignant Disease. Cytotherapy 16(11):1453-1466 (2014). Author Manuscript 1-23.
Dugan, James P. et al. Opportunities to Target the Life Cycle of Epstein-Barr Virus (EBV) in EBV-Associated Lymphoproliferative Disorders. Front Oncol. Mar. 15, 2019:9:127. doi: 10.3389/fonc.2019.00127. eCollection 2019.
EP17828555.7 European Search Report and Opinion dated Mar. 3, 2020.
EP22846572.0 Extended European Search Report dated Apr. 8, 2025.
EP25181509.8 Extended European Search Report dated Sep. 12, 2025.
Kawai et al. Overexpression of Histone Deacetylase HDAC1 Modulates Breast Cancer Progression by Negative Regulation of Estrogen Receptor α. Int. J. Cancer: 107, 353-358 (2003).
Kwok, Gerry et al. Pembrolizumab (Keytruda). Hum Vaccin Immunother. Nov. 2016;12(11):2777-2789. doi: 10.1080/21645515.2016.1199310. Epub Jul. 11, 2016.
Moffat, et al. Supporting Information: Discovery of 2-(6-([(6-fluoroquinolin-2-yl)methyl]amino)bicyclo[3.1.0]hex-3-yl)-N-hydroxypyrimidine-5-carboxamide (CHR-3996), a class I selective orally active histone deacetylase inhibitor. Nov. 2010. Retrieved from the internet: https://pubs.acs.org/doi/suppl/10.1021/jm101177s/suppl_file/jm101177s_si_001.pdf.
U.S. Appl. No. 16/317,766 Office Action dated Apr. 17, 2023.
U.S. Appl. No. 16/317,766 Office Action dated Feb. 28, 2024.
U.S. Appl. No. 16/317,766 Notice of Allowance dated May 21, 2025.
U.S. Appl. No. 16/317,766 Office Action dated Aug. 30, 2024.

* cited by examiner

% CD4+, FoxP3+, CD25+

0.6
0.5
0.4
0.3
0.2
0.1
0

1uM
500 nM
100nM

HISTONE DEACETYLASE INHIBITORS FOR USE IN IMMUNOTHERAPY

CROSS REFERENCE TO RELATED APPLICATION

This application is a continuation of U.S. application Ser. No. 16/317,750, filed Jan. 14, 2019, which is a U.S. National Stage Application of International Application No. PCT/US2017/042199, filed Jul. 14, 2017, which claims the benefit of U.S. Provisional Application Ser. No. 62/362,959 filed on Jul. 15, 2016, all of which are incorporated herein in their entirety.

BACKGROUND OF THE INVENTION

Immunotherapy is an emerging method for the treatment of cancer. Immunotherapy is based upon using constituents of the immune system such as cytokines, chemokines, antibodies, therapeutic vaccines, antigen presenting cells, or T-cells to modulate a patient's immune response and direct it to eliminating a malignancy or tumor. Many immunotherapies require expression of protein, polypeptide, or peptide antigens on the cell surface, in some cases this expression is directly on the surface as is the case with transmembrane and secretory proteins, or in some cases this expression comprises peptides associated with the major histocompatibility molecules (MHC) which serve as antigens for the adaptive immune system.

Many viral infections result in the establishment of a latent infection. Additionally, many cancers are associated with latent viral infections. Latent infections occur when a virus is present, but is not expressing viral proteins such as viral thymidine kinase, protein kinase, and other proteins and polypeptides that may be expressed on the cell surface. Immunotherapies require the presence of viral associated antigens.

SUMMARY OF THE INVENTION

Provided herein are methods for treating a disease in an individual in need thereof comprising administering to the individual a therapeutically effective amount of: (a) an HDAC inhibitor, wherein the HDAC inhibitor comprises (2-(6-{[(6-Fluoroquinolin-2-yl)methyl]amino}-3-azabicyclo[3.1.0]hex-3-yl)-N-hydroxypyrimidine-5-carboxamide); and (b) an immunotherapeutic agent. In certain embodiments, the HDAC inhibitor is administered orally. In certain embodiments, the HDAC inhibitor is administered at a dose of less than 80 mg per day. In certain embodiments, the HDAC inhibitor is administered at a dose of less than 40 mg per day. In certain embodiments, the HDAC inhibitor is administered at a dose of less than 20 mg per day. In certain embodiments, the HDAC inhibitor is administered prior to the administration of the immunotherapeutic agent. In certain embodiments, the HDAC inhibitor is administered during the administration of the immunotherapeutic agent. In certain embodiments, the HDAC inhibitor is administered after the administration of the immunotherapeutic agent. In certain embodiments, the immunotherapeutic agent is a vaccine. In certain embodiments, the vaccine comprises a bacteria or virus encoded polypeptide. In certain embodiments, the immunotherapeutic agent is a cytokine. In certain embodiments, the immunotherapeutic agent is an antibody. In certain embodiments, the antibody is a monoclonal antibody or antigen binding fragment thereof. In certain embodiments, the antibody or antigen binding fragment binds to a checkpoint inhibitor. In certain embodiments, the checkpoint inhibitor comprises one or more of PD-L1, PDL-2, CTLA-4, PD-1, PD-2, TIM-3, VISTA, KIR, IDO, A2AR, B7-H3, B7-H4, BTLA, TIGIT, or CD155. In certain embodiments, the checkpoint inhibitor comprises one or more of PD-1, PD-2 PD-L1, PD-L2, or CTLA-4. In certain embodiments, the antibody or antigen binding fragment comprises nivolumab, pembrolizumab, ipilimumab, pidilizumab, atezolizumab, or a combination thereof. In certain embodiments, the immunotherapeutic agent is cell based. In certain embodiments, the cell based immunotherapeutic agent is a T-cell. In certain embodiments, the T cell is an adoptively transferred T-cell population. In certain embodiments, the T-cell population is autologous. In certain embodiments, the T-cell population is allogeneic. In certain embodiments, the T-cell possesses a chimeric antigen receptor. In certain embodiments, the HDAC inhibitor is incubated with the cell based therapeutic agent in vitro. In certain embodiments, the chimeric antigen receptor is specific for a virus encoded polypeptide. In certain embodiments, the disease is a cancer. In certain embodiments, the cancer is a result of an infection with a virus. In certain embodiments, the virus is from the Herpesviridae family. In certain embodiments, the Herpesviridae family member is Epstein-Barr virus. In certain embodiments, the Herpesviridae family member is cytomegalovirus. In certain embodiments, the Herpesviridae family member is human herpesvirus 8. In certain embodiments, the cancer is a solid tumor. In certain embodiments, the cancer is a leukemia, a lymphoma, a central nervous system lymphoma, Hodgkin's lymphoma, Burkitt's lymphoma, nasopharyngeal carcinoma, mucoepidermoid carcinoma, glioblastoma multiform, breast cancer, Kaposi's sarcoma or gastric carcinoma. In certain embodiments, the disease is a chronic viral infection. In certain embodiments, the chronic viral infection is hepatitis B, hepatitis C, cytomegalovirus, human immunodeficiency virus, human papilloma virus, herpes simplex 1, or herpes simplex 2. In certain embodiments, the disease is a persistent bacterial infection. In certain embodiments, the persistent bacterial is result of infection with *Mycobacterium tuberculosis, Mycobacterium leprae, Helicobacter pylori*, or a *Borrelia* bacteria. In certain embodiments, the HDAC inhibitor increases expression of a checkpoint inhibitor present on T cells. In certain embodiments, checkpoint inhibitor is PD-1. In certain embodiments, the checkpoint inhibitor is CTLA-4. In certain embodiments, the HDAC inhibitor increases expression of a checkpoint inhibitor present on a cancer cell. In certain embodiments, the checkpoint inhibitor is PD-L1. In certain embodiments, the checkpoint inhibitor is PD-L2. In certain embodiments, the method further comprises administering an antiviral agent. In certain embodiments, the antiviral agent comprises valganciclovir. In certain embodiments, the antiviral agent is administered before treatment with a therapeutically effective amount of (2-(6-{[(6-Fluoroquinolin-2-yl)methyl]amino}-3-azabicyclo[3.1.0]hex-3-yl)-N-hydroxypyrimidine-5-carboxamide), and an immunotherapeutic agent. In certain embodiments, administration of the HDACi improves efficacy of the immunotherapy.

Provided herein are methods for treating a cancer in an individual in need thereof comprising administering a therapeutically effective amount of an HDAC inhibitor and an immunotherapeutic agent, wherein the HDAC inhibitor improves the efficacy of the immunotherapeutic agent in the individual. The method for treating a cancer in an individual in need thereof may comprise administering a therapeutically effective amount of: (a) an HDAC inhibitor, wherein the HDAC inhibitor comprises (2-(6-{[(6-Fluoroquinolin-2-yl)methyl]amino}-3-azabicyclo[3.1.0]hex-3-yl)-N-hydroxypyrimidine-5-carboxamide); and (b) an immunotherapeutic agent. In some embodiments, the cancer is a virally-induced malignancy.

In certain embodiments, administration of an HDAC inhibitor induces expression of a viral protein or antigen normally masked, hidden, unexpressed, or silent in a virus infected cell that can be targeted by the immunotherapeutic agent. In certain embodiments, administration of an HDAC inhibitor induces higher expression of a viral protein or antigen normally expressed by a virus infected cell that can be targeted by the immunotherapeutic agent. In certain embodiments, the HDAC inhibitor is Vorinostat/suberoyl anilide hydroxamic acid, JNJ-26481585 (N-hydroxy-2-(4-((((1-methyl-1H-indol-3-yl)methyl)amino)methyl)piperidin-1-yl)pyrimidine-5-carboxamide), R306465/JNJ-16241199 (N-hydroxy-5-(4-(naphthalen-2-ylsulfonyl)piperazin-1-yl)pyrimidine-2-carboxamide), CHR-3996 (2-(6-{[(6-Fluoroquinolin-2-yl)methyl]amino}-3-azabicyclo[3.1.0]hex-3-yl)-N-hydroxypyrimidine-5-carboxamide), Belinostat/PXD101, Panobinostat/LBH-589, trichostatin A/TSA (7-[4-(dimethylamino)phenyl]-N-hydroxy-4,6-dimethyl-7-oxohepta-2,4-dienamide), ITF2357, CBHA, Givinostat/ITF2357, romidepsin, PCI-24781, depsipeptide, butyrate, phenylbutyrate, valproic acid, AN-9, CI-994, Entinostat/MS-275/SNDX-275, mocetinostat/MGCD0103 (N-(2-aminophenyl)-4-((4-pyridin-3-ylpyrimidin-2-ylamino)methyl)benzamide), m-carboxycinnamic acid, bishydroxamic acid, suberic bishydroxamic acid, oxamflatin, ABHA, SB-55629, pyroxamide, propenamides, aroyl pyrrolyl hydroxamides, or LAQ824 (((E)-N-hydroxy-3-[4-[[2-hydroxyethyl-[2-(1H-indol-3-yl)ethyl]amino]methyl]phenyl]prop-2-enamide), chidamide, or 4 SC-202. In certain embodiments, the HDAC inhibitor is administered orally. In certain embodiments, the HDAC inhibitor is administered at a dose of less than 80 mg per day. In certain embodiments, the HDAC inhibitor is administered at a dose of less than 40 mg per day. In certain embodiments, the HDAC inhibitor is administered at a dose of less than 20 mg per day. In certain embodiments, the HDAC inhibitor is administered prior to the administration of the immunotherapeutic agent. In certain embodiments, the HDAC inhibitor is administered during the administration of the immunotherapeutic agent. In certain embodiments, the HDAC inhibitor is administered after the administration of the immunotherapeutic agent.

Provided herein are methods for treating a cancer in an individual in need thereof comprising administering a therapeutically effective amount of an HDAC inhibitor and an immunotherapeutic agent. In certain embodiments, the immunotherapeutic agent is a vaccine. In certain embodiments, the vaccine comprises antigens derived from the Epstein-Barr Virus.

In certain embodiments, the vaccine comprises an antigen presenting cell. In certain embodiments, the antigen presenting cell comprises a dendritic cell, a B cell, or a macrophage. In certain embodiments, the immunotherapeutic agent is a cytokine. In certain embodiments, the immunotherapeutic agent is an antibody. In certain embodiments, the antibody is a monoclonal antibody. In certain embodiments, the antibody or antigen binding fragment binds to a checkpoint inhibitor. In certain embodiments, the checkpoint inhibitor comprises one or more of PD-1, PD-2 PD-L1, PD-L2, or CTLA-4. In certain embodiments, the antibody binds to any one or more of PD-1, PD-2 PD-L1, PD-L2, or anti CTLA-4. In certain embodiments, the antibody is specific for an Epstein-Barr Virus encoded polypeptide. In certain embodiments, the Epstein-Barr Virus encoded polypeptide is LMP-1 or LMP-2.

In certain embodiments, the immunotherapeutic agent is cell based. In certain embodiments, the chimeric antigen receptor is specific for an Epstein-Barr Virus encoded polypeptide. In certain embodiments, the Epstein-Barr Virus encoded polypeptide is LMP-1 or LMP-2. In certain embodiments, the cell based immunotherapeutic agent is a T-cell. In certain embodiments, the T cell is an adoptively transferred T-cell population. In certain embodiments, the T-cell is CD8 positive. In certain embodiments, the T-cell is CD4 positive. In certain embodiments, the T-cell possesses a chimeric antigen receptor. In certain embodiments, the chimeric antigen receptor is specific for an Epstein-Barr Virus encoded polypeptide. In certain embodiments, the Epstein-Barr Virus encoded polypeptide is LMP-1 or LMP-2.

Provided herein is a method for treating a cancer in an individual in need thereof. In certain embodiments, the cancer is a result of a viral infection. In certain embodiments, the viral infection is from the Herpesviridae family. In certain embodiments, the Herpesviridae family member is Epstein-Barr virus. In certain embodiments, the cancer is a leukemia, a lymphoma, a central nervous system lymphoma, Hodgkin's lymphoma, Burkitt's lymphoma, nasopharyngeal carcinoma, or gastric carcinoma. In certain embodiments, the Herpesviridae family member is cytomegalovirus. In certain embodiments, the cancer is a leukemia, a lymphoma, mucoepidermoid carcinoma, glioblastoma multiform, or breast cancer. In certain embodiments, the Herpesviridae family member is human herpesvirus 8. In certain embodiments, the cancer is Kaposi's sarcoma.

In certain embodiments, the HDAC inhibitor decreases expression of a checkpoint inhibitor present on T cells. In certain embodiments, the checkpoint inhibitor is PD-1. In certain embodiments, the checkpoint inhibitor regulator is CTLA-4. In certain embodiments, the HDAC inhibitor decreases expression of a checkpoint inhibitor present on a cancer cell. In certain embodiments, the checkpoint inhibitor is PD-L1. In certain embodiments, the checkpoint inhibitor is PD-L2. In certain embodiments, the HDAC inhibitor is used in conjunction with checkpoint inhibitor antagonist which enables existing immune cells to destroy the cancer. In certain embodiments, the checkpoint inhibitor is PD-L1, PDL-2, CTLA-4, PD-1 or PD-2. In certain embodiments, the checkpoint inhibitor antagonist is an antibody or antibody fragment that specifically binds to PD-L1, PDL-2, CTLA-4, PD-1 or PD-2. In certain embodiments, the checkpoint inhibitor is PD-L1, PDL-2, CTLA-4, PD-1, PD-2, TIM-3, VISTA, KIR, IDO, A2AR, B7-H3, B7-H4, BTLA, TIGIT, or CD155. In certain embodiments, the checkpoint inhibitor antagonist is an antibody or antibody fragment that specifically binds to PD-L1, PDL-2, CTLA-4, PD-1, PD-2, TIM-3, VISTA, KIR, IDO, A2AR, B7-H3, B7-H4, BTLA, TIGIT, or CD155.

In certain embodiments, the HDAC inhibitor increases expression of a checkpoint inhibitor present on T cells. In certain embodiments, the checkpoint inhibitor is PD-1. In certain embodiments, the checkpoint inhibitor is CTLA-4. In certain embodiments, the HDAC inhibitor increases expression of a checkpoint inhibitor present on a cancer cell. In certain embodiments, the checkpoint inhibitor is PD-L1. In certain embodiments, the checkpoint inhibitor is PD-L2. In certain embodiments, the HDAC inhibitor is used in conjunction with a checkpoint inhibitor antagonist. In certain embodiments, the checkpoint inhibitor is PD-L1, PDL-2, CTLA-4, PD-1 or PD-2. In certain embodiments, the checkpoint inhibitor antagonist is an antibody or antibody fragment that specifically binds to PD-L1, PDL-2, CTLA-4, PD-1 or PD-2. In certain embodiments, the checkpoint inhibitor is PD-L1, PDL-2, CTLA-4, PD-1, PD-2, TIM-3, VISTA, KIR, IDO, A2AR, B7-H3, B7-H4, BTLA, TIGIT, or CD155. In certain embodiments, the checkpoint inhibitor antagonist is an antibody or antibody fragment that specifically binds to PD-L1, PDL-2, CTLA-4, PD-1, PD-2, TIM-3, VISTA, KIR, IDO, A2AR, B7-H3, B7-H4, BTLA, TIGIT, or CD155.

In certain embodiments, the method further comprises administering an antiviral. In certain embodiments, the antiviral comprises valganciclovir. In certain embodiments, the antiviral is administered before treatment of a therapeutically effective amount of (2-(6-{[(6-Fluoroquinolin-2-yl) methyl]amino}-3-azabicyclo[3.1.0]hex-3-yl)-N-hydroxypyrimidine-5-carboxamide), and an immunotherapeutic agent.

Also provided herein is a method for method for treating a disease in an individual in need thereof comprising administering to the individual a therapeutically effective amount of: (a) an HDAC inhibitor, wherein the HDAC inhibitor comprises (2-(6-{[(6-Fluoroquinolin-2-yl)methyl]amino}-3-azabicyclo[3.1.0]hex-3-yl)-N-hydroxypyrimidine-5-carboxamide); and (b) an antibody or antigen binding fragment thereof which specifically binds and antagonizes a checkpoint inhibitor. In certain embodiments, the checkpoint inhibitor comprises one or more of PD-1, PD-2 PD-L1, PD-L2, or CTLA-4. In certain embodiments, the antibody or antigen binding fragment comprises nivolumab, pembrolizumab, ipilimumab, pidilizumab, atezolizumab, or a combination thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features described herein are set forthwith particularity in the appended claims. A better understanding of the features and advantages of the features described herein will be obtained by reference to the following detailed description that sets forth illustrative examples, in which the principles of the features described herein are utilized, and the accompanying drawings of which:

FIG. 1A shows quantified FACs data (percentage CD4+, CD25+, FoxP3+) from BALB/c splenocytes treated with Entinostat (1 μM) or VRx-3996 (1 μM, 500 nM, 100 nM, 1 nM). FIG. 1B shows quantified FACs data from BALB/c splenocytes treated with VRx-3996 at 1 μM, 500 nM, 100 nM.

FIG. 2A shows mice treated with 10 mg/kg of VRx-3996 and 10 mg/kg anti-PD-1 (filled shapes). FIG. 2B shows mice treated with 25 mg/kg of VRx-3996 and 10 mg/kg anti-PD-1 (filled shapes).

FIG. 3A shows mice treated with 10 mg/kg of VRx-3996 and 10 mg/kg anti-PD-1 (filled shapes) FIG. 3B shows mice treated with 25 mg/kg of VRx-3996 and 10 mg/kg anti-PD-1 (filled shapes).

DETAILED DESCRIPTION OF THE INVENTION

Figures 1A, 1B:
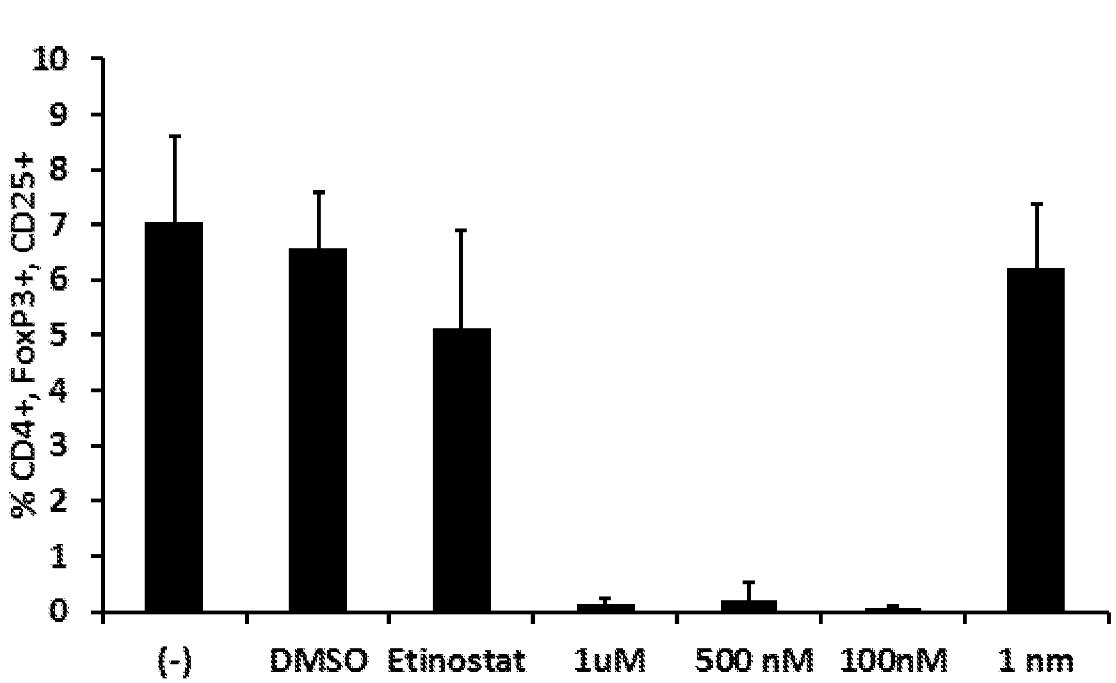
FIGS. 1A-B.

Provided herein are methods and compositions for treating and/or preventing a disease in an individual in need thereof. In certain embodiments, the disease is a cancer. In certain embodiments, the disease is associated with a latent viral infection or persistent bacterial infection. In certain embodiments, the disease associated with a latent viral infection or persistent bacterial infection is a cancer. In certain embodiments, the treatment can comprise the steps of administering a therapeutically effective amount of an HDAC inhibitor and an immunotherapy to the subject. In certain embodiments, the methods include the administration of an HDAC inhibitor before the initiation of immunotherapy. In certain embodiments, the methods include the co-administration of an HDAC inhibitor and immunotherapy. In certain embodiments, the methods include of an HDAC inhibitor after the initiation of immunotherapy.

Provided herein are methods and compositions for treating and/or preventing cancer in an individual in need thereof. In certain embodiments, the cancer is associated with a latent viral infection. In certain embodiments, the treatment can comprise the steps of administering a therapeutically effective amount of an HDAC inhibitor and an immunotherapy to the subject. In certain embodiments, the methods include the administration of an HDAC inhibitor before the initiation of immunotherapy. In certain embodiments, the methods include the co-administration of an HDAC inhibitor and immunotherapy. In certain embodiments, the methods include of an HDAC inhibitor after the initiation of immunotherapy.

Provided herein are methods for treating a virally-induced malignancy in an individual in need thereof comprising administering a therapeutically effective amount of an HDAC inhibitor and an immunotherapeutic agent, wherein the HDAC inhibitor improves the efficacy of the immunotherapeutic agent in the individual. In certain embodiments, administration of the HDAC inhibitor induces expression of a viral protein or antigen normally masked, hidden, unexpressed, or silent in a virus infected cell, wherein the viral protein or antigen can be targeted by the immunotherapeutic agent.

The methods and compositions provided can be used to treat and/or prevent any of the cancers disclosed herein. Any of the HDAC inhibitors and/or immunotherapies described herein can be used in the methods and compositions of the provided invention.

Another aspect of the present invention relates to formulations, routes of administration, and effective doses for pharmaceutical compositions comprising an agent or combination of agents, e.g., an HDACi and an immunotherapy. An HDACi, an immunotherapy, or one or more additional agents can be administered to a subject in separate pharmaceutical compositions or can be co-formulated in a single pharmaceutical composition.

Also provided are methods relating to dosing schedules for an HDACi and an immunotherapy. One or more pharmaceutical compositions can be administered to a subject by "pulsed administration" over a period of time.

Overview

Herpesviridae is a large family of DNA viruses that causes disease in humans. The members of this family are also known as herpesviruses. Viruses in this family include Herpes simplex virus (HSV) 1 and 2; cytomegalovirus (CMV); Epstein-Barr virus (EBV); and Human herpes virus (HHV) 6, 7, and 8. HHV-8 is also known as Kaposi's sarcoma-associated herpesvirus.

Upon infection with a herpesvirus viral DNA is transcribed into RNA in the cell nucleus. Infection then proceeds via two different stages; a lytic stage and a latent stage. During lytic replication viral replication often leads to cell death and the emergence of symptoms which can include fever, headache, sore throat, rash, and, with some viruses, the emergence of sores.

Lytic genes fall into expression categories depending upon when after cell entry they are expressed: immediate early, early, and late. Immediate early gene products include; the EBV genes BZLF1 and BRLF1; the HSV genes RS1/ICP4, ICP0, UL 54/ICP27, US1/ICP22, US12/ICP47; and the CMV genes pp71, IE1, and IE2. Early gene products include; the EBV gene BNLF2; and the HSV genes UL5, UL8, UL29, UL30, UL42, UL52, and ICP8. Late gene products include structural components such as the EBV gene VCA and the HSV genes UL31 and UL34. Herpesviruses are also known for their ability to establish latent infection. During latent infection, viral replication is minimal or non-existent and patients are often non-symptomatic. During latent viral infection many gene transcripts and viral proteins are not expressed or are expressed at low levels. Examples of genes associated with latency are; the EBV genes EBNA-1, EBNA-2, EBNA-3A, EBNA-3B, EBNA-3C, EBNA-LP, LMP-1, LMP-2A, LMP-2B, and EBER; the HSV gene latency associate transcript (LAT); and the CMV genes US28 and anti-sense UL81-82. Provided herein are methods to induce expression of gene products from a herpesvirus to increase the efficacy of immunotherapy of various herpes virus associated cancers.

Many herpesviruses are associated with cancer. EBV is associated with nasopharyngeal cancer (cancer of the area in the back of the nose), leukemia, lymphoma, lymphomas such as Burkitt's lymphoma or Hodgkin's lymphoma, and stomach cancer. HHV-8 is associated with Kaposi's sarcoma. CMV is associated with cancer of the salivary glands and mucoepidermoid carcinoma.

For example, previous studies using patient-derived cells in vitro, and also from phase I/II clinical studies on a series of patients with EBV-associated lymphomas, have clearly shown the great promise of this combination therapy approach. Strong epidemiological association of Epstein-Barr Virus (EBV) with various human lymphoid malignancies and in vitro studies demonstrating tumorigenic activity of many EBV latent gene products suggest a causal relationship between EBV and these diseases. However, as EBV maintains a latent state of infection in these lymphomas, typical anti-herpes viral drugs, such as the nucleoside analogs ganciclovir (GCV) or acyclovir, are ineffective as these pro-drugs require expression of a lytic phase EBV protein, thymidine kinase (TK) or protein kinase (EBV-PK), for their activity. Therefore, selective induction of EBV lytic-phase gene expression in lymphoma cells that harbor latent EBV, coupled with simultaneous exposure to antiviral drugs, has been advanced as promising targeted therapy, because of resulting targeting of cytotoxicity to the EBV-infected tumor cells.

A variety of agents, including short-chain fatty acids and chemotherapeutic drugs, have been used to induce EBV lytic-phase infection in cultured cells, but these in vitro studies have generally not resulted in clinical application. For instance, arginine butyrate and GCV has successfully been used to treat EBV-positive lymphoid malignancies in a recent Phase I/II clinical trial. In this study of 15 patients with relapsed or refractory EBV-positive lymphoid tumors, 4 patients achieved complete tumor remissions and 6 patients partial tumor remissions. However, the rapid metabolism of butyrate requires continuous IV administration of high doses. Butyrate has pan-HDAC inhibitory activity, and it has been established that this activity is responsible for the induction of the EBV-TK protein. HDAC inhibitors have been shown to induce both EBV-TK and EBV-PK in EBV infected tumors.

Many other viruses establish latency after lytic infection. Human immunodeficiency virus (HIV) and Human T lymphotrophic virus (HTLV) are two examples of retroviruses with relevance to human disease. HIV expresses several genes gag, pol, env, tat, rev, nef, vpr, vif and vpu, which are required for its lytic replication. Provided herein, are methods to induce expression of gene products from a retrovirus to increase the efficacy of immunotherapy of various retrovirus associated cancers and diseases. Human papilloma virus (HPV) infects epithelial cells and is a leading cause of cervical, genital, head, and neck cancers. Hepatitis B and C infect the liver and chronic infection leads to hepatocellular carcinoma. Provided herein are methods to induce expression of gene products from HPV and hepatitis viruses to increase the efficacy of immunotherapy of cancers associated with these viruses.

Immunotherapeutics such as cytokine treatment, monoclonal antibodies, and vaccines are ideal candidates to treat cancers and chronic infections that occur as a result of viral infection. Chimeric antigen receptor T cells (CAR T cells) represent novel cell based therapeutics with the potential to treat cancer and persistent viral infections. CAR T cells comprising a transgenic targeting receptor, in many cases derived from an antibody molecule, allow for T cells to kill a target cell without the traditional need for peptide presented in an MHC context. In the case of virus infected cells, this is especially important as many viruses including herpesviruses and retroviruses evade the immune response by interfering with classical antigen presentation.

Methods and Compositions

In one aspect, provided herein are methods for treating and/or preventing a cancer, a virally-induced cancer, or virally associated cancer. In some embodiments, the cancer is associated with a latent viral infection. In certain embodiments, the methods comprise administering an HDAC inhibitor (HDACi) and an immunotherapy. In certain embodiments, the HDACi and the immunotherapy are co-formulated. In some embodiments, the methods comprise further administering an additional HDACi. In other embodiments, the methods comprise further administering an additional immunotherapy. In some embodiments, the methods comprise administering additional individual doses of the HDACi. In certain aspects the methods comprise administering an HDACi and a thymidine kinase inhibitor such as valganciclovir or acyclovir prior to treatment of the cancer with HDACi and an immunotherapeutic. This pretreatment can serve to reduce a tumor or debulk a tumor prior to administration of immunotherapy.

In one aspect, provided herein are methods for treating and/or preventing a chronic viral infection or a persistent bacterial infection. In certain embodiments, the methods comprise administering an HDAC inhibitor (HDACi) and an immunotherapy. In certain embodiments, the HDACi and the immunotherapy are co-formulated. In some embodiments, the methods comprise further administering an additional HDACi. In other embodiments, the methods comprise further administering an additional immunotherapy. In some embodiments, the methods comprise administering additional individual doses of the HDACi.

Definitions

The term"about," as used herein, refers to a number within 1%, 5%, or 10% of the stated amount.

The terms "viral," "virus-associated," and "virally-induced," with reference to disorders, are used interchangeably throughout the instant specification.

The terms "comprises" and "comprising" are intended to have the broad meaning ascribed to them and can mean "includes," "including," and the like.

The term "subject," "patient," or "individual" are used interchangeably herein and refer to a human individual suffering from a disorder described herein.

The terms "treat," "treating," or "treatment," and other grammatical equivalents as used herein, include alleviating, inhibiting, or reducing symptoms, reducing or inhibiting severity of, reducing incidence of, prophylactic treatment of, reducing or inhibiting recurrence of, delaying onset of, delaying recurrence of, abating or ameliorating a disease or condition symptoms, ameliorating the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition. The terms further include achieving a therapeutic benefit. By therapeutic benefit is meant eradication or amelioration of the underlying disorder being treated, and/or the eradication or amelioration of one or more of the physiological symptoms associated with the underlying disorder such that an improvement is observed in the patient.

The terms "prevent," "preventing" or "prevention," and other grammatical equivalents as used herein, include preventing additional symptoms, preventing the underlying metabolic causes of symptoms, inhibiting the disease or condition, e.g., arresting the development of the disease or condition and are intended to include prophylaxis. The terms further include achieving a prophylactic benefit. For prophylactic benefit, the compositions are optionally administered to a patient at risk of developing a particular disease, to a patient reporting one or more of the physiological symptoms of a disease, or to a patient at risk of reoccurrence of the disease.

The terms "effective amount" or "therapeutically effective amount" as used herein, refer to a sufficient amount of at least one agent being administered which achieve a desired result, e.g., to relieve to some extent one or more symptoms of a disease or condition being treated. In certain instances, the result is a reduction and/or alleviation of the signs, symptoms, or causes of a disease, or any other desired alteration of a biological system. In certain instances, an "effective amount" for therapeutic uses is the amount of the composition comprising an agent as set forth herein required to provide a clinically significant decrease in a disease. An appropriate "effective" amount in any individual case is determined using any suitable technique, such as a dose escalation study.

The terms "administer," "administering", "administration," and the like, as used herein, refer to the methods that are used to enable delivery of agents or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Administration techniques that in some instances are employed with the agents and methods described herein include, e.g., as discussed in Goodman and Gilman, *The Pharmacological Basis of Therapeutics* (current edition), Pergamon; and Remington's, *Pharmaceutical Sciences* (current edition), Mack Publishing Co., Easton, Pa. In certain embodiments, the agents and compositions described herein are administered orally. In some embodiments, the compositions described herein are administered parenterally.

The term "antibody" herein is used in the broadest sense and includes polyclonal and monoclonal antibodies, including intact antibodies and functional (antigen-binding) antibody fragments thereof, including fragment antigen binding (Fab) fragments, F(ab')2 fragments, Fab' fragments, Fv fragments, recombinant IgG (rIgG) fragments, single chain antibody fragments, including single chain variable fragments (sFv or scFv), and single domain antibodies (e.g., sdAb, sdFv, nanobody) fragments. The term encompasses genetically engineered and/or otherwise modified forms of immunoglobulins, such as intrabodies, peptibodies, chimeric antibodies, fully human antibodies, humanized antibodies, and heteroconjugate antibodies, multispecific, e.g., bispecific, antibodies, diabodies, triabodies, and tetrabodies, tandem di-scFv, tandem tri-scFv. Unless otherwise stated, the term "antibody" should be understood to encompass functional antibody fragments thereof. The term also encompasses intact or full-length antibodies, including antibodies of any class or sub-class, including IgG and subclasses thereof, IgM, IgE, IgA, and IgD.

Among the provided antibodies useful for inclusion in the immunoconjugates described herein, are monoclonal antibodies, polyclonal antibodies, multispecific antibodies (for example, bispecific antibodies and polyreactive antibodies), and antibody fragments. The antibodies include antibody-conjugates and molecules comprising the antibodies, such as chimeric molecules. Thus, an antibody includes, but is not limited to, full-length and native antibodies, as well as fragments and portions thereof retaining the binding specificities thereof, such as any specific binding portion thereof including those having any number of, immunoglobulin classes and/or isotypes (e.g., IgG1, IgG2, IgG3, IgG4, IgM, IgA, IgD, IgE and IgM); and biologically relevant (antigen-binding) fragments or specific binding portions thereof, including but not limited to Fab, F(ab')2, Fv, and scFv (single chain or related entity). A monoclonal antibody is generally one within a composition of substantially homogeneous antibodies; thus, any individual antibodies comprised within the monoclonal antibody composition are identical except for possible naturally occurring mutations that may be present in minor amounts. A polyclonal antibody is a preparation that includes different antibodies of varying sequences that generally are directed against two or more different determinants (epitopes).

The invention can be understood more fully by reference to the following detailed description and illustrative examples, which are intended to exemplify non-limiting embodiments of the invention.

HDAC Inhibitors

The methods of the provided invention comprise use of one or more pharmaceutical compositions provided herein comprising an HDAC inhibitor (HDACi). In a certain embodiment, the HDACi induces expression of a gene product in a virus-infected cell. In other aspects the HDACi alters gene expression in a target cell or tissue allowing it to be killed by an immunotherapy. The gene product expressed can be a viral enzyme or a cellular enzyme or activity that is largely expressed in virus-infected cells. Expression products that can be targeted include enzymes involved with DNA replication, for example, for repair or replication of the genome, assembly of complete virus particles, generation of viral membrane or walls, RNA transcription or protein translation, or combinations of these activities. Interference with these processes can be performed by inducing and then acting on an enzyme and, preferably, a critical enzyme in the process. Inducing agents that can be used in the methods and compositions of the provided invention are described, for example, in U.S. Pat. Nos. 6,197,743 and 6,677,302, which are herein incorporated by reference in their entireties.

HDAC inhibitors according to the methods or compositions provided herein include, without limitation, short-chain fatty acid (SCFA) derivatives, hydroxamic acids, cyclic peptides, aliphatic acids, depsipeptides, and benzamides.

In some embodiments, the HDACi is an SCFA derivative. Examples of SCFA inducing agents include propionic acid, butyric acid, succinic acid, valproic acid, fumaric acid monoethyl ester, dimethyl butyric acid, trifluorobutanol, chloropropionic acid, isopropionic acid, 2-oxypentanoic acid, 2,2- or 3,3-dimethyl butyric acid, 2,2- or 3,3-diethyl butyric acid, butyric acid ethyl ester, 2-methyl butanoic acid, fumaric acid, and amides and salts thereof. Other examples include methoxy acetic acid, methoxy propionic acid, N-acetylglycine, mercaptoacetic acid, 1- or 2-methyl cyclopropane carboxylic acid, squaric acid, 2- or 3-phenoxy propionic acid, methoxy butyric acid, phenoxy acetic acid, 2- or 3-phenoxy butyric acid, phenyl acetic acid, phenyl propionic acid, 3-phenyl butyric acid, ethyl-phenyl acetic acid, 4-chloro-2-phenoxy-2-propionic acid, n-dimethyl butyric acid glycine amide, o-benzoyl lactic acid, o-dimethyl butyric acid lactate, cinnamic acid, dihydrocinnamic acid ($C_6H_5CHCH_3COOH$), alpha-methyl-dihydrocinnamic acid, thiophenoxy acetic acid, and amines, amides, and salts of these chemicals. Useful amines and amides can include isobutylhydroxylamine, fumaric acid monoamide, fumaramide, succinamide, or isobutyramide.

In some embodiments, the HDAC inhibitor is a hydroxamic acid, for example, Vorinostat/suberoyl anilide hydroxamic acid (SAHA), bishyroxamic acid/CBHA, Droxinostat, Quisinostat/JNJ-26481585, R306465/JNJ-16241199, CHR-3996, Belinostat/PXD101, Panobinostat/LBH-589, trichostatin A/TSA, ITF2357, m-carboxycinnamic acid, Givinostat/ITF2357, Pracinostat/SB939, Resminostat/4SC-201, Dacinostat/LAQ824, Abexinostat/PCI-24781, PCYC-0402, PCYC-0403, A161906, SB-55629, AR42, CUDC-101, Scriptaid, oxamflatin, and tubacin. In certain embodiments, the HDAC inhibitor is a pyrimidine hydroxamic acid, for example, JNJ-26481585, JNJ-16241199, or CHR-3996.

In some embodiments, the HDAC inhibitor is a hydroxamic acid derivative. In certain embodiments, the HDAC inhibitor is a pyrimidine hydroxamic acid. In some embodiments, the HDAC inhibitor is a non-piperidine-containing pyrimidine hydroxamic acid derivative. In certain embodiments, the HDAC inhibitor comprises an azabicyclo-hexane. In other embodiments, the HDAC inhibitor comprises fluorine. In certain embodiments, the HDAC inhibitor comprises a fluoroquinoline group.

In some embodiments, the HDAC inhibitor is a cyclic peptide. In certain embodiments, the cyclic peptide is HC-toxin, apcidin, Trapoxin A, Trapoxin B, WF-3161, chlamydocin, or azumamide A.

In some embodiments, the HDAC inhibitor is a depsipeptide. In certain embodiments, the depsipeptide is romidepsin (FK228), romidepsin analogs and derivatives, largazole, largazole analogs and derivatives, diheteropeptin, FR901375, or spiruchostatins.

In some embodiments, the HDAC inhibitor is a benzamide. In certain embodiments, the benzamide is Etinostat/MS275, RG-2833, CI994, 4SC-202, Mocetinostat/MGCD0103, RG2833, CDUC-101, or chidamide.

In some embodiments, the HDAC inhibitor is ACY-822, ACY-957, ACY-1071, ACY-1112, or ACY-1215.

In some embodiments, a viral inducing agent, for example an HDAC inhibitor, penetrates the blood brain barrier. In certain embodiments, a viral inducing agent that penetrates the blood brain barrier comprises arginine butyrate, SAHA, chidamide, 4SC-202, or CHR-3996.

In a certain embodiment, the HDAC inhibitor targets a specific HDAC or class of HDAC. In certain embodiments, the HDAC inhibitor inhibits any one or more of a Class I, Class IIA, Class II B, Class III, or a Class IV HDAC. In certain embodiments, the HDAC inhibitor inhibits a Class I HDAC. In certain embodiments, the HDAC inhibitor inhibits any one or more of a HDAC1, HDAC2, HDAC3, HDAC4, HDAC5, HDAC6, HDAC7, HDAC8, HDAC9, HDAC10, or HDAC11. In certain embodiments, the HDAC inhibitor inhibits any one or more of a HDAC1, HDAC2, HDAC3 or, HDAC8.

In certain embodiments, the HDAC inhibitor is administered at a dose of less than 400 mg/day. In some embodiments, the HDAC inhibitor is administered at a dose of about 1 mg/day, about 2 mg/day, about 5 mg/day, about 10 mg/day, about 15 mg/day, about 20 mg/day, about 25 mg/day, about 30 mg/day, about 35 mg/day, about 40 mg/day, about 45 mg/day, about 50 mg/day, about 60 mg/day, about 70 mg/day, about 80 mg/day, about 90 mg/day, about 100 mg/day, about 120 mg/day, about 125 mg/day, about 140 mg/day, about 150 mg/day, about 160 mg/day, about 175 mg/day, about 180 mg/day, about 190 mg/day, about 200 mg/day, about 225 mg/day, about 250 mg/day, about 275 mg/day, about 300 mg/day, about 325 mg/day, about 350 mg/day, about 375 mg/day, about 400 mg/day, about 425 mg/day, about 450 mg/day, about 475 mg/day, or about 500 mg/day. In certain embodiments, the HDAC inhibitor is administered at a dose of less than 1 mg/day, less than 2 mg/day, less than 5 mg/day, less than 10 mg/day, less than 15 mg/day, less than 20 mg/day, less than 25 mg/day, less than 30 mg/day, less than 35 mg/day, less than 40 mg/day, less than 45 mg/day, less than 50 mg/day, less than 60 mg/day, less than 70 mg/day, less than 80 mg/day, less than 90 mg/day, less than 100 mg/day, less than 120 mg/day, less than 125 mg/day, less than 140 mg/day, less than 150 mg/day, less than 160 mg/day, less than 175 mg/day, less than 180 mg/day, less than 190 mg/day, less than 200 mg/day, less than 225 mg/day, less than 250 mg/day, less than 275 mg/day, less than 300 mg/day, less than 325 mg/day, less than 350 mg/day, less than 375 mg/day, less than 400 mg/day, less than 425 mg/day, less than 450 mg/day, less than 475 mg/day, or less than 500 mg/day. In some embodiments, the HDAC inhibitor is administered at a dose of more than 1 mg/day, more than 2 mg/day, more than 5 mg/day, more than 10 mg/day, more than 15 mg/day, more than 20 mg/day, more than 25 mg/day, more than 30 mg/day, more than 35 mg/day, more than 40 mg/day, more than 45 mg/day, more than 50 mg/day, more than 60 mg/day, more than 70 mg/day, more than 80 mg/day, more than 90 mg/day, more than 100 mg/day, more than 120 mg/day, more than 125 mg/day, more than 140 mg/day, more than 150 mg/day, more than 160 mg/day, more than 175 mg/day, more than 180 mg/day, more than 190 mg/day, more than 200 mg/day, more than 225 mg/day, more than 250 mg/day, more than 275 mg/day, more than 300 mg/day, more than 325 mg/day, more than 350 mg/day, more than 375 mg/day, more than 400 mg/day, more than 425 mg/day, more than 450 mg/day, more than 475 mg/day, or more than 500 mg/day. In certain embodiments, the HDAC inhibitor is administered at a dose of more than 1 mg/day and less than 500 mg/day. In some embodiments, the HDAC inhibitor is administered at a dose of more than 20 mg/day and less than 80 mg/day. In certain embodiments, the HDAC inhibitor is administered once a day (q.d.), twice a day (b.i.d.), or thrice a day (t.i.d.). In some embodiments, the HDAC inhibitor is administered daily, once a week, twice a week, three times a week, four times a week, or five times a week.

In some embodiments, the HDAC inhibitor is ACY-957. In certain embodiments, ACY-957 is administered at a dose of 200 mg/day. In some embodiments, ACY-957 is administered at a dose of about 1 mg/day, about 2 mg/day, about 5 mg/day, about 10 mg/day, about 15 mg/day, about 20 mg/day, about 25 mg/day, about 30 mg/day, about 35 mg/day, about 40 mg/day, about 45 mg/day, about 50 mg/day, about 60 mg/day, about 70 mg/day, about 80 mg/day, about 90 mg/day, about 100 mg/day, about 150 mg/day, about 200 mg/day, about 250 mg/day, about 300 mg/day, about 350 mg/day about 400 mg/day, about 450 mg/day, or about 500 mg/day. In certain embodiments, 4SC-202 is administered at a dose of less than 1 mg/day, less than 2 mg/day, less than 5 mg/day, less than 10 mg/day, less than 15 mg/day, less than 20 mg/day, less than 25 mg/day, less than 30 mg/day, less than 35 mg/day, less than 40 mg/day, less than 45 mg/day, less than 50 mg/day, less than 60 mg/day, less than 70 mg/day, less than 80 mg/day, less than 90 mg/day, or less than 100 mg/day, less than 150 mg/day, less than 200 mg/day, less than 250 mg/day, less than 300 mg/day, less than 350 mg/day less than 400 mg/day, less than 450 mg/day, or less than 500 mg/day. In some embodiments, ACY-957 is administered at a dose of more than 1 mg/day, more than 2 mg/day, more than 5 mg/day, more than 10 mg/day, more than 15 mg/day, more than 20 mg/day, more than 25 mg/day, more than 30 mg/day, more than 35 mg/day, more than 40 mg/day, more than 45 mg/day, more than 50 mg/day, more than 60 mg/day, more than 70 mg/day, more than 80 mg/day, more than 90 mg/day, more than 100 mg/day, more than 150 mg/day, more than 200 mg/day, more than 250 mg/day, more than 300 mg/day, more than 350 mg/day more than 400 mg/day, more than 450 mg/day, or more than 500 mg/day. In some embodiments, ACY-957 is administered at a dose of about 10 mg/day to about 1000 mg/day. In certain embodiments, ACY-957 is administered at a dose of about 20 mg/day to about 800 mg/day. In some embodiments, ACY-957 is administered at a dose of about 25 mg/day to about 600 mg/day. In certain embodiments, ACY-957 is administered once a day (q.d.), twice a day (b.i.d.), or thrice a day (t.i.d.). In some embodiments, the dose is about 50 mg twice daily. In some embodiments, the dose is about 100 mg twice daily. In some embodiments, the dose is about 150 mg twice daily. In some embodiments, the dose is about 200 mg twice daily. In some embodiments, the dose is about 250 mg twice daily. In some embodiments, the dose is about 300 mg twice daily. In some embodiments, ACY-957 is administered daily, once a week, twice a week, three times a week, four times a week, or five times a week. In some embodiments, ACY-957 is administered once a month, twice a month, thrice a month, or 4 times a month. In certain embodiments, ACY-957 is in a delayed, slow, or timed release form.

In some embodiments, a unit dose of a co-formulated HDAC inhibitor ACY-957 and antiviral agent comprises less than 400 mg of the HDAC inhibitor ACY-957 and less than 1000 mg of the antiviral agent. In some embodiments, a unit dose of a co-formulated HDAC inhibitor ACY-957 and antiviral agent comprises less than 200 mg of the HDAC inhibitor ACY-957 and less than 1000 mg of the antiviral agent. In certain embodiments, the unit dose comprises less than 50 mg of the HDAC inhibitor ACY-957 and less than 500 mg of the antiviral agent. In other embodiments, the unit dose comprises less than 80 mg of the HDAC inhibitor ACY-957 and less than 1500 mg of the antiviral agent. In some embodiments, the unit dose comprises less than 50 mg of the HDAC inhibitor ACY-957 and less than 1000 mg of antiviral agent. In some embodiments, the unit dose comprises about 20 mg of the HDAC inhibitor ACY-957 and about 450 mg of antiviral agent. In certain embodiments, the unit dose comprises about 40 mg of the HDAC inhibitor ACY-957 and about 900 mg of antiviral agent. In some embodiments, the antiviral agent is formulated as controlled release, delayed release, or slow release.

In some embodiments, the HDAC inhibitor is ACY-1215. In certain embodiments, ACY-1215 is administered at a dose of 200 mg/day. In some embodiments, ACY-1215 is administered at a dose of about 1 mg/day, about 2 mg/day, about 5 mg/day, about 10 mg/day, about 15 mg/day, about 20 mg/day, about 25 mg/day, about 30 mg/day, about 35 mg/day, about 40 mg/day, about 45 mg/day, about 50 mg/day, about 60 mg/day, about 70 mg/day, about 80 mg/day, about 90 mg/day, about 100 mg/day, about 150 mg/day, about 160 mg/day, about 170 mg/day, about 200 mg/day, about 250 mg/day, about 300 mg/day, about 350 mg/day about 400 mg/day, about 450 mg/day, or about 500 mg/day. In certain embodiments, 4SC-202 is administered at a dose of less than 1 mg/day, less than 2 mg/day, less than 5 mg/day, less than 10 mg/day, less than 15 mg/day, less than 20 mg/day, less than 25 mg/day, less than 30 mg/day, less than 35 mg/day, less than 40 mg/day, less than 45 mg/day, less than 50 mg/day, less than 60 mg/day, less than 70 mg/day, less than 80 mg/day, less than 90 mg/day, or less than 100 mg/day, less than 150 mg/day, less than 200 mg/day, less than 250 mg/day, less than 300 mg/day, less than 350 mg/day less than 400 mg/day, less than 450 mg/day, or less than 500 mg/day. In some embodiments, ACY-1215 is administered at a dose of more than 1 mg/day, more than 2 mg/day, more than 5 mg/day, more than 10 mg/day, more than 15 mg/day, more than 20 mg/day, more than 25 mg/day, more than 30 mg/day, more than 35 mg/day, more than 40 mg/day, more than 45 mg/day, more than 50 mg/day, more than 60 mg/day, more than 70 mg/day, more than 80 mg/day, more than 90 mg/day, more than 100 mg/day, more than 150 mg/day, more than 200 mg/day, more than 250 mg/day, more than 300 mg/day, more than 350 mg/day more than 400 mg/day, more than 450 mg/day, or more than 500 mg/day. In some embodiments, ACY-1215 is administered at a dose of about 10 mg/day to about 1000 mg/day. In certain embodiments, ACY-1215 is administered at a dose of about 20 mg/day to about 800 mg/day. In some embodiments, ACY-1215 is administered at a dose of about 25 mg/day to about 600 mg/day. In some embodiments, ACY-1215 is administered at a dose of about 50 mg/day to about 400 mg/day. In some embodiments, ACY-1215 is administered at a dose of about 100 mg/day to about 300 mg/day. In some embodiments, ACY-1215 is administered at a dose of about 100 mg/day to about 200 mg/day. In certain embodiments, ACY-1215 is administered once a day (q.d.), twice a day (b.i.d.), or thrice a day (t.i.d.). In some embodiments, the dose is about 50 mg twice daily. In some embodiments, the dose is about 100 mg twice daily. In some embodiments, the dose is about 150 mg twice daily. In some embodiments, the dose is about 200 mg twice daily. In some embodiments, the dose is about 250 mg twice daily. In some embodiments, the dose is about 300 mg twice daily. In some embodiments, ACY-1215 is administered daily, once a week, twice a week, three times a week, four times a week, or five times a week. In some embodiments, ACY-1215 is administered once a month, twice a month, thrice a month, or 4 times a month. In certain embodiments, ACY-1215 is in a delayed, slow, or timed release form.

In some embodiments, a unit dose of a co-formulated HDAC inhibitor ACY-1215 and antiviral agent comprises less than 400 mg of the HDAC inhibitor ACY-1215 and less than 1000 mg of the antiviral agent. In some embodiments, a unit dose of a co-formulated HDAC inhibitor ACY-1215 and antiviral agent comprises less than 200 mg of the HDAC inhibitor ACY-1215 and less than 1000 mg of the antiviral agent. In certain embodiments, the unit dose comprises less than 50 mg of the HDAC inhibitor ACY-1215 and less than 500 mg of the antiviral agent.

In other embodiments, the unit dose comprises less than 80 mg of the HDAC inhibitor ACY-1215 and less than 1500 mg of the antiviral agent. In some embodiments, the unit dose comprises less than 50 mg of the HDAC inhibitor ACY-1215 and less than 1000 mg of antiviral agent. In some embodiments, the unit dose comprises about 20 mg of the HDAC inhibitor ACY-1215 and about 450 mg of antiviral agent. In certain embodiments, the unit dose comprises about 40 mg of the HDAC inhibitor ACY-1215 and about 900 mg of antiviral agent. In some embodiments, the antiviral agent is formulated as controlled release, delayed release, or slow release.

In some embodiments, the HDAC inhibitor for use in the method described herein is a class I HDAC inhibitor. In some embodiments, the HDAC inhibitor is CHR-3996 (also referred to as VRx-3996, which is chemically identical). The chemical formula of CHR-3996 is (2-(6-{[(6-Fluoroquinolin-2-yl)methyl]amino}-3-azabicyclo[3.1.0]hex-3-yl)-N-hydroxypyrimidine-5-carboxamide). CHR-3996 is a selective Class I HDAC inhibitor and is disclosed in U.S. Pat. No. 7,932,246, which is incorporated by reference herein in its entirety. In certain embodiments, CHR-3996 is administered at a dose of 40 mg/day. In some embodiments, CHR-3996 is administered at a dose of about 1 mg/day, about 2 mg/day, about 5 mg/day, about 10 mg/day, about 15 mg/day, about 20 mg/day, about 25 mg/day, about 30 mg/day, about 35 mg/day, about 40 mg/day, about 45 mg/day, about 50 mg/day, about 60 mg/day, about 70 mg/day, about 80 mg/day, about 90 mg/day, or about 100 mg/day. In certain embodiments, CHR-3996 is administered at a dose of less than 1 mg/day, less than 2 mg/day, less than 5 mg/day, less than 10 mg/day, less than 15 mg/day, less than 20 mg/day, less than 25 mg/day, less than 30 mg/day, less than 35 mg/day, less than 40 mg/day, less than 45 mg/day, less than 50 mg/day, less than 60 mg/day, less than 70 mg/day, less than 80 mg/day, less than 90 mg/day, or less than 100 mg/day. In some embodiments, CHR-3996 is administered at a dose of more than 1 mg/day, more than 2 mg/day, more than 5 mg/day, more than 10 mg/day, more than 15 mg/day, more than 20 mg/day, more than 25 mg/day, more than 30 mg/day, more than 35 mg/day, more than 40 mg/day, more than 45 mg/day, more than 50 mg/day, more than 60 mg/day, more than 70 mg/day, more than 80 mg/day, more than 90 mg/day, or more than 100 mg/day. In certain embodiments, CHR-3996 is administered at a dose of more than 30 mg/day and less than 50 mg/day. In some embodiments, CHR-3996 is administered at a dose of more than 5 mg/day and less than 80 mg/day. In some embodiments, CHR-3996 is administered at a dose of more than 10 mg/day and less than 80 mg/day. In some embodiments, CHR-3996 is administered at a dose of more than 20 mg/day and less than 80 mg/day. In some embodiments, CHR-3996 is administered at a dose of about 1 mg/day, about 2 mg/day, about 5 mg/day, about 6 mg/day, about 7 mg/day, about 8 mg/day, about 9 mg/day, about 10 mg/day, about 11 mg/day, about 12 mg/day, about 13 mg/day, about 14 mg/day, about 15 mg/day, about 16 mg/day, about 17 mg/day, about 18 mg/day, about 19 mg/day, about 20 mg/day, about 22 mg/day, about 23 mg/day, about 25 mg/day, about 27 mg/day, about 28 mg/day, about 30 mg/day, about 32 mg/day, about 33 mg/day, about 35 mg/day, about 40 mg/day, about 45 mg/day, about 50 mg/day, about 60 mg/day, about 70 mg/day, about 80 mg/day, about 90 mg/day, or about 100 mg/day. In certain embodiments, CHR-3996 is administered once a day (q.d.), twice a day (b.i.d.), or thrice a day (t.i.d.). In some embodiments, CHR-3996 is administered daily, once a week, twice a week, three times a week, four times a week, or five times a week.

In some embodiments, the HDAC inhibitor is chidamide. In certain embodiments, chidamide is administered at a dose of 40 mg/day. In some embodiments, chidamide is administered at a dose of about 1 mg/day, about 2 mg/day, about 5 mg/day, about 10 mg/day, about 15 mg/day, about 20 mg/day, about 25 mg/day, about 30 mg/day, about 35 mg/day, about 40 mg/day, about 45 mg/day, about 50 mg/day, about 60 mg/day, about 70 mg/day, about 80 mg/day, about 90 mg/day, about 100 mg/day, about 150 mg/day, about 200 mg/day, about 250 mg/day, about 300 mg/day, about 350 mg/day, or about 400 mg/day. In certain embodiments, chidamide is administered at a dose of less than 1 mg/day, less than 2 mg/day, less than 5 mg/day, less than 10 mg/day, less than 15 mg/day, less than 20 mg/day, less than 25 mg/day, less than 30 mg/day, less than 35 mg/day, less than 40 mg/day, less than 45 mg/day, less than 50 mg/day, less than 60 mg/day, less than 70 mg/day, less than 80 mg/day, less than 90 mg/day, less than 100 mg/day, less than 150 mg/day, less than 200 mg/day, less than 250 mg/day, less than 300 mg/day, less than 350 mg/day, or less than 400 mg/day. In some embodiments, chidamide is administered at a dose of more than 1 mg/day, more than 2 mg/day, more than 5 mg/day, more than 10 mg/day, more than 15 mg/day, more than 20 mg/day, more than 25 mg/day, more than 30 mg/day, more than 35 mg/day, more than 40 mg/day, more than 45 mg/day, more than 50 mg/day, more than 60 mg/day, more than 70 mg/day, more than 80 mg/day, more than 90 mg/day, more than 100 mg/day, more than 150 mg/day, more than 200 mg/day, more than 250 mg/day, more than 300 mg/day, more than 350 mg/day, or more than 400 mg/day. In some embodiments, chidamide is administered at a dose of about 1 mg/day to about 100 mg/day. In certain embodiments, chidamide is administered at a dose of about 5 mg/day to about 80 mg/day. In some embodiments, chidamide is administered at a dose of 5 mg twice weekly to 80 mg twice weekly. In some embodiments, chidamide is administered at a dose of 5 mg thrice weekly to 80 mg thrice weekly. In some embodiments, chidamide is administered at a dose of about 10 mg/day to about 60 mg/day. In some embodiments, chidamide is administered at a dose of 10 mg twice weekly to 60 mg twice weekly. In some embodiments, chidamide is administered at a dose of 10 mg thrice weekly to 60 mg thrice weekly. In some embodiments, chidamide is administered at a dose of 20 mg/day to 50 mg/day. In some embodiments, chidamide is administered at a dose of 20 mg twice weekly to 50 mg twice weekly. In some embodiments, chidamide is administered at a dose of 20 mg thrice weekly to 50 mg thrice weekly. In some embodiments, chidamide is administered at a dose of 30 mg/day to 40 mg/day. In some embodiments, chidamide is administered at a dose of 30 mg twice weekly to 40 mg twice weekly. In some embodiments, chidamide is administered at a dose of 30 mg thrice weekly to 40 mg thrice weekly. In certain embodiments, chidamide is administered once a day (q.d.), twice a day (b.i.d.), or thrice a day (t.i.d.). In some embodiments, chidamide is administered daily, once a week, twice a week, three times a week, four times a week, or five times a week. In some embodiments, chidamide is administered once a month, twice a month, thrice a month, or 4 times a month. In certain embodiments, chidamide is in a delayed, slow, or timed release form.

In some embodiments, the HDAC inhibitor is 4SC-202. In certain embodiments, 4SC-202 is administered at a dose of 200 mg/day. In some embodiments, 4SC-202 is administered at a dose of about 1 mg/day, about 2 mg/day, about 5 mg/day, about 10 mg/day, about 15 mg/day, about 20 mg/day, about 25 mg/day, about 30 mg/day, about 35 mg/day, about 40 mg/day, about 45 mg/day, about 50 mg/day, about 60 mg/day, about 70 mg/day, about 80 mg/day, about 90 mg/day, about 100 mg/day, about 150 mg/day, about 200 mg/day, about 250 mg/day, about 300 mg/day, about 350 mg/day, about 400 mg/day, about 450 mg/day, or about 500 mg/day. In certain embodiments, 4SC-202 is administered at a dose of less than 1 mg/day, less than 2 mg/day, less than 5 mg/day, less than 10 mg/day, less than 15 mg/day, less than 20 mg/day, less than 25 mg/day, less than 30 mg/day, less than 35 mg/day, less than 40 mg/day, less than 45 mg/day, less than 50 mg/day, less than 60 mg/day, less than 70 mg/day, less than 80 mg/day, less than 90 mg/day, or less than 100 mg/day, less than 150 mg/day, less than 200 mg/day, less than 250 mg/day, less than 300 mg/day, less than 350 mg/day less than 400 mg/day, less than 450 mg/day, or less than 500 mg/day. In some embodiments, 4SC-202 is administered at a dose of more than 1 mg/day, more than 2 mg/day, more than 5 mg/day, more than 10 mg/day, more than 15 mg/day, more than 20 mg/day, more than 25 mg/day, more than 30 mg/day, more than 35 mg/day, more than 40 mg/day, more than 45 mg/day, more than 50 mg/day, more than 60 mg/day, more than 70 mg/day, more than 80 mg/day, more than 90 mg/day, more than 100 mg/day, more than 150 mg/day, more than 200 mg/day, more than 250 mg/day, more than 300 mg/day, more than 350 mg/day more than 400 mg/day, more than 450 mg/day, or more than 500 mg/day. In some embodiments, 4SC-202 is administered at a dose of about 10 mg/day to about 1000 mg/day. In certain embodiments, 4SC-202 is administered at a dose of about 20 mg/day to about 800 mg/day. In some embodiments, 4SC-202 is administered at a dose of about 25 mg/day to about 600 mg/day. In certain embodiments, 4SC-202 is administered once a day (q.d.), twice a day (b.i.d.), or thrice a day (t.i.d.). In some embodiments, the dose is about 50 mg twice daily. In some embodiments, the dose is about 100 mg twice daily. In some embodiments, the dose is about 150 mg twice daily. In some embodiments, the dose is about 200 mg twice daily. In some embodiments, the dose is about 250 mg twice daily. In some embodiments, the dose is about 300 mg twice daily. In some embodiments, 4SC-202 is administered daily, once a week, twice a week, three times a week, four times a week, or five times a week. In some embodiments, 4SC-202 is administered once a month, twice a month, thrice a month, or 4 times a month. In certain embodiments, 4SC-202 is in a delayed, slow, or timed release form.

In some embodiments, the HDAC inhibitor is ITF-2357. In certain embodiments, ITF-2357 is administered at a dose of 100 mg/day. In some embodiments, ITF-2357 is administered at a dose of about 1 mg/day, about 2 mg/day, about 5 mg/day, about 10 mg/day, about 15 mg/day, about 20 mg/day, about 25 mg/day, about 30 mg/day, about 35 mg/day, about 40 mg/day, about 45 mg/day, about 50 mg/day, about 60 mg/day, about 70 mg/day, about 80 mg/day, about 90 mg/day, about 100 mg/day, about 120 mg/day, about 125 mg/day, about 140 mg/day, about 150 mg/day, about 160 mg/day, about 175 mg/day, about 180 mg/day, about 200 mg/day, about 225 mg/day, about 250 mg/day, about 275 mg/day, or about 300 mg/day. In certain embodiments, ITF-2357 is administered at a dose of less than 1 mg/day, less than 2 mg/day, less than 5 mg/day, less than 10 mg/day, less than 15 mg/day, less than 20 mg/day, less than 25 mg/day, less than 30 mg/day, less than 35 mg/day, less than 40 mg/day, less than 45 mg/day, less than 50 mg/day, less than 60 mg/day, less than 70 mg/day, less than 80 mg/day, less than 90 mg/day, less than 100 mg/day, less than 120 mg/day, less than 125 mg/day, less than 140 mg/day, less than 150 mg/day, less than 160 mg/day, less than 175 mg/day, less than 180 mg/day, less than 200 mg/day, less than 225 mg/day, less than 250 mg/day, less than 275 mg/day, or less than 300 mg/day. In some embodiments, ITF-2357 is administered at a dose of more than 1 mg/day, more than 2 mg/day, more than 5 mg/day, more than 10 mg/day, more than 15 mg/day, more than 20 mg/day, more than 25 mg/day, more than 30 mg/day, more than 35 mg/day, more than 40 mg/day, more than 45 mg/day, more than 50 mg/day, more than 60 mg/day, more than 70 mg/day, more than 80 mg/day, more than 90 mg/day, more than 100 mg/day, more than 120 mg/day, more than 125 mg/day, more than 140 mg/day, more than 150 mg/day, more than 160 mg/day, more than 175 mg/day, more than 180 mg/day, more than 200 mg/day, more than 225 mg/day, more than 250 mg/day, more than 275 mg/day, or more than 300 mg/day. In certain embodiments, ITF-2357 is administered at a dose of more than 80 mg/day and less than 120 mg/day. In some embodiments, ITF-2357 is administered at a dose of more than 40 mg/day and less than 120 mg/day. In certain embodiments, ITF-2357 is administered at a dose of more than 50 mg/day and less than 240 mg/day. In some embodiments, ITF-2357 is administered once a day (q.d.), twice a day (b.i.d.), or thrice a day (t.i.d.). In some embodiments, ITF-2357 is administered daily, once a week, twice a week, three times a week, four times a week, or five times a week.

In some embodiments, the HDAC inhibitor is JNJ-16241199/R306465. In certain embodiments, JNJ-16241199/R306465 is administered at a dose of 100 mg/day. In some embodiments, JNJ-16241199/R306465 is administered at a dose of about 1 mg/day, about 2 mg/day, about 5 mg/day, about 10 mg/day, about 15 mg/day, about 20 mg/day, about 25 mg/day, about 30 mg/day, about 35 mg/day, about 40 mg/day, about 45 mg/day, about 50 mg/day, about 60 mg/day, about 70 mg/day, about 80 mg/day, about 90 mg/day, about 100 mg/day, about 120 mg/day, about 125 mg/day, about 140 mg/day, about 150 mg/day, about 160 mg/day, about 175 mg/day, about 180 mg/day, about 200 mg/day, about 225 mg/day, about 250 mg/day, about 275 mg/day, or about 300 mg/day. In certain embodiments, JNJ-16241199/R306465 is administered at a dose of less than 1 mg/day, less than 2 mg/day, less than 5 mg/day, less than 10 mg/day, less than 15 mg/day, less than 20 mg/day, less than 25 mg/day, less than 30 mg/day, less than 35 mg/day, less than 40 mg/day, less than 45 mg/day, less than 50 mg/day, less than 60 mg/day, less than 70 mg/day, less than 80 mg/day, less than 90 mg/day, less than 100 mg/day, less than 120 mg/day, less than 125 mg/day, less than 140 mg/day, less than 150 mg/day, less than 160 mg/day, less than 175 mg/day, less than 180 mg/day, less than 200 mg/day, less than 225 mg/day, less than 250 mg/day, less than 275 mg/day, or less than 300 mg/day. In some embodiments, JNJ-16241199/R306465 is administered at a dose of more than 1 mg/day, more than 2 mg/day, more than 5 mg/day, more than 10 mg/day, more than 15 mg/day, more than 20 mg/day, more than 25 mg/day, more than 30 mg/day, more than 35 mg/day, more than 40 mg/day, more than 45 mg/day, more than 50 mg/day, more than 60 mg/day, more than 70 mg/day, more than 80 mg/day, more than 90 mg/day, more than 100 mg/day, more than 120 mg/day, more than 125 mg/day, more than 140 mg/day, more than 150 mg/day, more than 160 mg/day, more than 175 mg/day, more than 180 mg/day, more than 200 mg/day, more than 225 mg/day, more than 250 mg/day, more than 275 mg/day, or more than 300 mg/day. In certain embodiments, JNJ-16241199/R306465 is administered at a dose of more than 80 mg/day and less than 120 mg/day. In some embodiments, JNJ-16241199/R306465 is administered at a dose of more than 40 mg/day and less than 120 mg/day. In certain embodiments, JNJ-16241199/R306465 is administered at a dose of more than 50 mg/day and less than 240 mg/day. In some embodiments, JNJ-16241199/R306465 is administered once a day (q.d.), twice a day (b.i.d.), or thrice a day (t.i.d.). In some embodiments, JNJ-16241199/R306465 is administered daily, once a week, twice a week, three times a week, four times a week, or five times a week.

In some embodiments, the HDAC inhibitor is JNJ-26481585. In certain embodiments, JNJ-26481585 is administered at a dose of 10 mg/day. In some embodiments, JNJ-26481585 is administered at a dose of about 0.1 mg/day, about 0.2 mg/day, about 0.5 mg/day, about 1 mg/day, about 2 mg/day, about 5 mg/day, about 10 mg/day, about 15 mg/day, about 20 mg/day, about 25 mg/day, about 30 mg/day, about 35 mg/day, about 40 mg/day, about 45 mg/day, about 50 mg/day, about 60 mg/day, about 70 mg/day, about 80 mg/day, about 90 mg/day, or about 100 mg/day. In certain embodiments, JNJ-26481585 is administered at a dose of less than 0.1 mg/day, less than 0.2 mg/day, less than 0.5 mg/day, less than 1 mg/day, less than 2 mg/day, less than 5 mg/day, less than 10 mg/day, less than 15 mg/day, less than 20 mg/day, less than 25 mg/day, less than 30 mg/day, less than 35 mg/day, less than 40 mg/day, less than 45 mg/day, less than 50 mg/day, less than 60 mg/day, less than 70 mg/day, less than 80 mg/day, less than 90 mg/day, or less than 100 mg/day. In some embodiments, JNJ-26481585 is administered at a dose of more than 0.1 mg/day, more than 0.2 mg/day, more than 0.5 mg/day, more than 1 mg/day, more than 2 mg/day, more than 5 mg/day, more than 10 mg/day, more than 15 mg/day, more than 20 mg/day, more than 25 mg/day, more than 30 mg/day, more than 35 mg/day, more than 40 mg/day, more than 45 mg/day, more than 50 mg/day, more than 60 mg/day, more than 70 mg/day, more than 80 mg/day, more than 90 mg/day, or more than 100 mg/day. In certain embodiments, JNJ-26481585 is administered at a dose of more than 2 mg/day and less than 20 mg/day. In some embodiments, JNJ-26481585 is administered at a dose of more than 5 mg/day and less than 30 mg/day. In certain embodiments, JNJ-26481585 is administered once a day (q.d.), twice a day (b.i.d.), or thrice a day (t.i.d.). In some embodiments, JNJ-26481585 is administered daily, once a week, twice a week, three times a week, four times a week, or five times a week.

In some embodiments, the HDAC inhibitor is MGCD0103. In certain embodiments, MGCD0103 is administered at a dose of 45 mg/m$^2$/day. In some embodiments, MGCD0103 is administered at a dose of about 1 mg/m$^2$/day, about 2 mg/m$^2$/day, about 5 mg/m$^2$/day, about 10 mg/m$^2$/day, about 15 mg/m$^2$/day, about 20 mg/m$^2$/day, about 25 mg/m$^2$/day, about 30 mg/m$^2$/day, about 35 mg/m$^2$/day, about 40 mg/m$^2$/day, about 45 mg/m$^2$/day, about 50 mg/m$^2$/day, about 60 mg/m$^2$/day, about 70 mg/m$^2$/day, about 80 mg/m$^2$/day, about 90 mg/m$^2$/day, or about 100 mg/m$^2$/day. In certain embodiments, MGCD0103 is administered at a dose of less than 1 mg/m$^2$/day, less than 2 mg/m$^2$/day, less than 5 mg/m$^2$/day, less than 10 mg/m$^2$/day, less than 15 mg/m$^2$/day, less than 20 mg/m$^2$/day, less than 25 mg/m$^2$/day, less than 30 mg/m$^2$/day, less than 35 mg/m$^2$/day, less than 40 mg/m$^2$/day, less than 45 mg/m$^2$/day, less than 50 mg/m$^2$/day, less than 60 mg/m$^2$/day, less than 70 mg/m$^2$/day, less than 80 mg/m$^2$/day, less than 90 mg/m$^2$/day, or less than 100 mg/m$^2$/day. In some embodiments, MGCD0103 is administered at a dose of more than 1 mg/m$^2$/day, more than 2 mg/m$^2$/day, more than 5 mg/m$^2$/day, more than 10 mg/m$^2$/day, more than 15 mg/m$^2$/day, more than 20 mg/m$^2$/day, more than 25 mg/m$^2$/day, more than 30 mg/m$^2$/day, more than 35 mg/m$^2$/day, more than 40 mg/m$^2$/day, more than 45 mg/m$^2$/day, more than 50 mg/m$^2$/day, more than 60 mg/m$^2$/day, more than 70 mg/m$^2$/day, more than 80 mg/m$^2$/day, more than 90 mg/m$^2$/day, or more than 100 mg/m$^2$/day. In certain embodiments, MGCD0103 is administered at a dose of more than 30 mg/m$^2$/day and less than 80 mg/m$^2$/day. In some embodiments, MGCD0103 is administered at a dose of more than 45 mg/m$^2$/day and less than 60 mg/m$^2$/day. In certain embodiments, MGCD0103 is administered once a day (q.d.), twice a day (b.i.d.), or thrice a day (t.i.d.). In some embodiments, MGCD0103 is administered daily, once a week, twice a week, three times a week, four times a week, or five times a week.

In some embodiments, the HDAC inhibitor is MS-275. In certain embodiments, MS-275 is administered at a dose of 4 mg/m$^2$/day. In some embodiments, MS-275 is administered at a dose of about 0.1 mg/m$^2$/day, of about 0.2 mg/m$^2$/day, of about 0.5 mg/m$^2$/day, of about 1 mg/m$^2$/day, of about 2 mg/m$^2$/day, of about 3 mg/m$^2$/day, of about 4 mg/m$^2$/day, about 5 mg/m$^2$/day, of about 6 mg/m$^2$/day, of about 7 mg/m$^2$/day, of about 8 mg/m$^2$/day, of about 9 mg/m$^2$/day, about 10 mg/m$^2$/day, about 15 mg/m$^2$/day, about 20 mg/m$^2$/day, about 25 mg/m$^2$/day, about 30 mg/m$^2$/day, about 35 mg/m$^2$/day, about 40 mg/m$^2$/day, about 45 mg/m$^2$/day, about 50 mg/m$^2$/day, about 60 mg/m$^2$/day, about 70 mg/m$^2$/day, about 80 mg/m$^2$/day, about 90 mg/m$^2$/day, or about 100 mg/m$^2$/day. In certain embodiments, MS-275 is administered at a dose of less than 0.1 mg/m$^2$/day, of less than 0.2 mg/m$^2$/day, of less than 0.5 mg/m$^2$/day, of less than 1 mg/m$^2$/day, of less than 2 mg/m$^2$/day, of less than 3 mg/m$^2$/day, of less than 4 mg/m$^2$/day, less than 5 mg/m$^2$/day, of less than 6 mg/m$^2$/day, of less than 7 mg/m$^2$/day, of less than 8 mg/m$^2$/day, of less than 9 mg/m$^2$/day, less than 10 mg/m$^2$/day, less than 15 mg/m$^2$/day, less than 20 mg/m$^2$/day, less than 25 mg/m$^2$/day, less than 30 mg/m$^2$/day, less than 35 mg/m$^2$/day, less than 40 mg/m$^2$/day, less than 45 mg/m$^2$/day, less than 50 mg/m$^2$/day, less than 60 mg/m$^2$/day, less than 70 mg/m$^2$/day, less than 80 mg/m$^2$/day, less than 90 mg/m$^2$/day, or less than 100 mg/m$^2$/day. In some embodiments, MS-275 is administered at a dose of more than 0.1 mg/m$^2$/day, of more than 0.2 mg/m$^2$/day, of more than 0.5 mg/m$^2$/day, of more than 1 mg/m$^2$/day, of more than 2 mg/m$^2$/day, of more than 3 mg/m$^2$/day, of more than 4 mg/m$^2$/day, more than 5 mg/m$^2$/day, of more than 6 mg/m$^2$/day, of more than 7 mg/m$^2$/day, of more than 8 mg/m$^2$/day, of more than 9 mg/m$^2$/day, more than 10 mg/m$^2$/day, more than 15 mg/m$^2$/day, more than 20 mg/m$^2$/day, more than 25 mg/m$^2$/day, more than 30 mg/m$^2$/day, more than 35 mg/m$^2$/day, more than 40 mg/m$^2$/day, more than 45 mg/m$^2$/day, more than 50 mg/m$^2$/day, more than 60 mg/m$^2$/day, more than 70 mg/m$^2$/day, more than 80 mg/m$^2$/day, more than 90 mg/m$^2$/day, or more than 100 mg/m$^2$/day. In certain embodiments, MS-275 is administered at a dose of more than 2 mg/m$^2$/day and less than 10 mg/m$^2$/day. In some embodiments, MS-275 is administered at a dose of more than 2 mg/m$^2$/day and less than 40 mg/m$^2$/day. In certain embodiments, MS-275 is administered at a dose of more than 2 mg/m$^2$/day and less than 6 mg/m$^2$/day. In some embodiments, MS-275 is administered at a dose of more than 6 mg/m$^2$/day and less than 8 mg/m$^2$/day. In certain embodiments, MS-275 is administered once a day (q.d.), twice a day (b.i.d.), or thrice a day (t.i.d.). In some embodiments, MS-275 is administered daily, once a week, twice a week, three times a week, four times a week, or five times a week.

In some embodiments, the HDAC inhibitor is SB939. In certain embodiments, SB939 is administered at a dose of 60 mg/day. In some embodiments, SB939 is administered at a dose of about 1 mg/day, about 2 mg/day, about 5 mg/day, about 10 mg/day, about 15 mg/day, about 20 mg/day, about 25 mg/day, about 30 mg/day, about 35 mg/day, about 40 mg/day, about 45 mg/day, about 50 mg/day, about 60 mg/day, about 70 mg/day, about 80 mg/day, about 90 mg/day, about 100 mg/day, about 120 mg/day, about 125 mg/day, about 140 mg/day, about 150 mg/day, about 160 mg/day, about 175 mg/day, about 180 mg/day, or about 200 mg/day. In certain embodiments, SB939 is administered at a dose of less than 1 mg/day, less than 2 mg/day, less than 5 mg/day, less than 10 mg/day, less than 15 mg/day, less than 20 mg/day, less than 25 mg/day, less than 30 mg/day, less than 35 mg/day, less than 40 mg/day, less than 45 mg/day, less than 50 mg/day, less than 60 mg/day, less than 70 mg/day, less than 80 mg/day, less than 90 mg/day, less than 100 mg/day, less than 120 mg/day, less than 125 mg/day, less than 140 mg/day, less than 150 mg/day, less than 160 mg/day, less than 175 mg/day, less than 180 mg/day, or less than 200 mg/day. In some embodiments, SB939 is administered at a dose of more than 1 mg/day, more than 2 mg/day, more than 5 mg/day, more than 10 mg/day, more than 15 mg/day, more than 20 mg/day, more than 25 mg/day, more than 30 mg/day, more than 35 mg/day, more than 40 mg/day, more than 45 mg/day, more than 50 mg/day, more than 60 mg/day, more than 70 mg/day, more than 80 mg/day, more than 90 mg/day, more than 100 mg/day, more than 120 mg/day, more than 125 mg/day, more than 140 mg/day, more than 150 mg/day, more than 160 mg/day, more than 175 mg/day, more than 180 mg/day, or more than 200 mg/day. In certain embodiments, SB939 is administered at a dose of more than 30 mg/day and less than 70 mg/day. In some embodiments, SB939 is administered at a dose of more than 10 mg/day and less than 90 mg/day. In certain embodiments, SB939 is administered once a day (q.d.), twice a day (b.i.d.), or thrice a day (t.i.d.). In some embodiments, SB939 is administered daily, once a week, twice a week, three times a week, four times a week, or five times a week.

In some embodiments, the HDAC inhibitor is romidepsin. In certain embodiments, romidepsin is administered at a dose of 14 mg/m$^2$/day. In some embodiments, romidepsin is administered at a dose of about 0.1 mg/m$^2$/day, of about 0.2 mg/m$^2$/day, of about 0.5 mg/m$^2$/day, of about 1 mg/m$^2$/day, of about 2 mg/m$^2$/day, of about 3 mg/m$^2$/day, of about 4 mg/m$^2$/day, about 5 mg/m$^2$/day, of about 6 mg/m$^2$/day, of about 7 mg/m$^2$/day, of about 8 mg/m$^2$/day, of about 9 mg/m$^2$/day, about 10 mg/m$^2$/day, about 11 mg/m$^2$/day, about 12 mg/m$^2$/day, about 13 mg/m$^2$/day, about 14 mg/m$^2$/day, about 15 mg/m$^2$/day, about 16 mg/m$^2$/day, about 17 mg/m$^2$/day, about 18 mg/m$^2$/day, about 19 mg/m$^2$/day, about 20 mg/m$^2$/day, about 25 mg/m$^2$/day, about 30 mg/m$^2$/day, about 35 mg/m$^2$/day, about 40 mg/m$^2$/day, about 45 mg/m$^2$/day, about 50 mg/m$^2$/day, about 60 mg/m$^2$/day, about 70 mg/m$^2$/day, about 80 mg/m$^2$/day, about 90 mg/m$^2$/day, or about 100 mg/m$^2$/day. In certain embodiments, romidepsin is administered at a dose of less than 0.1 mg/m$^2$/day, of less than 0.2 mg/m$^2$/day, of less than 0.5 mg/m$^2$/day, of less than 1 mg/m$^2$/day, of less than 2 mg/m$^2$/day, of less than 3 mg/m$^2$/day, of less than 4 mg/m$^2$/day, less than 5 mg/m$^2$/day, of less than 6 mg/m$^2$/day, of less than 7 mg/m$^2$/day, of less than 8 mg/m$^2$/day, of less than 9 mg/m$^2$/day, less than 10 mg/m$^2$/day, less than 11 mg/m$^2$/day, less than 12 mg/m$^2$/day, less than 13 mg/m$^2$/day, less than 14 mg/m$^2$/day, less than 15 mg/m$^2$/day, less than 16 mg/m$^2$/day, less than 17 mg/m$^2$/day, less than 18 mg/m$^2$/day, less than 19 mg/m$^2$/day, less than 20 mg/m$^2$/day, less than 25 mg/m$^2$/day, less than 30 mg/m$^2$/day, less than 35 mg/m$^2$/day, less than 40 mg/m$^2$/day, less than 45 mg/m$^2$/day, less than 50 mg/m$^2$/day, less than 60 mg/m$^2$/day, less than 70 mg/m$^2$/day, less than 80 mg/m$^2$/day, less than 90 mg/m$^2$/day, or less than 100 mg/m$^2$/day. In some embodiments, romidepsin is administered at a dose of more than 0.1 mg/m$^2$/day, of more than 0.2 mg/m$^2$/day, of more than 0.5 mg/m$^2$/day, of more than 1 mg/m$^2$/day, of more than 2 mg/m$^2$/day, of more than 3 mg/m$^2$/day, of more than 4 mg/m$^2$/day, more than 5 mg/m$^2$/day, of more than 6 mg/m$^2$/day, of more than 7 mg/m$^2$/day, of more than 8 mg/m$^2$/day, of more than 9 mg/m$^2$/day, more than 10 mg/m$^2$/day, more than 11 mg/m$^2$/day, more than 12 mg/m$^2$/day, more than 13 mg/m$^2$/day, more than 14 mg/m$^2$/day, more than 15 mg/m$^2$/day, more than 16 mg/m$^2$/day, more than 17 mg/m$^2$/day, more than 18 mg/m$^2$/day, more than 19 mg/m$^2$/day, more than 20 mg/m$^2$/day, more than 25 mg/m$^2$/day, more than 30 mg/m$^2$/day, more than 35 mg/m$^2$/day, more than 40 mg/m$^2$/day, more than 45 mg/m$^2$/day, more than 50 mg/m$^2$/day, more than 60 mg/m$^2$/day, more than 70 mg/m$^2$/day, more than 80 mg/m$^2$/day, more than 90 mg/m$^2$/day, or more than 100 mg/m$^2$/day. In certain embodiments, romidepsin is administered at a dose of more than 13 mg/m$^2$/day and less than 18 mg/m$^2$/day. In some embodiments, romidepsinis administered at a dose of more than 10 mg/m$^2$/day and less than 20 mg/m$^2$/day. In certain embodiments, romidepsin is administered once a day (q.d.), twice a day (b.i.d.), or thrice a day (t.i.d.). In some embodiments, romidepsin is administered daily, once a week, twice a week, three times a week, four times a week, or five times a week.

In some embodiments, the HDAC inhibitor is LBH589. In certain embodiments, LBH589 is administered at a dose of 20 mg/day. In some embodiments, LBH589 is administered at a dose of about 1 mg/day, about 2 mg/day, about 5 mg/day, about 10 mg/day, about 15 mg/day, about 20 mg/day, about 25 mg/day, about 30 mg/day, about 35 mg/day, about 40 mg/day, about 45 mg/day, about 50 mg/day, about 60 mg/day, about 70 mg/day, about 80 mg/day, about 90 mg/day, or about 100 mg/day. In certain embodiments, LBH589 is administered at a dose of less than 1 mg/day, less than 2 mg/day, less than 5 mg/day, less than 10 mg/day, less than 15 mg/day, less than 20 mg/day, less than 25 mg/day, less than 30 mg/day, less than 35 mg/day, less than 40 mg/day, less than 45 mg/day, less than 50 mg/day, less than 60 mg/day, less than 70 mg/day, less than 80 mg/day, less than 90 mg/day, or less than 100 mg/day. In some embodiments, LBH589 is administered at a dose of more than 1 mg/day, more than 2 mg/day, more than 5 mg/day, more than 10 mg/day, more than 15 mg/day, more than 20 mg/day, more than 25 mg/day, more than 30 mg/day, more than 35 mg/day, more than 40 mg/day, more than 45 mg/day, more than 50 mg/day, more than 60 mg/day, more than 70 mg/day, more than 80 mg/day, more than 90 mg/day, or more than 100 mg/day. In certain embodiments, LBH589 is administered at a dose of more than 10 mg/day and less than 20 mg/day. In some embodiments, LBH589 is administered at a dose of more than 5 mg/day and less than 30 mg/day. In certain embodiments, LBH589 is administered once a day (q.d.), twice a day (b.i.d.), or thrice a day (t.i.d.). In some embodiments, LBH589 is administered daily, once a week, twice a week, three times a week, four times a week, or five times a week.

In some embodiments, the HDAC inhibitor is PXD101. In certain embodiments, PXD101 is administered at a dose of 1000 mg/m$^2$/day. In some embodiments, PXD101 is administered at a dose of about 10 mg/m$^2$/day, about 15 mg/m$^2$/day, about 20 mg/m$^2$/day, about 50 mg/m$^2$/day, about 75 mg/m$^2$/day, about 100 mg/m$^2$/day, about 150 mg/m$^2$/day, about 200 mg/m$^2$/day, about 300 mg/m$^2$/day, about 400 mg/m$^2$/day, about 500 mg/m$^2$/day, about 600 mg/m$^2$/day, about 700 mg/m$^2$/day, about 800 mg/m$^2$/day, about 900 mg/m$^2$/day, about 1000 mg/m$^2$/day, about 1100 mg/m$^2$/day, about 1200 mg/m$^2$/day, about 1300 mg/m$^2$/day, about 1400 mg/m$^2$/day, about 1500 mg/m$^2$/day, about 1750 mg/m$^2$/day, or about 2000 mg/m$^2$/day. In certain embodiments, PXD101 is administered at a dose of less than 10 mg/m$^2$/day, less than 15 mg/m$^2$/day, less than 20 mg/m$^2$/day, less than 50 mg/m$^2$/day, less than 75 mg/m$^2$/day, less than 100 mg/m$^2$/day, less than 150 mg/m$^2$/day, less than 200 mg/m$^2$/day, less than 300 mg/m$^2$/day, less than 400 mg/m$^2$/day, less than 500 mg/m$^2$/day, less than 600 mg/m$^2$/day, less than 700 mg/m$^2$/day, less than 800 mg/m$^2$/day, less than 900 mg/m$^2$/day, less than 1000 mg/m$^2$/day, less than 1100 mg/m$^2$/day, less than 1200 mg/m$^2$/day, less than 1300 mg/m$^2$/day, less than 1400 mg/m$^2$/day, less than 1500 mg/m$^2$/day, less than 1750 mg/m$^2$/day, or less than 2000 mg/m$^2$/day. In some embodiments, PXD101 is administered at a dose of more than 10 mg/m$^2$/day, more than 15 mg/m$^2$/day, more than 20 mg/m$^2$/day, more than 50 mg/m$^2$/day, more than 75 mg/m$^2$/day, more than 100 mg/m$^2$/day, more than 150 mg/m$^2$/day, more than 200 mg/m$^2$/day, more than 300 mg/m$^2$/day, more than 400 mg/m$^2$/day, more than 500 mg/m$^2$/day, more than 600 mg/m$^2$/day, more than 700 mg/m$^2$/day, more than 800 mg/m$^2$/day, more than 900 mg/m$^2$/day, more than 1000 mg/m$^2$/day, more than 1100 mg/m$^2$/day, more than 1200 mg/m$^2$/day, more than 1300 mg/m$^2$/day, more than 1400 mg/m$^2$/day, more than 1500 mg/m$^2$/day, more than 1750 mg/m$^2$/day, or more than 2000 mg/m$^2$/day. In certain embodiments, PXD101 is administered at a dose of more than 600 mg/m$^2$/day and less than 1000 mg/m$^2$/day. In some embodiments, PXD101 is administered at a dose of more than 15 mg/m$^2$/day and less than 1000 mg/m$^2$/day. In certain embodiments, PXD101 is administered once a day (q.d.), twice a day (b.i.d.), or thrice a day (t.i.d.). In some embodiments, PXD101 is administered daily, once a week, twice a week, three times a week, four times a week, or five times a week.

In some embodiments, the HDAC inhibitor is vorinostat. In certain embodiments, vorinostat is administered at a dose of 400 mg/day. In some embodiments, vorinostat is administered at a dose of about 10 mg/day, about 20 mg/day, about 30 mg/day, about 40 mg/day, about 50 mg/day, about 60 mg/day, about 70 mg/day, about 80 mg/day, about 90 mg/day, about 100 mg/day, about 125 mg/day, about 150 mg/day, about 175 mg/day, about 200 mg/day, about 225 mg/day, about 250 mg/day, about 275 mg/day, about 300 mg/day, about 325 mg/day, about 350 mg/day, about 375 mg/day, about 400 mg/day, about 450 mg/day, about 500 mg/day, about 550 mg/day, about 600 mg/day, about 650 mg/day, about 700 mg/day, about 750 mg/day, about 800 mg/day, about 900 mg/day, or about 1000 mg/day. In certain embodiments, vorinostat is administered at a dose of less than 10 mg/day, less than 20 mg/day, less than 30 mg/day, less than 40 mg/day, less than 50 mg/day, less than 60 mg/day, less than 70 mg/day, less than 80 mg/day, less than 90 mg/day, less than 100 mg/day, less than 125 mg/day, less than 150 mg/day, less than 175 mg/day, less than 200 mg/day, less than 225 mg/day, less than 250 mg/day, less than 275 mg/day, less than 300 mg/day, less than 325 mg/day, less than 350 mg/day, less than 375 mg/day, less than 400 mg/day, less than 450 mg/day, less than 500 mg/day, less than 550 mg/day, less than 600 mg/day, less than 650 mg/day, less than 700 mg/day, less than 750 mg/day, less than 800 mg/day, less than 900 mg/day, or less than 1000 mg/day. In some embodiments, vorinostat is administered at a dose of more than 10 mg/day, more than 20 mg/day, more than 30 mg/day, more than 40 mg/day, more than 50 mg/day, more than 60 mg/day, more than 70 mg/day, more than 80 mg/day, more than 90 mg/day, more than 100 mg/day, more than 125 mg/day, more than 150 mg/day, more than 175 mg/day, more than 200 mg/day, more than 225 mg/day, more than 250 mg/day, more than 275 mg/day, more than 300 mg/day, more than 325 mg/day, more than 350 mg/day, more than 375 mg/day, more than 400 mg/day, more than 450 mg/day, more than 500 mg/day, more than 550 mg/day, more than 600 mg/day, more than 650 mg/day, more than 700 mg/day, more than 750 mg/day, more than 800 mg/day, more than 900 mg/day, or more than 1000 mg/day. In certain embodiments, vorinostat is administered at a dose of more than 100 mg/day and less than 400 mg/day. In some embodiments, vorinostat is administered at a dose of more than 100 mg/day and less than 500 mg/day. In certain embodiments, vorinostat is administered once a day (q.d.), twice a day (b.i.d.), or thrice a day (t.i.d.). In some embodiments, vorinostat is administered daily, once a week, twice a week, three times a week, four times a week, or five times a week.

In some embodiments, an HDAC inhibitor inhibits the growth of virus-positive cells. In some embodiments, an HDAC inhibitor inhibits the growth of EBV-positive cells. In certain embodiments, the HDAC inhibitor inhibits the growths of EBV-positive lymphoma cells. In some embodiments, the HDAC inhibitor has growth inhibitory activity at a concentration of about 100 μM, about 90 μM, about 80 μM, about 75 μM, about 70 μM, about 60 μM, about 50 μM, about 40 μM, about 30 μM, about 25 μM, about 20 μM, about 10 μM, about 5 μM, about 2 μM, about 1 μM, about 900 nM, about 800 nM, about 700 nM, about 600 nM, about 500 nM, about 400 nM, about 300 nM, about 200 nM, about 100 nM, about 75 nM, about 50 nM, about 20 nM, or about 10 nM. In certain embodiments, the HDAC inhibitor has growth inhibitory activity at a concentration of less than 100 μM, less than 90 μM, less than 80 μM, less than 75 μM, less than 70 μM, less than 60 μM, less than 50 μM, less than 40 μM, less than 30 μM, less than 25 μM, less than 20 μM, less than 10 μM, less than 5 μM, less than 2 μM, less than 1 μM, less than 900 nM, less than 800 nM, less than 700 nM, less than 600 nM, less than 500 nM, less than 400 nM, less than 300 nM, less than 200 nM, less than 100 nM, less than 75 nM, less than 50 nM, less than 20 nM, or less than 10 nM. In some embodiments, the HDAC inhibitor has growth inhibitory activity at a concentration of more than 100 μM, more than 90 μM, more than 80 μM, more than 75 μM, more than 70 μM, more than 60 μM, more than 50 μM, more than 40 μM, more than 30 μM, more than 25 μM, more than 20 μM, more than 10 μM, more than 5 μM, more than 2 μM, more than 1 μM, more than 900 nM, more than 800 nM, more than 700 nM, more than 600 nM, more than 500 nM, more than 400 nM, more than 300 nM, more than 200 nM, more than 100 nM, more than 75 nM, more than 50 nM, more than 20 nM, or more than 10 nM. In certain embodiments, the HDAC inhibitor has growth inhibitory activity at more than 50 nM and less than 100 nM. In some embodiments, the HDAC inhibitor has growth inhibitory activity at more than 200 nM and less than 500 nM. In certain embodiments, the HDAC inhibitor has growth inhibitory activity at more than 100 nM and less than 200 nM.

HDAC inhibitors and inducing agents (agents that induce expression) may act directly on the viral genome or indirectly through a cellular factor required for viral expression. For example, viral gene expression can be regulated through the regulation of the expression of viral transcription factors such as ZTA, RTA, tat, and tax, cellular transcription factors such as AP-1, AP-2, Sp 1, NF-κB, and other transcriptional activators and/or repressors (factors), co-activators and co-repressors, histone acetylators and deacetylators, DNA methylases and demethylases, oncogenes or proto-oncogenes, or protein kinase C. These proteins act to regulate and thereby control expression of specific viral and/or other cellular genetic elements. According to the methods of the invention, control over their expression can lead to control over the infection. Other gene products, both viral and cellular in origin, whose expression can be regulated with inducing agents, include proteases, polymerases, reverse transcriptases, cell-surface receptors, major histocompatibility antigens, growth factors, and combinations of these products.

Alteration of expression of certain transcription factors may affect regulation of gene expression and regulation of the cell cycle. In the breast cancer cell line MCF-7, butyrate induces a block in cellular proliferation that is associated with decreased expression of estrogen and prolactin hormone receptor mRNA expression, thus blocking the potential growth stimulation by estrogen and prolactin. These effects are associated with increased expression of the EGF receptor. Butyrate also has been shown to induce down-regulation of c-myc and p53 mRNA and to up-regulate expression of the c-fos transcription factor. In mouse fibroblasts, butyrate will block the cell cycle in the $G_1$ phase. When these cells are stimulated to proliferate with serum, TPA, or insulin, the immediate-early response transcription factors c-myc and c-jun are unregulated. However, the late $G_1$ phase downstream gene marker cdc-2 mRNA is not expressed, and cells are prevented from entering S phase.

In one aspect, a tumor can optionally be treated before any other treatment with the combination of an HDACi and an antiviral agent. In some embodiments, the antiviral agent is acyclovir, ganciclovir, or valganciclovir. In some embodiments, the antiviral agent is valganciclovir. In certain embodiments, the antiviral is delivered at a dose of at least about 100 mg/day, 200 mg/day, 300 mg/day, 400 mg/day, 500 mg/day, 600 mg/day, 700 mg/day, 800 mg/day, 900 mg/day, 1000 mg/day, 1200 mg/day, 1400 mg/day, 1600 mg/day, 1800 mg/day, or 2000 mg/day. In certain embodiments, the antiviral is delivered at a dose between about 100 mg/day and about 2000 mg/day, between about 200 mg/day and about 1500 mg/day, between about 300 mg/day, and about 1200 mg/day, between about 500 mg/day, and about 1000 mg/day, between about 600 mg/day, and about 1000 mg/day, or between about 800 mg/day, and about 1000 mg/day. In certain embodiments, the dose is about 800, 825, 850, 875, 900, 925, 950, 975, or 1000 mg/day. The dose can be split up in any convenient way including once, twice, or three times daily to achieve the daily dose. In certain embodiments, the individual can be subjected to at least 1 week, 2 weeks, 3 weeks, 4 week, six week, eight weeks, or twelve weeks of treatment with HDACi and antiviral before treatment with an HDACi and an immunotherapy. In certain embodiments, treatment with HDACi and antiviral can be administered after treatment with HDACi and immunotherapy for at least 1 week, 2 weeks, 3 weeks, 4 week, six week, eight weeks, or twelve weeks.

The particular combination of HDAC inhibitor with an immunotherapeutic that is most effective against a specific disorder can be determined by one of ordinary skill in the art from empirical testing and, preferably, from a knowledge of each agent's mechanism of action. For example, many of the RNA viruses such as HIV and other retroviruses require a reverse transcriptase to transcribe their genome into DNA. A few of the agents that induce expression or activity of retroviruses and their encoded genes, such as, for example, reverse transcriptase, are known to those of ordinary skill in the art. Autologous cytolytic T cells which are specific for reverse transcriptase, and have been stimulated and expanded ex vivo, can be adoptively transferred to a patient. Another example utilizes the LMP-1 protein of EBV, which is expressed on the surface of B cells infected with EBV. A population of T cells with a chimeric antigen receptor targeting LMP-1 can be administered together with an HDAC inhibitor that increases expression of LMP-1. This can lead to increased efficacy of chimeric antigen receptor T cell by increasing expression of the amount of antigen on the cell. HDAC inhibitors also increase the expression of viral proteins that are intracellular, EBV thymidine kinase, for example. HDAC inhibitors can be combined with vaccination, autologous cytotoxic T cells, or chimeric antigen receptor T cells that have specificity for an antigen derived from an intracellular antigen in the context of MHC, and improve the overall effectiveness of these therapies. HDAC inhibitors can also increase the efficacy of an immunotherapeutic by reducing the expression of negative regulators or checkpoint regulators of the immune system such as PD-1 (CD279) or CTLA-4, which are expressed on T cells; or B7.1 (CD80), B7.2 (CD86), or PD-L1/PD-L2, which are expressed on antigen presenting cells. This can improve the efficacy of a vaccine by allowing for stronger immune priming or boosting of an immune response. Likewise, they can improve the efficacy of adoptive T cell therapy using either autologous or heterologous cells, by reducing negative feedback, which is propagated through these receptors. HDAC inhibitors can also act directly on the tumor cell by increasing the abundance of antigen expressed on their surface that can be targeted by an antibody leading to increased killing of a tumor cell by complement or antibody dependent cellular cytotoxicity.

In some embodiments, an HDAC inhibitor induces viral gene expression by more than 4 fold after 24 h of treatment. In certain embodiments, an HDAC inhibitor induces TK or EBV-PK expression by more than 4 fold after 24 h of treatment. In some embodiments, an HDAC inhibitor induces viral gene expression after about 48 h, about 36 h, about 24 h, about 18 h, about 12 h, about 8 h, about 6 h, about 4 h, about 3 h, about 2 h, about 1 h, or about 30 minutes. In certain embodiments, an HDAC inhibitor induces viral gene expression in less than 48 h, less than 36 h, less than 24 h, less than 18 h, less than 12 h, less than 8 h, less than 6 h, less than 4 h, less than 3 h, less than 2 h, less than 1 h, or less than 30 minutes. In some embodiments, an HDAC inhibitor induces viral gene expression in more than 48 h, more than 36 h, more than 24 h, more than 18 h, more than 12 h, more than 8 h, more than 6 h, more than 4 h, more than 3 h, more than 2 h, more than 1 h, or more than 30 minutes. In certain embodiments, an HDAC inhibitor induces viral gene expression after more than 30 minutes and less than 24 h.

In certain embodiments, an HDAC inhibitor is capable of inducing gene expression at a concentration of less than 500 nM. In some embodiments, the inducing agent is an HDAC inhibitor. In certain embodiments, the inducing agent is capable of inducing TK or EBV-PK expression. In certain embodiments, an inducing agent is capable of inducing gene expression at a concentration of about 100 μM, about 90 μM, about 80 μM, about 75 μM, about 70 μM, about 60 μM, about 50 μM, about 40 μM, about 30 μM, about 25 μM, about 20 μM, about 10 μM, about 5 μM, about 2 μM, about 1 μM, about 900 nM, about 800 nM, about 700 nM, about 600 nM, about 500 nM, about 400 nM, about 300 nM, about 200 nM, about 100 nM, about 75 nM, about 50 nM, about 20 nM, or about 10 nM. In some embodiments, an inducing agent is capable of inducing gene expression at a concentration of less than 100 μM, less than 90 μM, less than 80 μM, less than 75 μM, less than 70 μM, less than 60 μM, less than 50 μM, less than 40 μM, less than 30 μM, less than 25 μM, less than 20 μM, less than 10 μM, less than 5 μM, less than 2 μM, less than 1 μM, less than 900 nM, less than 800 nM, less than 700 nM, less than 600 nM, less than 500 nM, less than 400 nM, less than 300 nM, less than 200 nM, less than 100 nM, less than 75 nM, less than 50 nM, less than 20 nM, or less than 10 nM. In certain embodiments, an inducing agent is capable of inducing gene expression at a concentration of more than 100 μM, more than 90 μM, more than 80 μM, more than 75 μM, more than 70 μM, more than 60 μM, more than 50 μM, more than 40 μM, more than 30 μM, more than 25 μM, more than 20 μM, more than 10 μM, more than 5 μM, more than 2 μM, more than 1 μM, more than 900 nM, more than 800 nM, more than 700 nM, more than 600 nM, more than 500 nM, more than 400 nM, more than 300 nM, more than 200 nM, more than 100 nM, more than 75 nM, more than 50 nM, more than 20 nM, or more than 10 nM. In some embodiments, an inducing agent is capable of inducing gene expression at a concentration more than 50 nM and less than 100 nM. In certain embodiments, an inducing agent is capable of inducing gene expression at a concentration of more than 200 nM and less than 500 nM. In some embodiments, an inducing agent is capable of inducing gene expression at more than 100 nM and less than 200 nM.

In some embodiments, an HDAC inhibitor induces viral gene expression after more than 1 h and less than 6 h. In certain embodiments, an HDAC inhibitor induces viral gene expression about 2 fold, about 3 fold, about 4 fold, about 5 fold, about 6 fold, about 7 fold, about 8 fold, about 9 fold, about 10 fold, about 12 fold, about 15 fold, about 20 fold, about 25 fold, about 30 fold, about 35 fold, about 40 fold, about 45 fold, or about 50 fold. In some embodiments, an HDAC inhibitor induces viral gene expression less than 2 fold, less than 3 fold, less than 4 fold, less than 5 fold, less than 6 fold, less than 7 fold, less than 8 fold, less than 9 fold, less than 10 fold, less than 12 fold, less than 15 fold, less than 20 fold, less than 25 fold, less than 30 fold, less than 35 fold, less than 40 fold, less than 45 fold, or less than 50 fold. In certain embodiments, an HDAC inhibitor induces viral gene expression more than 2 fold, more than 3 fold, more than 4 fold, more than 5 fold, more than 6 fold, more than 7 fold, more than 8 fold, more than 9 fold, more than 10 fold, more than 12 fold, more than 15 fold, more than 20 fold, more than 25 fold, more than 30 fold, more than 35 fold, more than 40 fold, more than 45 fold, or more than 50 fold. In some embodiments, an HDAC inhibitor induces viral gene expression more than 2 fold and less than 50 fold. In certain embodiments, an HDAC inhibitor induces viral gene expression more than 5 fold and less than 40 fold.

In certain embodiments, the HDAC inhibitor can induce expression of the UL1, UL2, UL3, UL4, UL5, UL6, UL7, UL8, UL9, UL10, UL11, UL12, UL13, UL14, UL15, UL16, UL17, UL18, UL19, UL20, UL21, UL22, UL23, UL24, UL25, UL26, UL27, UL28, UL29, UL30, UL31, UL32, UL33, UL34, UL35, UL36, UL37, UL38, UL39, UL40, UL41, UL42, UL43, UL44, UL45, UL46, UL47, UL48, UL49, UL50, UL51, UL52, UL53, UL54, UL55, UL56, US1, US2, US3, US4, US5, US6, US7, US8, US9, US10, US11, US12, RS1, ICP0, LRP1, LRP2, RL1, or LAT gene of HSV. In certain embodiments, the HDAC inhibitor can induce expression of the BDLF1, BFRF3, BORF1, BBRF1, BdRF1, BLLF1, BXLF2, BALF4, BALF4, BZLF2, BBRF3, BILF2, BLRF1, BDLF3, BKRF2, BMRF2, BPLF1, BGLF2, BOLF1, BVRF1, BBLF1, BGLF1, BSRF1, BGLF4, BNRF1, BLRF2, BRRF2, BDLF2, BKRF4, BORF2, BALF2, BXLF1, BMRF1, EBNA-1, EBNA-2, EBNA-3A, EBNA-3B, EBNA-3C, EBNA-LP, LMP-1, LMP-2A, LMP-2B, BNLF2, BZLF1 or BRLF1 gene of EBV. In certain embodiments, the HDAC inhibitor can induce expression of the US1, US10, US11, US12, US2, US3, US6, US7, US8, US9, IRS1, RL1, RL10, RL11, RL12, RL13, RL2, RL4, RL6, RL9, TRS1, UL10, UL100, UL102, UL103, UL104, UL105, UL108, UL109, UL11, UL110, UL111a, UL112, UL113, UL114, UL115, UL116, UL117, UL119, UL12, UL121, UL122, UL123, UL124, UL127, UL129, UL13, UL130, UL132, UL14, UL146, UL147, UL15, UL16, UL17, UL18, UL19, UL2, UL20, UL20a, UL21, UL23, UL24, UL25, UL26, UL27, UL28, UL29, UL3, UL30, UL31, UL32, UL33, UL34, UL35, UL36, UL37.1, UL37.3, UL38, UL39, UL4, UL42, UL43, UL44, UL45, UL46, UL47, UL48, UL48.5, UL49, UL5, UL50, UL51, UL52, UL53, UL54, UL55, UL56, UL57, UL59, UL6, UL60, UL62, UL64, UL65, UL67, UL69, UL7, UL70, UL71, UL72, UL73, UL74, UL75, UL76, UL77, UL78, UL79, UL8, UL80, UL82, UL83, UL84, UL85, UL86, UL87, UL88, UL89.1, UL89.2, UL9, UL90, UL91, UL92, UL93, UL94, UL95, UL96, UL97, UL98, UL99, US13, US14, US15, US16, US17, US18, US19, US20, US21, US22, US23, US24, US25, US26, US27, US28, US29, US30, US31, US32, US33, or US34 gene of CMV. In certain embodiments, the HDAC inhibitor can induce expression of the gag, pol, env, tat, rev, nef, vpr, vif or vpu gene of HIV.

In certain embodiments, the HDAC inhibitor alters the expression of immune costimulatory molecules or checkpoint regulators on the surface of a cell. By altering expression of a costimulatory molecule which is a positive regulator, an HDAC would augment therapy by increasing the efficacy of immunotherapies that rely on costimulation or priming, such as vaccines. HDAC inhibitors can also affect transcription/cell surface expression of negative inhibitors known as checkpoint inhibitors. Checkpoint inhibitors expressed on a tumor cell (e.g., PDL-1 or PDL-2) engage with their ligands on immune effector cells (e.g., PD-1 on T cells) to restrain an immune response. When expressed on tumors or chronically infected cells, this engagement allows these cells to escape immune surveillance and reduces the effect of immunotherapies such as treatment with adoptively transferred immune cells or antibodies specific for tumor associated antigens.

Checkpoint molecules are molecules that function in the immune system to increase or decrease an immune response. Checkpoint molecules that increase the immune response include, for example, CD27, CD28, ICOS CD40, OX40, GITR, CD122, and CD137. Checkpoint molecules that decrease the immune response (e.g., checkpoint inhibitors) include, for example, CTLA4, PD-1, PDL-1, PDL-2, TIM-3, VISTA, KIR, IDO, A2AR, B7-H3, B7-H4, BTLA, TIGIT, or CD155. The methods described herein include administration of an HDAC inhibitor in conjunction with a molecule (e.g., antibody, polypeptide, or small molecule) that antagonizes a checkpoint inhibitor's activity. In certain embodiments, the checkpoint inhibitor is an antibody or polypeptide that binds PD-L1, PD-L2, CTLA-4, or PD-1. In certain embodiments, the HDAC inhibitor comprises CHR-3996 (VRx-3996). In a certain embodiment, the method comprises administration of CHR-3996 (VRx-3996) and an anti-PD-1 antibody. In a certain embodiment, the method comprises administration of CHR-3996 (VRx-3996) and an anti-PD-L1 antibody. In a certain embodiment, the method comprises administration of CHR-3996 (VRx-3996) and an anti-PD-L2 antibody. In certain embodiments, the anti PD-1 antibody is nivolumab, pembrolizumab, pidilizumab, or any combination thereof. In certain embodiments, the anti PD-1 binding polypeptide is AMP-514, AUNP-12, or any combination thereof.

In certain embodiments, the HDAC inhibitor increases expression of negative immune regulators or checkpoint inhibitors allowing increased efficacy of checkpoint inhibitor antagonist molecules and antibodies. In certain embodiments, the checkpoint inhibitor is PD-1. In certain embodiments, the checkpoint inhibitor is CTLA-4. In certain embodiments, the checkpoint inhibitor is PD-L1. In certain embodiments, the checkpoint inhibitor is PD-L2. In certain embodiments, the checkpoint inhibitor is TIM-3. In certain embodiments, the checkpoint inhibitor is VISTA. In certain embodiments, the checkpoint inhibitor is KIR. In certain embodiments, the checkpoint inhibitor is IDO. In certain embodiments, the checkpoint inhibitor is A2AR. In certain embodiments, the checkpoint inhibitor is B7-H3. In certain embodiments, the checkpoint inhibitor is B7-H4. In certain embodiments, the checkpoint inhibitor is BTLA. In certain embodiments, the checkpoint inhibitor is CD155. The HDAC inhibitor can increase checkpoint inhibitor expression by a cancerous or latently infected cell by at least 25%, 50%, 75%, 100, 200%, 300% or more compared to a the same cell treated with vehicle alone.

In certain embodiments, the HDAC inhibitor decreases expression of negative immune regulators or checkpoint inhibitors. In certain embodiments, the checkpoint inhibitor is PD-1. In certain embodiments, the checkpoint inhibitor is CTLA-4. In certain embodiments, the checkpoint inhibitor is PD-L1. In certain embodiments, the checkpoint inhibitor is PD-L2. In certain embodiments, the checkpoint inhibitor is TIM-3. In certain embodiments, the checkpoint inhibitor is VISTA. In certain embodiments, the checkpoint inhibitor is KIR. In certain embodiments, the checkpoint inhibitor is IDO. In certain embodiments, the checkpoint inhibitor is A2AR. In certain embodiments, the checkpoint inhibitor is B7-H3. In certain embodiments, the checkpoint inhibitor is B7-H4. In certain embodiments, the checkpoint inhibitor is BTLA. In certain embodiments, the checkpoint inhibitor is TIGIT. In certain embodiments, the checkpoint inhibitor is CD155. The HDAC inhibitor can decrease checkpoint inhibitor expression by a cancerous or latently infected cell by at least 10%, 20%, 30%, 40%, 50, 60%, 70% or more compared to a the same cell treated with vehicle alone.

In certain embodiments, the HDAC inhibitor increases expression of positive immune regulators. In certain embodiments, the positive regulator is CD28. In certain embodiments, the positive regulator is CD40. In certain embodiments, the positive regulator is CD40L. In certain embodiments, the positive regulator is OX40. In certain embodiments, the positive regulator is 40L. In certain embodiments, the positive regulator is ICOS. In certain embodiments, the positive regulator is ICOS-L. In certain embodiments, the positive regulator is B7.1. In certain embodiments, the positive regulator is B7.2. The HDAC inhibitor can increase positive immune regulator expression by a cancerous or latently infected cell by at least 25%, 50%, 75%, 100, 200%, 300% or more compared to a the same cell treated with vehicle alone.

Immune responses are negatively regulated by CD4+ T regulatory cells. Reduction of CD4+ Tregs is an important strategy for increasing therapeutic responses to immune therapies. FoxP3 is a transcriptional regulator of regulatory T cell phenotypes. In certain embodiments, the HDAC inhibitors described herein reduce FoxP3+, CD4+ T regulatory cell populations. In certain embodiments, the HDAC inhibitors described herein reduce FoxP3+, CD4+ T regulatory cell populations by at least 10%, 20%, 30%, 40%, 50, 60%, 70% or more. These T cell populations can be reduced in an induvial after dosing with an HDAC inhibitor but prior to immunotherapy. In certain embodiments, the HDAC inhibitors described herein reduce FoxP3+, CD4+ T regulatory cell populations by at least 10%, 20%, 30%, 40%, 50, 60%, 70%, 80%, 90%, 95% or more in an induvial treated with HDAC inhibitor compared to a placebo treated individual. In certain embodiments, the HDAC inhibitors described herein reduce FoxP3+, CD4+ T regulatory cell populations by at least 10%, 20%, 30%, 40%, 50, 60%, 70% or more in in ex vivo cultured peripheral blood mononuclear cells compared to PBMC treated with a vehicle control or left untreated.

Immunotherapeutic Agents

In certain embodiments, the immunotherapeutic agent leads to immune system activation of an individual. In certain embodiments, the immunotherapeutic agent is a biologic drug. In certain embodiments, the immunotherapeutic agent is a cytokine. In certain embodiments, the immunotherapeutic agent is a chemokine. In certain embodiments, the immunotherapeutic agent binds to and antagonizes a checkpoint inhibitor. In certain embodiments, the immunotherapeutic agent is an antibody. In certain embodiments, the immunotherapeutic agent is a monoclonal antibody. In certain embodiments, the immunotherapeutic agent is a humanized monoclonal antibody. In certain embodiments, the immunotherapeutic agent is an antibody-drug conjugate. In certain embodiments, the immunotherapeutic agent is a bispecific antibody. In certain embodiments, the immunotherapeutic agent is a vaccine. In certain embodiments, the immunotherapeutic agent is an antigen presenting cell. In certain embodiments, the immunotherapeutic agent is a dendritic cell. In certain embodiments, the immunotherapeutic agent is B cell. In certain embodiments, the immunotherapeutic agent is a macrophage. In certain embodiments, the immunotherapeutic agent is a T cell. In certain embodiments, the immunotherapeutic agent is a gamma-delta T cell. In certain embodiments, the immunotherapeutic agent is a CD8+ T cell. In certain embodiments, the immunotherapeutic agent is a CD4+ T cell. In certain embodiments, the immunotherapeutic agent is an autologous T cell. In certain embodiments, the immunotherapeutic agent is a heterologous T cell. In certain embodiments, the immunotherapeutic agent is a T cell with a genetically modified antigen receptor. In certain embodiments, the immunotherapeutic agent is a chimeric antigen receptor. In certain embodiments, the immunotherapeutic agent is a T cell with a chimeric antigen receptor. In certain embodiments, the immunotherapeutic agent is specific for a virus encoded polypeptide. In certain embodiments, the immunotherapeutic agent is specific for an EBV encoded polypeptide. In certain embodiments, the immunotherapeutic agent is specific for LMP-1. In certain embodiments, the immunotherapeutic agent is specific for LMP-2. In certain embodiments, the immunotherapeutic is *Bacillus* Calmette-Guérin.

In certain embodiments, the immunotherapeutic agent is a checkpoint inhibitor antagonist. This antagonist can be an antibody, a binding molecule (e.g., a DNA fragment or an aptamer), or a small molecule inhibitor. In certain embodiments, the checkpoint inhibitor antagonist is a PD-1 antibody. In certain embodiments, the checkpoint inhibitor antagonist is a CTLA-4 antibody. In certain embodiments, the checkpoint inhibitor antagonist is a PD-L1 antibody. In certain embodiments, the checkpoint inhibitor antagonist is a PD-L2 antibody. In certain embodiments, the checkpoint inhibitor antagonist is a TIM-3 antibody. In certain embodiments, the checkpoint inhibitor is a VISTA antibody. In certain embodiments, the checkpoint inhibitor is a KIR antibody. In certain embodiments, the checkpoint inhibitor is an IDO antibody. In certain embodiments, the checkpoint inhibitor is an A2AR antibody. In certain embodiments, the checkpoint inhibitor is a B7-H3 antibody. In certain embodiments, the checkpoint inhibitor is a B7-H4 antibody. In certain embodiments, the checkpoint inhibitor is a BTLA antibody. In certain embodiments, the checkpoint inhibitor is a TIGIT antibody. In certain embodiments, the checkpoint inhibitor is a CD155 antibody. In certain embodiments, the checkpoint inhibitor antagonist is an inhibitor of the HIPPO signaling pathway.

In certain embodiments, the immunotherapeutic agent is a monoclonal antibody. In certain embodiments, the monoclonal antibody is Lambrolizumab, Dupilumab, Tabalumab, Galiximab, Pritumumab, Trastuzumab, Amatuximab, Coltuximab ravtansine, Ensituximab, Indatuximab ravtansine, Isatuximab, Mirvetuximab soravtansine, Siltuxima, Ublituximab, Zatuximab, Ontuxizumab, Pasotuxizumab, Anetumab ravtansine, Ascrinvacumab, Conatumumab, Daratumumab, Durvalumab, Dusigitumab, Elgemtumab, Ganitumab, Imalumab, Indusatumab vedotin, Lexatumumab, Mapatumumab, Narnatumab, Nesvacumab, Nivolumab, Olaratum, Parsatuzumab, Patritumab, Radretumab, Robatumuma, Seribantumab, Tarextumab, Ticilimumab (tremelimumab), Tovetumab, Tremelimumab, Vantictumab, Abituzumab, Alacizumab pegol, Atezolizumab, cBR96-doxorubicin immunoconjugate, Codrituzumab, Demcizumab, Denintuzumab mafodotin, Emactuzumab, Emibetuzumab, Enoblituzumab, Imgatuzumab, Inotuzumab ozogamicin, Lifastuzumab vedotin, Lintuzuma, Lorvotuzumab mertansin, Lumretuzumab, Margetuximab, Mogamulizumab, Ocaratuzumab, Onartuzumab, Oportuzumab monatox, Otlertuzumab, Pertuzumab, Pinatuzumab vedotin, Polatuzumab vedotin, Sacituzumab govitecan, Samalizumab, Sibrotuzumab, Tacatuzumab tetraxetan, Tigatuzumab, Tucotuzumab celmoleukin, Vandortuzumab vedotin, Vanucizumab, Vorsetuzumab mafodotin, Pidilizumab, Drozitumab, Icrucumab, Urelumab, Dalotuzumab, Enavatuzumab, Ficlatuzumab, Pembrolizumab, Enfortumab vedotin, Bavituximab, Epratuzumab, Cantuzumab ravtansine, Sonepcizumab, Tuvirumab, Lumiliximab, Ofatumumab, TGN1412, Girentuximab, Panitumumab, Labetuzumab, Cantuzumab mertansine, Votumumab, Matuzumab, Regavirumab, Sevirumab, Otelixizumab, IMAB362, Brentuximab vedotin, Dacetuzumab, Ulocuplumab, Teprotumumab, Apolizumab, Atorolimumab, Iratumumab, TNX-650, Afutuzumab, Rituximab, Ecromeximab, TRBS07, Flanvotumab, Ipilimumab, Glembatumumab vedotin, Etaracizumab, Bevacizumab, Cetuximab, Elotuzumab, Milatuzumab, Lucatumumab, Dinutuximab, Belimumab, Veltuzumab, Necitumumab, Carlumab, Romosozumab, Denosumab, Farletuzumab, Pankomab, Sofituzumab vedotin, Citatuzumab bogatox, Clivatuzumab tetraxetan, Abciximab, Daclizumab, Basiliximab, Adecatumumab, Derlotuximab biotin, Ruplizumab, Clenoliximab, Canakinumab, Fletikumab, Mavrilimumab, Sirukumab, ALD518, Atlizumab (tocilizumab), Clazakizumab, Infliximab, Ocrelizumab, Zanolimumab, Golimumab, Sarilumab, Adalimumab, Fezakinumab, Volociximab, Cixutumumab, Ramucirumab, Rilotumumab, Intetumumab, Bivatuzumab mertansine, Zalutumumab, Nimotuzumab, Anifrolumab, Rontalizumab, Metelimumab, Alemtuzumab, or Pateclizumab. In certain embodiments, the monoclonal antibody is BMS-936559, MSB0010718C, or MEDI4736.

In certain embodiments, the dosage of monoclonal antibody is less than 10 mg daily. In certain embodiments, the dosage of monoclonal antibody is less than 9 mg daily. In certain embodiments, the dosage of monoclonal antibody is less than 8 mg daily. In certain embodiments, the dosage of monoclonal antibody is less than 7 mg daily. In certain embodiments, the dosage of monoclonal antibody is less than 6 mg daily. In certain embodiments, the dosage of monoclonal antibody is less than 5 mg daily. In certain embodiments, the dosage of monoclonal antibody is less than 4 mg daily. In certain embodiments, the dosage of monoclonal antibody is less than 3 mg daily. In certain embodiments, the dosage of monoclonal antibody is less than 2 mg daily. In certain embodiments, the dosage of monoclonal antibody is less than 1 mg daily. In certain embodiments, the dosage of monoclonal antibody is less than 0.5 mg daily. In certain embodiments, the dosage of monoclonal antibody is less than 20 mg weekly. In certain embodiments, the dosage of monoclonal antibody is less than 15 mg weekly. In certain embodiments, the dosage of monoclonal antibody is less than 10 mg weekly. In certain embodiments, the dosage of monoclonal antibody is less than 9 mg weekly. In certain embodiments, the dosage of monoclonal antibody is less than 8 mg weekly. In certain embodiments, the dosage of monoclonal antibody is less than 7 mg weekly. In certain embodiments, the dosage of monoclonal antibody is less than 6 mg weekly. In certain embodiments, the dosage of monoclonal antibody is less than 5 mg weekly. In certain embodiments, the dosage of monoclonal antibody is less than 4 mg weekly. In certain embodiments, the dosage of monoclonal antibody is less than 3 mg weekly. In certain embodiments, the dosage of monoclonal antibody is less than 2 mg weekly. In certain embodiments, the monoclonal antibody is delivered intravenously. In certain embodiments, the monoclonal antibody is delivered directly to the tumor site.

In certain embodiments, the immunotherapeutic agent is a cytokine. In certain embodiments, the cytokine is an interferon. In certain embodiments, the cytokine is interferon alpha. In certain embodiments, the cytokine is interferon beta. In certain embodiments, the cytokine is interferon gamma. In certain embodiments, the cytokine is an interleukin. In certain embodiments, the cytokine is interleukin 1. In certain embodiments, the cytokine is interleukin 2. In certain embodiments, the cytokine is a hematopoietic growth factor.

In certain embodiments, the immunotherapeutic agent is a vaccine. The vaccines provided herein include typical vaccines that comprise an inactivated or attenuated virus, a whole-cell bacterial preparation, or an acellular preparation of purified bacterial or viral antigens. In certain embodiments, the antigen comprises 1 or more synthesized, purified, or isolated polypeptides. In certain embodiments, the polypeptide is a viral peptide. In certain embodiments, the viral polypeptide is from EBV. In certain embodiments, the viral polypeptide is from CMV. In certain embodiments, the viral polypeptide is from HHV8. In certain embodiments, the vaccine comprises 1 or more synthesized, purified, or isolated proteins. In certain embodiments, the protein is a viral protein. In certain embodiments, the viral protein is from EBV. In certain embodiments, the viral protein is from CMV. In certain embodiments, the viral protein is from HHV8. In certain embodiments, the bacterial antigen is from a bacteria that is capable of establishing a persistent viral infection. In certain embodiments, the bacterial antigen is from *Mycobacterium tuberculosis, Mycobacterium leprae, Helicobacter pylori*, or a *Borrelia* bacteria. In certain embodiments, the vaccine is cell based. In certain embodiments, the vaccine is antigen presenting cell based. In certain embodiments, the vaccine is cell based. In certain embodiments, the vaccine is dendritic cell based. In certain embodiments, the vaccine is B cell based.

In certain embodiments, the vaccine can comprise proteins, protein fragments, polypeptides or peptides derived from viral or bacterial genes. In certain embodiments, the protein, protein fragment, polypeptide or peptide is derived from the UL1, UL2, UL3, UL4, UL5, UL6, UL7, UL8, UL9, UL10, UL11, UL12, UL13, UL14, UL15, UL16, UL17, UL18, UL19, UL20, UL21, UL22, UL23, UL24, UL25, UL26, UL27, UL28, UL29, UL30, UL31, UL32, UL33, UL34, UL35, UL36, UL37, UL38, UL39, UL40, UL41, UL42, UL43, UL44, UL45, UL46, UL47, UL48, UL49, UL50, UL51, UL52, UL53, UL54, UL55, UL56, US1, US2, US3, US4, US5, US6, US7, US8, US9, US10, US11, US12, RS1, ICP0, LRP1, LRP2, RL1, or LAT gene of HSV. In certain embodiments, the protein, protein fragment, polypeptide, or peptide is derived from the BDLF1, BFRF3, BORF1, BBRF1, BdRF1, BLLF1, BXLF2, BALF4, BALF4, BALF4, BZLF2, BBRF3, BILF2, BLRF1, BDLF3, BKRF2, BMRF2, BPLF1, BGLF2, BOLF1, BVRF1, BBLF1, BGLF1, BSRF1, BGLF4, BNRF1, BLRF2, BRRF2, BDLF2, BKRF4, BORF2, BALF2, BXLF1, BMRF1, EBNA-1, EBNA-2, EBNA-3A, EBNA-3B, EBNA-3C, EBNA-LP, LMP-1, LMP-2A, LMP-2B, BNLF2, BZLF1, or BRLF1 gene of EBV. In certain embodiments, the protein, protein fragment, polypeptide, or peptide is derived from the US1, US10, US 11, US12, US2, US3, US6, US7, US8, US9, IRS1, RL1, RL10, RL11, RL12, RL13, RL2, RL4, RL6, RL9, TRS1, UL10, UL100, UL102, UL103, UL104, UL105, UL108, UL109, UL11, UL110, UL111a, UL112, UL113, UL114, UL115, UL116, UL117, UL119, UL12, UL121, UL122, UL123, UL124, UL127, UL129, UL13, UL130, UL132, UL14, UL146, UL147, UL15, UL16, UL17, UL18, UL19, UL2, UL20, UL20a, UL21, UL23, UL24, UL25, UL26, UL27, UL28, UL29, UL3, UL30, UL31, UL32, UL33, UL34, UL35, UL36, UL37.1, UL37.3, UL38, UL39, UL4, UL42, UL43, UL44, UL45, UL46, UL47, UL48, UL48.5, UL49, UL5, UL50, UL51, UL52, UL53, UL54, UL55, UL56, UL57, UL59, UL6, UL60, UL62, UL64, UL65, UL67, UL69, UL7, UL70, UL71, UL72, UL73, UL74, UL75, UL76, UL77, UL78, UL79, UL8, UL80, UL82, UL83, UL84, UL85, UL86, UL87, UL88, UL89.1, UL89.2, UL9, UL90, UL91, UL92, UL93, UL94, UL95, UL96, UL97, UL98, UL99, US13, US14, US15, US16, US17, US18, US19, US20, US21, US22, US23, US24, US25, US26, US27, US28, US29, US30, US31, US32, US33, or US34 gene of CMV. In certain embodiments, the protein, protein fragment, polypeptide, or peptide is derived from the gag, pol, env, tat, rev, nef, vpr, vif or vpu gene of HIV.

In certain embodiments, the immunotherapeutic agent is a T cell. The T cell can be an alpha-beta T cell, or a gamma-delta T cell. T cells can be stimulated expanded in vitro and adoptively transferred to an individual in need thereof. Adoptively transferred T cells can be a patients own T cells (e.g., autologous), or derived from an individual other than the patient (e.g., heterologous). These cells can be expanded or stimulated in the presence of antigen and one or more cytokines. Optionally these cells can be treated with an HDAC inhibitor to reduce suppressive T cell phenotypes (e.g., IL-10 secreting T cells or FoxP3+ T cells). In certain embodiments, the HDAC inhibitor comprises (2-(6-{[(6-Fluoroquinolin-2-yl)methyl]amino}-3-azabicyclo[3.1.0]hex-3-yl)-N-hydroxypyrimidine-5-carboxamide). In certain embodiments, the T cell has been genetically modified. In certain embodiments, the T cell is autologous to the individual being treated. In certain embodiments, the T cell is heterologous (allogeneic) to the individual being treated.

In certain embodiments, the T cell expresses a chimeric antigen receptor (a CART cell). A CART cell is a cell line that expresses a cell surface polypeptide comprising an antigen binding moiety (targeting domain), a transmembrane domain, and an intracellular signaling domain that potentiates T cell effector function. In certain embodiments, the CAR T cell has a targeting domain comprising amino acid residues derived from an antibody molecule. In certain embodiments, the targeting domain is specific for the α-Folate receptor, CAIX, CD19, CD20, CD22, CD30, CD33, CD44v7/8, CEA, EGP-2, EGP-40, erb-B2, erb-B 2,3,4, FBP, Fetal acetylcholine receptor, GD2, GD3, Her2/neu, IL-13R-a2, KDR, kappa-light chain, LeY, L1 cell adhesion molecule, MAGE-A1, Mesothelin, Murine CMV infected cells, MUC1, NKG2D ligands, Oncofetal antigen (h5T4), PSCA, PSMA, TAA targeted by mAb IgE, TAG-72, or VEGF-R2. In certain embodiments, the CAR T cell has a targeting receptor comprising a signaling domain. In certain embodiments, the signaling domain comprises CD3, CD28, OX40, 41-BB, ZAP70, PI3K, TRAF2, or CD 137. In certain embodiments, the targeting domain is specific for a virally or bacterially associated antigen, such as a polypeptide expressed by the bacteria of virus. In a certain embodiment, the CART cell is a universal CART cell. Universal CART cells are allogeneic cells that have been engineered for use with multiple different individuals.

In certain embodiments, the CART cell has a targeting receptor that is specific for a protein, protein fragment, polypeptide, or peptide derived from a viral gene. In certain embodiments, the protein, protein fragment, polypeptide, or peptide is derived from the UL1, UL2, UL3, UL4, UL5, UL6, UL7, UL8, UL9, UL10, UL11, UL12, UL13, UL14, UL15, UL16, UL17, UL18, UL19, UL20, UL21, UL22, UL23, UL24, UL25, UL26, UL27, UL28, UL29, UL30, UL31, UL32, UL33, UL34, UL35, UL36, UL37, UL38, UL39, UL40, UL41, UL42, UL43, UL44, UL45, UL46, UL47, UL48, UL49, UL50, UL51, UL52, UL53, UL54, UL55, UL56, US1, US2, US3, US4, US5, US6, US7, US8, US9, US10, US 11, US12, RS1, ICP0, LRP1, LRP2, RL1, or LAT gene of HSV. In certain embodiments, the protein, protein fragment, polypeptide, or peptide is derived from the BDLF1, BFRF3, BORF1, BBRF1, BdRF1, BLLF1, BXLF2, BALF4, BALF4, BALF4, BZLF2, BBRF3, BILF2, BLRF1, BDLF3, BKRF2, BMRF2, BPLF1, BGLF2, BOLF1, BVRF1, BBLF1, BGLF1, BSRF1, BGLF4, BNRF1, BLRF2, BRRF2, BDLF2, BKRF4, BORF2, BALF2, BXLF1, BMRF1, EBNA-1, EBNA-2, EBNA-3A, EBNA-3B, EBNA-3C, EBNA-LP, LMP-1, LMP-2A, LMP-2B, BNLF2, BZLF1, or BRLF1 gene of EBV. In certain embodiments, the protein, protein fragment, polypeptide, or peptide is derived from the US1, US10, US 11, US12, US2, US3, US6, US7, US8, US9, IRS1, RL1, RL10, RL11, RL12, RL13, RL2, RL4, RL6, RL9, TRS1, UL10, UL100, UL102, UL103, UL104, UL105, UL108, UL109, UL11, UL110, UL111a, UL112, UL113, UL114, UL115, UL116, UL117, UL119, UL12, UL121, UL122, UL123, UL124, UL127, UL129, UL13, UL130, UL132, UL14, UL146, UL147, UL15, UL16, UL17, UL18, UL19, UL2, UL20, UL20a, UL21, UL23, UL24, UL25, UL26, UL27, UL28, UL29, UL3, UL30, UL31, UL32, UL33, UL34, UL35, UL36, UL37.1, UL37.3, UL38, UL39, UL4, UL42, UL43, UL44, UL45, UL46, UL47, UL48, UL48.5, UL49, UL5, UL50, UL51, UL52, UL53, UL54, UL55, UL56, UL57, UL59, UL6, UL60, UL62, UL64, UL65, UL67, UL69, UL7, UL70, UL71, UL72, UL73, UL74, UL75, UL76, UL77, UL78, UL79, UL8, UL80, UL82, UL83, UL84, UL85, UL86, UL87, UL88, UL89.1, UL89.2, UL9, UL90, UL91, UL92, UL93, UL94, UL95, UL96, UL97, UL98, UL99, US13, US14, US15, US16, US17, US18, US19, US20, US21, US22, US23, US24, US25, US26, US27, US28, US29, US30, US31, US32, US33, or US34 gene of CM. In certain embodiments, the protein, protein fragment, polypeptide, or peptide is derived from the gag, pol, env, tat, rev, nef vpr, vif, or vpu gene of HIV.

In certain embodiments, the CART cells are administered by i.v. infusion. In certain embodiments, about $1\times10^5$ cells/m$^2$ are administered. In certain embodiments, about $2\times10^5$ cells/m$^2$ are administered. In certain embodiments, about $3\times10^5$ cells/m$^2$ are administered. In certain embodiments, about $4\times10^5$ cells/m$^2$ are administered. In certain embodiments, about $5\times10^5$ cells/m$^2$ are administered. In certain embodiments, about $6\times10^5$ cells/m$^2$ are administered. In certain embodiments, about $7\times10^5$ cells/m$^2$ are administered. In certain embodiments, about $8\times10^5$ cells/m$^2$ are administered. In certain embodiments, about $9\times10^5$ cells/m$^2$ are administered. In certain embodiments, about $1\times10^6$ cells/m$^2$ are administered. In certain embodiments, about $2\times10^6$ cells/m$^2$ are administered. In certain embodiments, about $3\times10^6$ cells/m$^2$ are administered. In certain embodiments, about $4\times10^6$ cells/m$^2$ are administered. In certain embodiments, about $5\times10^6$ cells/m$^2$ are administered. In certain embodiments, about $6\times10^6$ cells/m$^2$ are administered. In certain embodiments, about $7\times10^6$ cells/m$^2$ are administered. In certain embodiments, about $8\times10^6$ cells/m$^2$ are administered. In certain embodiments, about $9\times10^6$ cells/m$^2$ are administered. In certain embodiments, about $1\times10^7$ cells/m$^2$ are administered. In certain embodiments, about $2\times10^7$ cells/m$^2$ are administered. In certain embodiments, about $3\times10^7$ cells/m$^2$ are administered. In certain embodiments, about $4\times10^7$ cells/m$^2$ are administered. In certain embodiments, about $5\times10^7$ cells/m$^2$ are administered. In certain embodiments, about $6\times10^7$ cells/m$^2$ are administered. In certain embodiments, about $7\times10^7$ cells/m$^2$ are administered. In certain embodiments, about $8\times10^7$ cells/m$^2$ are administered. In certain embodiments, about $9\times10^7$ cells/m$^2$ are administered.

In certain embodiments, CAR T cells are administered once a day. In certain embodiments, CAR T cells are administered once a week. In certain embodiments, CAR T cells are administered once a month. In certain embodiments, CAR T cells are administered twice a week. In certain embodiments, CAR T cells are administered twice a month. In certain embodiments, CAR T cells are administered thrice a week. In certain embodiments, CAR T cells are administered thrice a month. In certain embodiments, CAR T cells are administered 4 times a month.

In certain embodiments, the immunotherapy is a small molecule that sensitizes tumors to killing by immune cells. In certain embodiments, the immunotherapy is a proteasome inhibitor. In certain embodiments, the immunotherapy is bortezomib, carfilzomib, or ixazomib. In certain embodiments, the immunotherapy is azacitidine.

Cancers

In certain embodiments, the methods of this disclosure are for the treatment of cancer. In certain embodiments, the methods of this disclosure are for augmenting the treatment of cancer. In certain embodiments, the cancer is Acute Lymphoblastic Leukemia, Adult; Acute Lymphoblastic Leukemia, Childhood; Acute Myeloid Leukemia, Adult; Acute Myeloid Leukemia, Childhood; Adreno cortical Carcinoma; Adrenocortical Carcinoma, Childhood; Adolescents, Cancer in; AIDS-Related Cancers; AIDS-Related Lymphoma; Anal Cancer; Appendix Cancer; Astrocytomas, Childhood; Atypical Teratoid/Rhabdoid Tumor, Childhood, Central Nervous System; Basal Cell Carcinoma; Bile Duct Cancer, Extrahepatic; Bladder Cancer; Bladder Cancer, Childhood; Bone Cancer, Osteosarcoma and Malignant Fibrous Histiocytoma; Brain Stem Glioma, Childhood; Brain Tumor, Adult; Brain Tumor, Brain Stem Glioma, Childhood; Brain Tumor, Central Nervous System Atypical Teratoid/Rhabdoid Tumor, Childhood; Brain Tumor, Central Nervous System Embryonal Tumors, Childhood; Brain Tumor, Astro cytomas, Childhood; Brain Tumor, Craniopharyngioma, Childhood; Brain Tumor, Ependymoblastoma, Childhood; Brain Tumor, Ependymoma, Childhood; Brain Tumor, Medulloblastoma, Childhood; Brain Tumor, Medulloepithelioma, Childhood; Brain Tumor, Pineal Parenchymal Tumors of Intermediate Differentiation, Childhood; Brain Tumor, Supratentorial Primitive Neuro ectodermal Tumors and Pineoblastoma, Childhood; Brain and Spinal Cord Tumors, Childhood (Other); Breast Cancer; Breast Cancer and Pregnancy; Breast Cancer, Childhood; Breast Cancer, Male; Bronchial Tumors, Childhood; Burkitt Lymphoma; Carcinoid Tumor, Childhood; Carcinoid Tumor, Gastrointestinal; Carcinoma of Unknown Primary; Central Nervous System Atypical Teratoid/Rhabdoid Tumor, Childhood; Central Nervous System Embryonal Tumors, Childhood; Central Nervous System (CNS) Lymphoma, Primary; Cervical Cancer; Cervical Cancer, Childhood; Childhood Cancers; Chordoma, Childhood; Chronic Lymphocytic Leukemia; Chronic Myelogenous Leukemia; Chronic Myeloproliferative Disorders; Colon Cancer; Colorectal Cancer, Childhood; Craniopharyngioma, Childhood; Cutaneous T-Cell Lymphoma; Embryonal Tumors, Central Nervous System, Childhood; Endometrial Cancer; Ependymoblastoma, Childhood; Ependymoma, Childhood; Esophageal Cancer; Esophageal Cancer, Childhood; Esthesioneuroblastoma, Childhood; Ewing Sarcoma Family of Tumors; Extracranial Germ Cell Tumor, Childhood; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer, Childhood; Gastrointestinal Carcinoid Tumor; Gastrointestinal Stromal Tumor (GIST); Gastrointestinal Stromal Cell Tumor, Childhood; Germ Cell Tumor, Extracranial, Childhood; Germ Cell Tumor, Extragonadal; Germ Cell Tumor, Ovarian; Gestational Trophoblastic Tumor; Glioma, Adult; Glioma, Childhood Brain Stem; Hairy Cell Leukemia; Head and Neck Cancer; Heart Cancer, Childhood; Hepatocellular (Liver) Cancer, Adult (Primary); Hepatocellular (Liver) Cancer, Childhood (Primary); Histiocytosis, Langerhans Cell; Hodgkin Lymphoma, Adult; Hodgkin Lymphoma, Childhood; Hypopharyngeal Cancer; Intraocular Melanoma; Islet Cell Tumors (Endocrine Pancreas); Kaposi Sarcoma; Kidney (Renal Cell) Cancer; Kidney Cancer, Childhood; Langerhans Cell Histiocytosis; Laryngeal Cancer; Laryngeal Cancer, Childhood; Leukemia, Acute Lymphoblastic, Adult; Leukemia, Acute Lymphoblastic, Childhood; Leukemia, Acute Myeloid, Adult; Leukemia, Acute Myeloid, Childhood; Leukemia, Chronic Lymphocytic; Leukemia, Chronic Myelogenous; Leukemia, Hairy Cell; Lip and Oral Cavity Cancer; Liver Cancer, Adult (Primary); Liver Cancer, Childhood (Primary); Lung Cancer, Non-Small Cell; Lung Cancer, Small Cell; Lymphoma, AIDS-Related; Lymphoma, Burkitt; Lymphoma, Cutaneous T-Cell; Lymphoma, Hodgkin, Adult; Lymphoma, Hodgkin, Childhood; Lymphoma, Non-Hodgkin, Adult; Lymphoma, Non-Hodgkin, Childhood; Lymphoma, Primary Central Nervous System (CNS); Macroglobulinemia, Waldenström; Malignant Fibrous Histiocytoma of Bone and Osteosarcoma; Medulloblastoma, Childhood; Medulloepithelioma, Childhood; Melanoma; Melanoma, Intraocular (Eye); Merkel Cell Carcinoma; Mesothelioma, Adult Malignant; Mesothelioma, Childhood; Metastatic Squamous Neck Cancer with Occult Primary; Mouth Cancer; Multiple Endocrine Neoplasia Syndromes, Childhood; Multiple Myeloma/Plasma Cell Neoplasm; Mycosis Fungoides; Myelodysplastic Syndromes; Myelodysplastic/Myeloproliferative Neoplasms; Myelogenous Leukemia, Chronic; Myeloid Leukemia, Adult Acute; Myeloid Leukemia, Childhood Acute; Myeloma, Multiple; Myeloproliferative Disorders, Chronic; Nasal Cavity and Paranasal Sinus Cancer; Nasopharyngeal Cancer; Nasopharyngeal Cancer, Childhood; Neuroblastoma; Non-Hodgkin Lymphoma, Adult; Non-Hodgkin Lymphoma, Childhood; Non-Small Cell Lung Cancer; Oral Cancer, Childhood; Oral Cavity Cancer, Lip and; Oropharyngeal Cancer; Osteosarcoma and Malignant Fibrous Histiocytoma of Bone; Ovarian Cancer, Childhood; Ovarian Epithelial Cancer; Ovarian Germ Cell Tumor; Ovarian Low Malignant Potential Tumor; Pancreatic Cancer; Pancreatic Cancer, Childhood; Pancreatic Cancer, Islet Cell Tumors; Papillomatosis, Childhood; Paranasal Sinus and Nasal Cavity Cancer; Parathyroid Cancer; Penile Cancer; Pharyngeal Cancer; Pineal Parenchymal Tumors of Intermediate Differentiation, Childhood; Pineoblastoma and Supratentorial Primitive Neuroectodermal Tumors, Childhood; Pituitary Tumor; Plasma Cell Neoplasm/Multiple Myeloma; Pleuropulmonary Blastoma, Childhood; Pregnancy and Breast Cancer; Primary Central Nervous System (CNS) Lymphoma; Prostate Cancer; Rectal Cancer; Renal Cell (Kidney) Cancer; Renal Pelvis and Ureter, Transitional Cell Cancer; Respiratory Tract Cancer with Chromosome 15 Changes; Retinoblastoma; Rhabdomyosarcoma, Childhood; Salivary Gland Cancer; Salivary Gland Cancer, Childhood; Sarcoma, Ewing Sarcoma Family of Tumors; Sarcoma, Kaposi; Sarcoma, Soft Tissue, Adult; Sarcoma, Soft Tissue, Childhood; Sarcoma, Uterine; Sezary Syndrome; Skin Cancer (Nonmelanoma); Skin Cancer, Childhood; Skin Cancer (Melanoma); Skin Carcinoma, Merkel Cell; Small Cell Lung Cancer; Small Intestine Cancer; Soft Tissue Sarcoma, Adult; Soft Tissue Sarcoma, Childhood; Squamous Cell Carcinoma; Squamous Neck Cancer with Occult Primary, Metastatic; Stomach (Gastric) Cancer; Supratentorial Primitive Neuroectodermal Tumors, Childhood; T-Cell Lymphoma, Cutaneous; Testicular Cancer; Throat Cancer; Thymoma and Thymic Carcinoma; Thyroid Cancer; Thyroid Cancer, Childhood; Transitional Cell Cancer of the Renal Pelvis and Ureter; Trophoblastic Tumor, Gestational; Unknown Primary Site, Carcinoma of, Adult; Unknown Primary Site, Cancer of, Childhood; Unusual Cancers of Childhood; Ureter and Renal Pelvis, Transitional Cell Cancer; Urethral Cancer; Uterine Cancer, Endometrial; Uterine Sarcoma; Vaginal Cancer; Vulvar Cancer; Waldenström Macroglobulinemia; or Wilms Tumor.

Administration Schedule

Administration of one or more agents (e.g., an HDAC inhibitor or an immunotherapy) can be intermittent; for example, administration can be once every two days, every three days, every five days, once a week, once or twice a month, and the like. The amount, forms, and/or amounts of the different forms can be varied at different times of administration.

Pulsed administration of one or more HDAC inhibitors or immunotherapies can be used for the treatment or prevention of a viral-induced cancer. Pulsed administration can be more effective than continuous treatment as pulsed doses can be lower than would be expected from continuous administration of the same composition. Each pulse dose can be reduced and the total amount of drug administered over the course of treatment to the patient can be minimized.

With pulse therapy, in vivo levels of an agent can drop below that level required for effective continuous treatment. Pulsed administration can reduce the amount of the composition administered to the patient per dose or per total treatment regimen with an increased effectiveness. Pulsed administration can provide a saving in time, effort, and expense and a lower effective dose can lessen the number and severity of complications that can be experienced by a subject. As such, pulsing can be more effective than continuous administration of the same composition.

Individual pulses can be delivered to a subject continuously over a period of several hours, such as about 2, 4, 6, 8, 10, 12, 14, or 16 hours, or several days, such as 2, 3, 4, 5, 6, or 7 day s, or from about 1 hour to about 24 hours or from about 3 hours to about 9 hours. Alternatively, periodic doses can be administered in a single bolus or a small number of injections of the composition over a short period of time, for example, less than 1 or 2 hours. For example, arginine butyrate can be administered over a period of 4 days with infusions for about 8 hours per day or overnight, followed by a period of 7 days of no treatment.

The interval between pulses or the interval of no delivery can be greater than 24 hours or can be greater than 48 hours, and can be for even longer such as for 3, 4, 5, 6, 7, 8, 9, or 10 days; two, three, or four weeks; or even longer. The interval between pulses can be determined by one of ordinary skill in the art. The interval between pulses can be calculated by administering another dose of the composition when the composition or the active component of the composition is no longer detectable in the patient prior to delivery of the next pulse. Intervals can also be calculated from the in vivo half-life of the composition. Intervals can be calculated as greater than the in vivo half-life, or 2, 3, 4, 5, and even 10 times greater than the composition half-life. Intervals can be 25, 50, 100, 150, 200, 250, 300, and even 500 times the half-life of the chemical composition.

The number of pulses in a single therapeutic regimen can be as little as two, but can be from about 5 to 10, 10 to 20, 15 to 30, or more. Subjects (e.g., patients) can receive one or more agents (e.g., drugs) for life according to the methods of this invention. Compositions can be administered by most any means, and can be delivered to the patient as an injection (e.g. intravenous, subcutaneous, intra-arterial), infusion or instillation, and more preferably by oral ingestion. Various methods and apparatus for pulsing compositions by infusion or other forms of delivery to the patient are disclosed in U.S. Pat. Nos. 4,747,825; 4,723,958; 4,948,592; 4,965,251; and 5,403,590.

In certain embodiments, the co-formulated unit dose comprising an HDAC inhibitor and an immunotherapy is administered daily. In further embodiments, administration is continuous. In some embodiments, the administration of the co-formulated unit dose is by pulsed administration. In certain embodiments, pulsed administration comprises administering pulses of the co-formulated unit dose for about 1 day, about 2 days, about 3 days, about 4 days, about 5 days, about 6 days, about 7 days, about 10 days, about 2 weeks, about 3 weeks, about 4 weeks, about 5 weeks, about 6 weeks, about 7 weeks, about 8 weeks, about 2 months, about 3 months, about 4 months, about 5 months, about 6 months, about 9 months, or about 12 months. In some embodiments, pulsed administration comprises intervals of not administering the co-formulated unit dose of about 1 day, about 2 days, about 3 days, about 4 days, about 5 days, about 6 days, about 7 days, about 10 days, about 2 weeks, about 3 weeks, about 4 weeks, about 5 weeks, about 6 weeks, about 7 weeks, about 8 weeks, about 2 months, about 3 months, about 4 months, about 5 months, about 6 months, about 9 months, or about 12 months.

In some embodiments, the administration of the co-formulated unit dose is by pulsed administration. In certain embodiments, the pulsed administration comprises administering the co-formulated unit dose for about 8 weeks, followed by not administering the co-formulated unit dose for about 4 weeks. In some embodiments, the pulsed administration comprises administering the co-formulated unit dose for about 6 weeks, followed by not administering the co-formulated unit dose for about 2 weeks. In certain embodiments, the pulsed administration comprises administering the co-formulated unit dose for about 4 weeks, followed by not administering the co-formulated unit dose for about 2 weeks. In some embodiments, the pulsed administration comprises administering the co-formulated unit dose for about 2 weeks, followed by not administering the co-formulated unit dose for about 2 weeks. In some embodiments, pulsed administration comprises pulses of administering the co-formulated unit dose for about 1 day, about 2 days, about 3 days, about 4 days, about 5 days, about 6 days, about 7 days, about 10 days, about 2 weeks, about 3 weeks, about 4 weeks, about 5 weeks, about 6 weeks, about 7 weeks, about 8 weeks, about 2 months, about 3 months, about 4 months, about 5 months, about 6 months, about 9 months, or about 12 months. In certain embodiments, pulsed administration comprises intervals of not administering the co-formulated unit dose of about 1 day, about 2 days, about 3 days, about 4 days, about 5 days, about 6 days, about 7 days, about 10 days, about 2 weeks, about 3 weeks, about 4 weeks, about 5 weeks, about 6 weeks, about 7 weeks, about 8 weeks, about 2 months, about 3 months, about 4 months, about 5 months, about 6 months, about 9 months, or about 12 months. In some embodiments, administration is continuous. In certain embodiments, administration is for the lifetime of the subject. In other embodiments, administration is for about 1 week, about 2 weeks, about 3 weeks, about 4 weeks, about 5 weeks, about 6 weeks, about 7 weeks, about 8 weeks, about 2 months, about 3 months, about 4 months, about 5 months, about 6 months, about 9 months, or about 12 months. In some embodiments, an immunotherapeutic is administered during intervals of not administering the co-formulated unit dose. In certain embodiments, an immunotherapeutic is administered in addition to the co-formulated unit dose. In some embodiments, an immunotherapeutic is administered simultaneously with the co-formulated unit dose. In other embodiments, an immunotherapeutic agent is administered separate from the co-formulated unit dose.

A pharmaceutical composition comprising an HDAC inhibitor can be administered to a subject before a pharmaceutical composition comprising an immunotherapeutic is administered to the subject. A pharmaceutical composition comprising an HDAC inhibitor can be co-administered to a subject with a pharmaceutical composition comprising an immunotherapeutic. A pharmaceutical composition comprising an HDAC inhibitor can be co-administered with a pharmaceutical composition comprising an immunotherapeutic and a pharmaceutical composition comprising one or more additional agents. The immunotherapeutic can be provided by pulsed administration. For example, a pharmaceutical composition comprising HDAC inhibitor can be administered to a subject, followed by administration of a pharmaceutical composition comprising an immunotherapeutic to the subject after an interval of time has passed, and this order of administration, at the same or similar time interval, can be repeated, for example, at least 1, 2, 3, 4, 5, 6, 7, 8, 9, 10, or more times.

EXAMPLES

Example 1—Treatment of Splenocytes with VRx-3996 Reduces FoxP3+ Regulatory T Cells CHR-39996 specifically reduces CD4+, CD25+, and FoxP3+ regulatory cells. This reduction is particularly striking when compared to another HDAC inhibitor entinostat.

For this experiment 7 treatment groups were created (untreated, DMSO treated, entinostat at 1 μM, VRx-3996 at 1 μM, VRx-3996 at 500 nM, VRx-3996 at 100 nM, and VRx-3996 at 1 nM. Each treatment was performed on splenocytes isolated from 5 naïve BALB/c mice (n=5 per treatment group). Spleens were processed in to single cell suspension using Miltenyi Gentlemacs. Red blood cells were lysed using RBC lysis buffer. Cells were counted and re-suspended in RPMI media containing 10% FBS. Cells from each spleen were seeded in a 12 well plate according to the table below at $3\times10^6$ cells/well. Test agents were added to each plate at the concentrations indicated in the table below and were incubated for 24 hours prior to FACS analysis. FACS analysis consisted of the following markers: live/dead, CD45, CD3, CD4, CD25 and FOXP3. Results are shown below in Table 1. Compared to entinostat at 1 μM, VRx-3996 led to nearly 47-fold reduction in FoxP3, CD25+ T cells (last column of Table 1 and FIG. 1A). This suppressive effect was seen at least as low as 100 nM (last column of Table 1 and FIG. 1B)

TABLE 1

VRx-3996 reduces FoxP3+, CD25+ T regulatory cells. Shown are percentages of the indicated cell population ± SD

| group | Live | CD45± | CD45+ CD3+ | CD45+ CD3+ CD4+ | CD45+ CD3+ CD4+ CD25+ | CD45+ CD3+ CD4+ FoxP3+ | CD45+ CD3+ CD4+ FoxP3+, CD25− | CD45+ CD3+ CD4+ FoxP3− CD25+ | CD45+ CD3+ CD4+ FoxP3+, CD25+ |
|---|---|---|---|---|---|---|---|---|---|
| untreated | 98.3 | 97.5 | 42.6 | 29.7 | 8.26 | 13 | 5.13 | 0.69 | 7.05 |
| | ±0.35 | ±1.0 | ±1.79 | ±1.32 | ±1.63 | ±1.41 | ±0.18 | ±0.15 | ±1.55 |
| DMSO | 98.2 | 97.6 | 43.1 | 29.8 | 7.74 | 13.5 | 5.56 | 0.66 | 6.58 |
| | ±0.37 | ±0.57 | ±1.69 | ±1.48 | ±1.1 | ±1.63 | ±0.63 | ±0.17 | ±1.02 |
| Entinostat | 97.6 | 99.1 | 53.9 | 38.5 | 10.4 | 10.1 | 2.33 | 4.57 | 5.12 |
| 1 uM | ±0.33 | ±0.27 | ±2.76 | ±2.33 | ±2.09 | ±2.82 | ±0.83 | ±0.89 | ±1.77 |
| VRx-3996 | 84.7 | 99.6 | 94.7 | 82.2 | 3.57 | 3.85 | 0.8 | 1.96 | 0.14 |
| 1 uM | ±2.75 | ±0.17 | ±0.98 | ±1.4 | ±1.76 | ±1.76 | ±0.44 | ±0.48 | ±0.11 |
| VRx-3996 | 87.2 | 99.5 | 94 | 80.6 | 3.03 | 2.36 | 0.47 | 1.69 | 0.22 |
| 500 nM | ±1.88 | ±0.29 | ±4.4 | ±5.32 | ±1.35 | ±1.35 | ±0.35 | ±0.36 | ±0.32 |
| VRx-3996 | 91.4 | 99.6 | 94 | 75.3 | 1.89 | 1.62 | 0.34 | 1.22 | 0.064 |
| 100 nM | ±2.47 | ±0.12 | ±0.83 | ±2.13 | ±1.13 | ±1.13 | ±0.27 | ±0.24 | ±0.044 |
| VRx- | 98.4 | 98.6 | 46.9 | 32.4 | 7.93 | 12 | 4.47 | 1.14 | 6.2 |
| 39961 nM | ±0.36 | ±0.36 | ±1.87 | ±1.47 | ±1.51 | ±1.51 | ±0.68 | ±0.31 | ±1.18 |

Figure 2A:
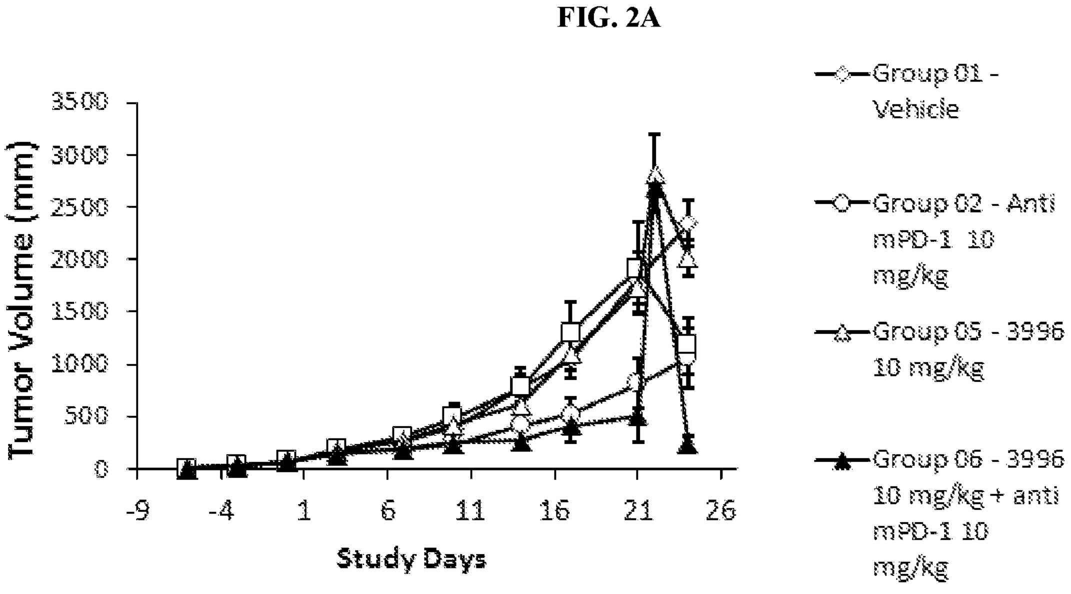
FIGS. 2A-B shows mean tumor volume for mice inoculated with CT26 tumor cell lines and treated with a combination of anti-PD-1 and VRx-3996.
Figure 2B:
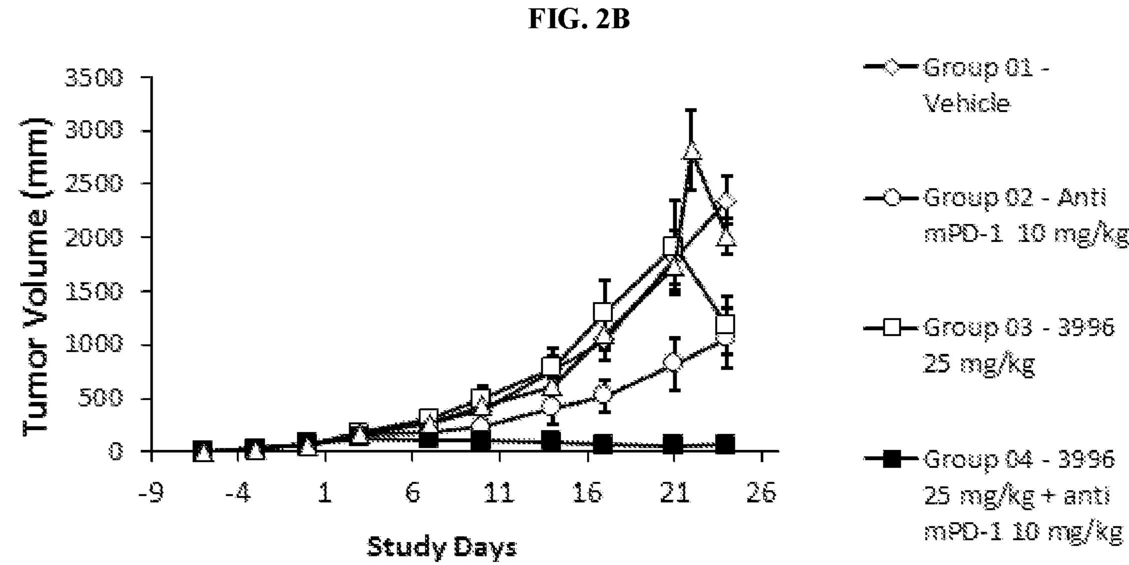
Figure 3A:
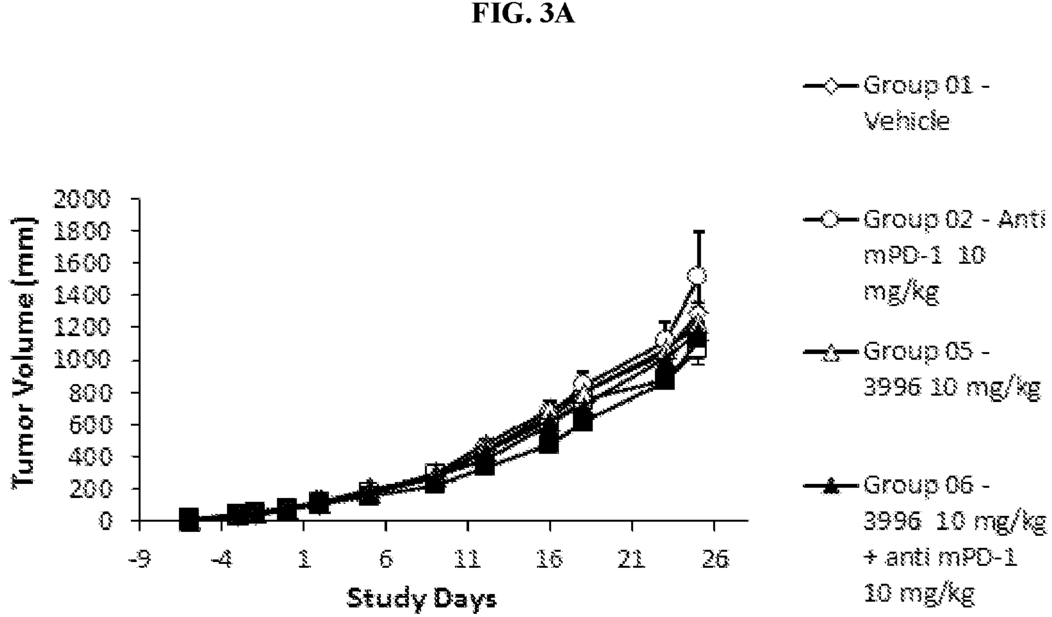
FIGS. 3A-B shows mean tumor volume for mice inoculated with 4T1 tumor cell lines and treated with a combination of anti-PD-1 and VRx-3996.
Figure 3B:
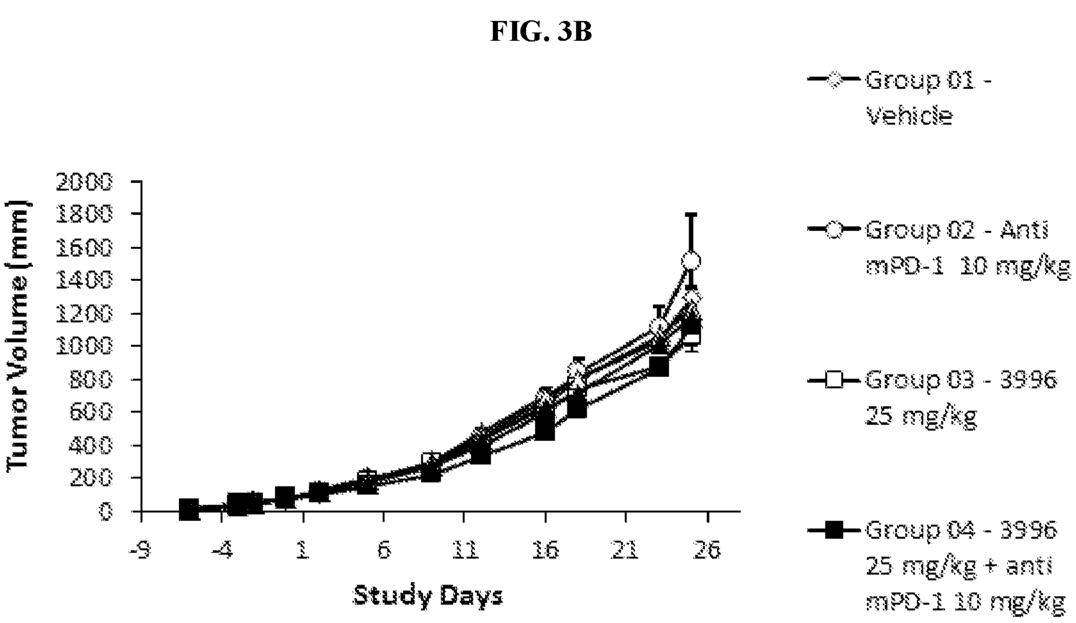

Example 2—VRx-3996 Increases Efficacy of Immunotherapy in a Mouse Xenograft Model The effect of VRx-3996 seen on regulatory T cells could lead to an enhancement of the efficacy of immunotherapeutics such as those that target the PD-1/PD-L1 axis. In this example, VRx-3996 treatment was combined with anti-PD-1 antibody treatment in two different tumor xenograft models 4T1 and CT26. Each model was tested in 6 different treatment groups (vehicle, anti-PD-1 at 10 mg/kg, VRx-3996 at 25 mg/kg, VRx-3996 at 10 mg/kg, anti-PD-1 at 10 mg/kg with VRx-3996 at 25 mg/kg, anti-PD-1 at 10 mg/kg with VRx-3996 at 10 mg/kg), each group consisted of 8 animals. Animals were inoculated in the right rear flank with either 4T1 or CT26, dosing was started when tumors were 65-90 $mm^3$ and continued for 21 days. Animals were dosed daily with VRx-3996 and twice weekly with anti-PD-1. FIG. 2A and FIG. 2B show that mice receiving CT26 tumor exhibited greater reduction in tumor growth with a combination of anti-PD-1 and VRx-3996 (filled shapes) compared with either PD-1 or VRx-3996 alone. This was seen for both concentrations of VRx-3995 (10 mg/kg/day, FIG. 2A) and (25 mg/kg/day FIG. 2B). FIG. 3A and FIG. 3B show that the 4T1 tumor line was resistant to this effect. Indeed this tumor was resistant to anti-PD1 treatment alone, indicating that HDAC treatment with VRx-3996 can specifically synergize with immunotherapies such as anti-PD-1 and potentially all checkpoint inhibitors.

Example 3—Treatment of Patients Receiving HDAC Inhibitors with CAR T Cells

A patient either diagnosed with, or suspected of having, an Epstein Barr Virus (EBV)-associated malignancy such as nasopharyngeal carcinoma, Hodgkin's disease, Burkitt's lymphoma, post-transplantation lymphoproliferative disease, or gastric carcinoma can be treated. A health care professional administers a dose of a pharmaceutical composition comprising JNJ-26481585, followed by treatment with CAR T cells administered i.v. at a dose of $5\times10^6$ cells/$m^2$. The CAR T cells are autologous, prepared from the patient's blood, and the chimeric receptor is expressed by transducing the cells with a retrovirus encoding the chimeric antigen receptor The patient is administered a single daily dose in tablet form, where the tablet contains 5 mg of JNJ-26481585. CAR T cells are administered two weeks after treatment with JNJ-26481585. During the period of administration, the subject can optionally also be administered an additional chemotherapeutic agent to treat the malignancy.

Example 4—Treatment of Patients Receiving HDAC Inhibitors with CAR T Cells

A patient is diagnosed with or suspected of having a CMV positive mucoepidermoid carcinoma. A health care professional administers a dose of a pharmaceutical composition comprising chidamide, followed by treatment with CAR T cells administered i.v. at a dose of $1\times10^7$ cells/$m^2$. The CAR T cells are autologous, prepared from the patient's blood, and the chimeric receptor is expressed by transducing the cells with a retrovirus encoding the chimeric antigen receptor which has specificity for a CMV protein. The patient is administered an oral composition containing 20 mg of chidamide twice a week for two weeks. CAR T cells are administered after two weeks of treatment with chidamide. During the period of administration, the subject can optionally also be administered an additional chemotherapeutic agent to treat the malignancy.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for treating colorectal carcinoma in an individual in need thereof comprising administering to the individual afflicted with colorectal carcinoma a therapeutically effective amount of:

a) an HDAC inhibitor, wherein the HDAC inhibitor comprises (2-(6-{[(6-Fluoroquinolin-2-yl)methyl]

amino}-3-azabicyclo[3.1.0]hex-3-yl)-N-hydroxypyrimidine-5-carboxamide); and b) an anti-PD-1 antibody or antigen binding fragment thereof.

2. The method of claim 1, wherein the HDAC inhibitor is administered orally.

3. The method of claim 1, wherein the HDAC inhibitor is administered at a dose of less than 40 mg per day.

4. The method of claim 1, wherein the antibody or antigen binding fragment comprises nivolumab, pembrolizumab, pidilizumab, or a combination thereof.

5. The method of claim 1, wherein the HDAC inhibitor increases expression of a checkpoint inhibitor present on T cells.

6. The method of claim 5, wherein the checkpoint inhibitor is PD-1.

7. The method of claim 1, wherein the HDAC inhibitor increases expression of a checkpoint inhibitor present on a cancer cell.

8. The method of claim 7, wherein the checkpoint inhibitor is PD-L1.

9. The method of claim 7, wherein the checkpoint inhibitor is PD-L2.

* * * * *